(12) United States Patent
Conte et al.

(10) Patent No.: US 10,111,847 B2
(45) Date of Patent: *Oct. 30, 2018

(54) COMPOUNDS AND METHODS FOR MODULATING VASCULAR INJURY

(71) Applicants: The Regents of the University of California, Oakland, CA (US); The Brigham and Women's Hospital, Inc., Boston, CA (US)

(72) Inventors: Michael S. Conte, Hillsborough, CA (US); Charles N. Serhan, Needham, MA (US); Tejal A. Desai, San Francisco, CA (US)

(73) Assignees: The Regents of the University of California, Oakland, CA (US); The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,778

(22) Filed: Sep. 2, 2016

(65) Prior Publication Data

US 2017/0216238 A1    Aug. 3, 2017

Related U.S. Application Data

(63) Continuation of application No. 14/426,341, filed as application No. PCT/US2013/058753 on Sep. 9, 2013, now Pat. No. 9,463,177.

(60) Provisional application No. 61/699,109, filed on Sep. 10, 2012.

(51) Int. Cl.
    *A61K 31/202*    (2006.01)

(52) U.S. Cl.
    CPC .................... *A61K 31/202* (2013.01)

(58) Field of Classification Search
    CPC .................................................. A61K 31/202
    USPC ......................................................... 514/560
    See application file for complete search history.

(56) References Cited

U.S. PATENT DOCUMENTS

| | | | |
|---|---|---|---|
| 4,580,568 A | 4/1986 | Gianturco | |
| 4,733,665 A | 3/1988 | Palmaz | |
| 5,755,771 A | 5/1998 | Penn et al. | |
| 6,033,434 A | 3/2000 | Borghi | |
| 6,106,548 A | 8/2000 | Roubin et al. | |
| 8,070,797 B2 | 12/2011 | Flanagan et al. | |
| 8,604,229 B2* | 12/2013 | Van Dyke | A61K 31/202 554/218 |
| 8,933,270 B2* | 1/2015 | Serhan | A61K 31/202 562/587 |
| 9,463,177 B2* | 10/2016 | Conte | A61K 45/06 |
| 2004/0116408 A1 | 7/2004 | Serhan | |
| 2005/0238589 A1 | 10/2005 | Van Dyke et al. | |
| 2005/0261255 A1 | 11/2005 | Serhan et al. | |
| 2006/0293288 A1 | 12/2006 | Serhan et al. | |
| 2008/0279925 A1 | 11/2008 | Allam et al. | |
| 2009/0053392 A1 | 2/2009 | Kramer-Brown et al. | |
| 2009/0216317 A1 | 8/2009 | Cromack et al. | |
| 2009/0285873 A1 | 11/2009 | Lim et al. | |
| 2010/0048705 A1 | 2/2010 | Smith et al. | |
| 2010/0105773 A1 | 4/2010 | Smith et al. | |
| 2010/0222875 A1 | 9/2010 | Pacetti | |
| 2010/0318193 A1 | 12/2010 | Desai et al. | |
| 2010/0331819 A1 | 12/2010 | Hossainy et al. | |
| 2011/0190242 A1 | 8/2011 | Gjorstrup | |
| 2012/0015019 A1 | 1/2012 | Pacetti et al. | |
| 2012/0033366 A1 | 2/2012 | Milton | |
| 2012/0060969 A1 | 3/2012 | Pacetti | |
| 2012/0108959 A1 | 5/2012 | Consigny et al. | |
| 2012/0114734 A1 | 5/2012 | Desai et al. | |
| 2012/0116305 A1 | 5/2012 | Papp | |
| 2012/0150283 A1 | 6/2012 | Kleiner | |
| 2014/0170204 A1 | 6/2014 | Desai et al. | |
| 2015/0119807 A1 | 4/2015 | Desai et al. | |

FOREIGN PATENT DOCUMENTS

| WO | WO 2004/014835 | 2/2004 |
|---|---|---|
| WO | WO 2005/105025 | 11/2005 |

OTHER PUBLICATIONS

Ho et al. The American Journal of Pathology, vol. 177, No. 4, Oct. 2010.*
Ramli et al. Cardiology Journal, 2011, vol. 18, No. 4, pp. 352-363.*
Connor et al. Nature Medicine, vol. 13 [ No. 7 [ Jul. 2007.*
Zhang et al. Annu. Rev. Nutr. 2012. 32:203-27m Review in Advance on Mar. 9, 2012, specifically p. 228.*
Recchuiuti et al. Front. Immunol., Oct. 22, 2012, Article 298, 1-23, Front. Immunol., Oct. 22, 2012, Article 298, 1-23.*
Moses, New England Journal of Medicine. 2003, 349 (14): 1315-23.*
Acharya and Park (2006) "Mechanisms of controlled drug release from drug-eluting stents" *Advanced Drug Delivery Reviews* 58(3):387-401.

(Continued)

*Primary Examiner* — Nizal S Chandrakumar
(74) *Attorney, Agent, or Firm* — Edward J. Baba; Shweta Chandra; Bozicevic, Field & Francis LLP

(57) ABSTRACT

Methods of modulating healing response to vascular injury and/or vascular scarring in a subject are provided. As such, aspects of the disclosure relate to the use of pro-resolving lipid mediators to modulate inflammation and/or restenosis of a vascular wall. Another aspect of the disclosure relates to the use of pro-resolving lipid mediators to modulate a biological activity of vascular smooth muscle cells (VSMC) or vascular endothelial cells (VEC). Pro-resolving lipid mediators that fmd use in the subject methods include derivatives of omega-3 polyunsaturated fatty acids and omega-6 polyunsaturated fatty acids, such as resolvins, protectins, lipoxins and maresins and their therapeutically stable analogs. Also provided are vascular devices and compositions for use in the subject methods. Such methods, devices and compositions fmd use in a variety of applications, including applications related to treatment of vascular injuries and vascular scarring (e.g., restenosis), and applications related to chronic inflammatory diseases of the vascular wall.

8 Claims, 27 Drawing Sheets

Specification includes a Sequence Listing.

(56) References Cited

OTHER PUBLICATIONS

Akagi et al. (2015) "Systemic delivery of proresolving lipid mediators resolvin D2 and maresin 1 attenuates intimal hyperplasia in mice" FASEB J. 29:2504-2513.

Bannenberg et al. (2010) "Specialized pro-resolving lipid mediators in the inflammatory response: An update, Biochimica et Biophysica Acta (BBA)" *Molecular and Cell Biology of Lipids* 1801(12):1260-1273.

Connor et al. (2007) "Increased dietary intake of omega-3-polyunsaturated fatty acids reduces pathological retinal angiogenesis" Nature Medicine 13(7):868-873.

Conte et al. (1994) "Efficient repopulation of denuded rabbit arteries with autologous genetically modified endothelial cells" *Circulation* 89:2161-2169.

Dalli et al. (2013) "The novel 13S,14S-epoxy-maresin is converted by human macrophages to maresin 1 (MaR1), inhibits leukotriene A4 hydrolase (LTA4H), and shifts macrophage phenotype" *FASEB* 27(7):2573-2583.

Ho et al. (2008) "C-reactive protein and vein graft disease: evidence for a direct effect on smooth muscle cell phenotype via modulation of PDGF receptor-beta" *Am J Physiol Heart Circ Physiol.* 295:H1132-H1140.

Ho et al. (2010) "Aspirin-triggered lipoxin and resolvin El modulate vascular smooth muscle phenotype 25 and correlate with peripheral atherosclerosis" *Am J Pathol.* 177(4):2116-2123.

Patricia et al. (1999) "Lipoxygenase products increase monocyte adhesion to human aortic endothelial 5 cells" *Arterioscler Thromb Vasc Biol.* 19:2615-2622.

Ramli et al. (2011) "Novel therapeutic targets for preserving a healthy endothelium: Strategies for reducing the risk of vascular and cardiovascular disease" Cardiology Journal 18(4):352-363.

Recchuiuti and Serhan (2012) "Pro-resolving lipid mediators (SPMs) and their actions in regulating miRNA in novel resolution circuits in inflammation" Front. Immunol., vol. 3, Article 298, pp. 1-23.

Serhan et al. (2008) "Resolving inflammation: dual anti-inflammatory and pro-resolution lipid mediators" *Nature Reviews Immunology* 8:349-361.

Wang et al. (2005) "Regulation of vein graft hyperplasia by survivin, an inhibitor of apoptosis protein" *Arterioscler Thromb Vasc Biol.* 25:2081-2087.

Weylandt et al. (2012) "Omega-3 fatty acids and their lipid mediators: Towards an understanding of resolvin and protectin formation" *Prostaglandins & Other Lipid Mediators* 97(3-4):73-82.

Wu et al. (2016) "Perivasular delivery of resolving D1 inhibits neointimal hyperplasia in a rat model of arterial injury" J. Vasc. Surg. p. 1-11 (available online Mar. 29, 2016).

Zhang and Spite (2012) "Resolvins: Anti-Inflammatory and Proresolving Mediators Derived from Omega-3 Polyunsaturated Fatty Acids" Annu. Rev. Nutr. 32:203-227. Review in Advance on Mar. 9, 2012, specifically p. 228.

O'Brien et al. (2002) "Passivation of nitinol wire for vascular implants—a demonstration of the benefits" Biomaterials 23:1739-1748.

Shabalovskaya et al. (2008) "Comparative in vitro performances of bare Nitinol surfaces" Bio-Medical Materials and Engineering 18:1-14.

Shabalovskaya et al. (2008) "Critical overview of Nitinol surfaces and their modifications for medical applications" Acta Biomaterialia 4:447-467.

* cited by examiner

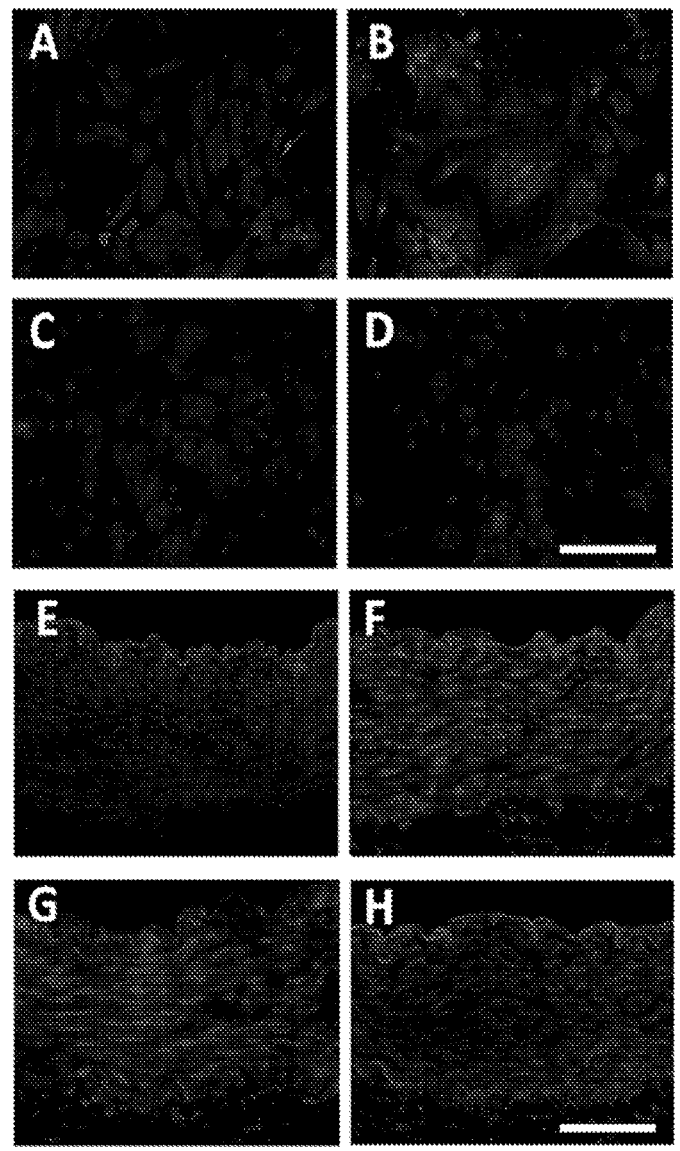
Figure 4
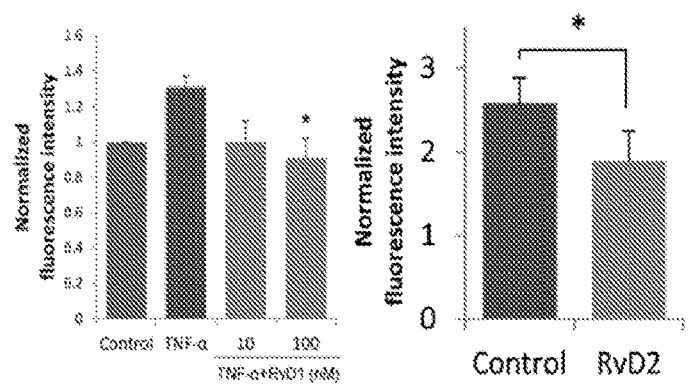

(A) Injured / Vehicle (n=9)

(B) Injured / RvD2 (n=7)

(C) Injured / 7R-Mar-1 (n=9)

FVB mice
Common carotid ligation model
Time point 14 days
Total received doses 500 ng/mouse
Analysis at mid CCA level (2.5 mm from ligature)

D

E

```
                              SEQUENCE LISTING

<160> NUMBER OF SEQ ID NOS: 36

<210> SEQ ID NO 1
<211> LENGTH: 27
<212> TYPE: DNA
<213> ORGANISM: Artificial sequence
<220> FEATURE:
<223> OTHER INFORMATION: synthetic sequence

<400> SEQUENCE: 1
tgcaagtcta catatcaccc aagaata                                          27

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
ggtagaccct cgctggaaca                                                  20

<210> SEQ ID NO 3
<211> LENGTH: 20
<212> TYPE: DNA
<213> ORGANISM: Artificial sequence
<220> FEATURE:
<223> OTHER INFORMATION: synthetic sequence

<400> SEQUENCE: 3
gccggccagc ttatacacaa                                                  20

<210> SEQ ID NO 4
<211> LENGTH: 18
<212> TYPE: DNA
<213> ORGANISM: Artificial sequence
<220> FEATURE:
<223> OTHER INFORMATION: synthetic sequence

<400> SEQUENCE: 4
tggccacgtc cagtttcc                                                    18

<210> SEQ ID NO 5
<211> LENGTH: 24
<212> TYPE: DNA
<213> ORGANISM: Artificial sequence
<220> FEATURE:
<223> OTHER INFORMATION: synthetic sequence

<400> SEQUENCE: 5
agagggcctg tacctcatct actc                                             24

<210> SEQ ID NO 6
<211> LENGTH: 22
<212> TYPE: DNA
<213> ORGANISM: Artificial sequence
<220> FEATURE:
<223> OTHER INFORMATION: synthetic sequence

<400> SEQUENCE: 6
ggttgacctt ggtctggtag ga                                               22
```

```
<210> SEQ ID NO 7
<211> LENGTH: 24
<212> TYPE: DNA
<213> ORGANISM: Artificial sequence
<220> FEATURE:
<223> OTHER INFORMATION: synthetic sequence

<400> SEQUENCE: 7
ccctaaacag atgaagtgct cctt                                              24

<210> SEQ ID NO 8
<211> LENGTH: 21
<212> TYPE: DNA
<213> ORGANISM: Artificial sequence
<220> FEATURE:
<223> OTHER INFORMATION: synthetic sequence

<400> SEQUENCE: 8
ggtggtcgga gattcgtagc t                                                 21

<210> SEQ ID NO 9
<211> LENGTH: 20
<212> TYPE: DNA
<213> ORGANISM: Artificial sequence
<220> FEATURE:
<223> OTHER INFORMATION: synthetic sequence

<400> SEQUENCE: 9
cagcagcaag tgtcccaaag                                                   20

<210> SEQ ID NO 10
<211> LENGTH: 23
<212> TYPE: DNA
<213> ORGANISM: Artificial sequence
<220> FEATURE:
<223> OTHER INFORMATION: synthetic sequence

<400> SEQUENCE: 10
gaatcctgaa cccacttctg ctt                                               23

<210> SEQ ID NO 11
<211> LENGTH: 20
<212> TYPE: DNA
<213> ORGANISM: Artificial sequence
<220> FEATURE:
<223> OTHER INFORMATION: synthetic sequence

<400> SEQUENCE: 11
ccgggaacga aagagaagct                                                   20

<210> SEQ ID NO 12
<211> LENGTH: 18
<212> TYPE: DNA
<213> ORGANISM: Artificial sequence
<220> FEATURE:
<223> OTHER INFORMATION: synthetic sequence

<400> SEQUENCE: 12
agcagcccca gggagaag                                                     18

<210> SEQ ID NO 13
<211> LENGTH: 28
<212> TYPE: DNA
<213> ORGANISM: Artificial sequence
<220> FEATURE:
<223> OTHER INFORMATION: synthetic sequence
```

<400> SEQUENCE: 13
gaatcagaaa tccttctatc atgtaagc                                          28

<210> SEQ ID NO 14
<211> LENGTH: 23
<212> TYPE: DNA
<213> ORGANISM: Artificial sequence
<220> FEATURE:
<223> OTHER INFORMATION: synthetic sequence

<400> SEQUENCE: 14
actaccacca tgctctcctt gaa                                               23

<210> SEQ ID NO 15
<211> LENGTH: 21
<212> TYPE: DNA
<213> ORGANISM: Artificial sequence
<220> FEATURE:
<223> OTHER INFORMATION: synthetic sequence

<400> SEQUENCE: 15
caagcttgct ggtgaaaagg a                                                 21

<210> SEQ ID NO 16
<211> LENGTH: 27
<212> TYPE: DNA
<213> ORGANISM: Artificial sequence
<220> FEATURE:
<223> OTHER INFORMATION: synthetic sequence

<400> SEQUENCE: 16
tgaagtactt atagtcaagg gcatatc                                           27

<210> SEQ ID NO 17
<211> LENGTH: 19
<212> TYPE: DNA
<213> ORGANISM: Artificial sequence
<220> FEATURE:
<223> OTHER INFORMATION: synthetic sequence

<400> SEQUENCE: 17
atttgggtcg cggttcttg                                                    19

<210> SEQ ID NO 18
<211> LENGTH: 21
<212> TYPE: DNA
<213> ORGANISM: Artificial sequence
<220> FEATURE:
<223> OTHER INFORMATION: synthetic sequence

<400> SEQUENCE: 18
tgccttgaca ttctcgatgg t                                                 21

<210> SEQ ID NO 19
<211> LENGTH: 26
<212> TYPE: DNA
<213> ORGANISM: Artificial sequence
<220> FEATURE:
<223> OTHER INFORMATION: synthetic sequence

<400> SEQUENCE: 19
ggtctacatt tcacccaaga atacag                                            26

```
<210> SEQ ID NO 20
<211> LENGTH: 21
<212> TYPE: DNA
<213> ORGANISM: Artificial sequence
<220> FEATURE:
<223> OTHER INFORMATION: synthetic sequence

<400> SEQUENCE: 20
actggtagac cctcgctgga a                                              21

<210> SEQ ID NO 21
<211> LENGTH: 19
<212> TYPE: DNA
<213> ORGANISM: Artificial sequence
<220> FEATURE:
<223> OTHER INFORMATION: synthetic sequence

<400> SEQUENCE: 21
agacgcagct gagcaagga                                                 19

<210> SEQ ID NO 22
<211> LENGTH: 22
<212> TYPE: DNA
<213> ORGANISM: Artificial sequence
<220> FEATURE:
<223> OTHER INFORMATION: synthetic sequence

<400> SEQUENCE: 22
cacagtcgga aaagcagatg ag                                             22

<210> SEQ ID NO 23
<211> LENGTH: 20
<212> TYPE: DNA
<213> ORGANISM: Artificial sequence
<220> FEATURE:
<223> OTHER INFORMATION: synthetic sequence

<400> SEQUENCE: 23
ggaagagcag tccccaaaca                                                20

<210> SEQ ID NO 24
<211> LENGTH: 21
<212> TYPE: DNA
<213> ORGANISM: Artificial sequence
<220> FEATURE:
<223> OTHER INFORMATION: synthetic sequence

<400> SEQUENCE: 24
gggctagagg cttgtcactc a                                              21

<210> SEQ ID NO 25
<211> LENGTH: 21
<212> TYPE: DNA
<213> ORGANISM: Artificial sequence
<220> FEATURE:
<223> OTHER INFORMATION: synthetic sequence

<400> SEQUENCE: 25
tgtacctgtc ctgcgtgatg a                                              21

<210> SEQ ID NO 26
<211> LENGTH: 24
<212> TYPE: DNA
<213> ORGANISM: Artificial sequence
<220> FEATURE:
<223> OTHER INFORMATION: synthetic sequence
```

<400> SEQUENCE: 26 tcgttttcc atcttcttct ttgg                                          24

<210> SEQ ID NO 27
<211> LENGTH: 17
<212> TYPE: DNA
<213> ORGANISM: Artificial sequence
<220> FEATURE:
<223> OTHER INFORMATION: synthetic sequence

<400> SEQUENCE: 27
tgggtccagg atgccat                                                 17

<210> SEQ ID NO 28
<211> LENGTH: 22
<212> TYPE: DNA
<213> ORGANISM: Artificial sequence
<220> FEATURE:
<223> OTHER INFORMATION: synthetic sequence

<400> SEQUENCE: 28
agtcgtgtgt tcttgggttg tg                                           22

<210> SEQ ID NO 29
<211> LENGTH: 21
<212> TYPE: DNA
<213> ORGANISM: Artificial sequence
<220> FEATURE:
<223> OTHER INFORMATION: synthetic sequence

<400> SEQUENCE: 29
acgaccacga tccacttcat c                                            21

<210> SEQ ID NO 30
<211> LENGTH: 19
<212> TYPE: DNA
<213> ORGANISM: Artificial sequence
<220> FEATURE:
<223> OTHER INFORMATION: synthetic sequence

<400> SEQUENCE: 30
aaggacaccc gcactccat                                               19

<210> SEQ ID NO 31
<211> LENGTH: 23
<212> TYPE: DNA
<213> ORGANISM: Artificial sequence
<220> FEATURE:
<223> OTHER INFORMATION: synthetic sequence

<400> SEQUENCE: 31
gagtcggcaa agaaatcaag atg                                          23

<210> SEQ ID NO 32
<211> LENGTH: 24
<212> TYPE: DNA
<213> ORGANISM: Artificial sequence
<220> FEATURE:
<223> OTHER INFORMATION: synthetic sequence

<400> SEQUENCE: 32
gcagagctgt attcctcatt ttca                                         24

```
<210> SEQ ID NO 33
<211> LENGTH: 21
<212> TYPE: DNA
<213> ORGANISM: Artificial sequence
<220> FEATURE:
<223> OTHER INFORMATION: synthetic sequence

<400> SEQUENCE: 33
gtgaaaagga cccctcgaag t                                              21

<210> SEQ ID NO 34
<211> LENGTH: 27
<212> TYPE: DNA
<213> ORGANISM: Artificial sequence
<220> FEATURE:
<223> OTHER INFORMATION: synthetic sequence

<400> SEQUENCE: 34
tcattatagt caagggcata tcctaca                                         27

<210> SEQ ID NO 35
<211> LENGTH: 18
<212> TYPE: DNA
<213> ORGANISM: Artificial sequence
<220> FEATURE:
<223> OTHER INFORMATION: synthetic sequence

<400> SEQUENCE: 35
tccccgagac acgatggt                                                   18

<210> SEQ ID NO 36
<211> LENGTH: 23
<212> TYPE: DNA
<213> ORGANISM: Artificial sequence
<220> FEATURE:
<223> OTHER INFORMATION: synthetic sequence

<400> SEQUENCE: 36
acaacatcca ctttgccaga gtt                                             23
```

COMPOUNDS AND METHODS FOR MODULATING VASCULAR INJURY

CROSS-REFERENCE TO RELATED APPLICATIONS

This application is a continuation of U.S. patent application Ser. No. 14/426,341, filed on Mar. 5, 2015, issued as U.S. Pat. No. 9,463,177, which is a 371 of PCT/US2013/058753, filed on Sep. 9, 2013, which claims priority to U.S. Provisional Patent Application Ser. No. 61/699,109, filed on Sep. 10, 2012, the disclosures of which are herein incorporated by reference in their entirety.

STATEMENT REGARDING FEDERALLY SPONSORED RESEARCH

This invention was made with government support under Grant No. P01 GM095467, awarded by the National Institutes of Health. The government has certain rights in the invention.

INTRODUCTION

Failure of therapeutic interventions designed to open, bypass, or access blood vessels is a clinical problem that incurs significant mortality, morbidity, and costs. Whether it be an endovascular intervention (angioplasty, atherectomy, stenting), a bypass graft, or an arteriovenous access procedure the final common cause of failure is excessive scarring of the vessel wall (intimal hyperplasia) leading to lumen narrowing and loss of patency (restenosis), a manifestation of the local response to injury. Such procedures have rates of failure that approach 50% within 5 years depending on the circulatory bed (coronary or peripheral) and method applied. Inflammatory cells are recruited to sites of vascular damage, where they initiate processes of repair including clearance of cellular debris and recruitment of other local and blood-borne cells. The net result is the development of neointimal hyperplasia and/or restenosis, a lesion comprised of cells and extracellular matrix which, when excessive, leads to luminal re-narrowing. Methods and compositions that control this injury response and accelerate tissue healing are of interest.

SUMMARY

Methods of modulating healing response to vascular injury and/or vascular scarring in a subject are provided. As such, aspects of the disclosure relate to the use of pro-resolving lipid mediators to modulate inflammation and/or restenosis of a vascular wall. Another aspect of the disclosure relates to the use of pro-resolving lipid mediators to modulate a biological activity of vascular smooth muscle cells (VSMC) and vascular endothelial cells (VEC). Pro-resolving lipid mediators that find use in the subject methods include derivatives of omega-3 polyunsaturated fatty acids and omega-6 polyunsaturated fatty acids, such as resolvins, protectins, lipoxins and maresins and their therapeutically stable analogs. Also provided are vascular devices and compositions for use in the subject methods. Such methods, devices and compositions find use in a variety of applications, including applications related to treatment of vascular injuries and vascular scarring (e.g., restenosis), and applications related to chronic inflammatory diseases of the vascular wall.

BRIEF DESCRIPTION OF THE DRAWINGS

The embodiments described in this disclosure are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 4 shows RvD treatment modulates superoxide production by VSMC in-vitro and in-vivo: (A-D, I) RvD1 treatment reduces TNF-α-induced superoxide production in cultured HVSMC. Representative merged images of DHE staining counterstained with DAPI of untreated VSMC (A), positive control (TNF-α, B), TNF-α with 10 nM RvD1 (C), and TNF-α with 100 nM RvD1 (D; bar=200 µm). Quantitative comparison of DHE staining intensity is shown in panel (I). (E-H, J) RvD2 treatment reduces oxidative stress in the acutely injured rabbit artery (3 days post angioplasty). Representative images of DHE staining of an uninjured aorta (E), balloon injured and untreated iliac artery (F), vehicle-treated (G), and RvD2-treated (H) femoral arteries (bar=100 µm). Quantitative comparison of staining intensity is shown in panel (J).

DETAILED DESCRIPTION

Figure 1:
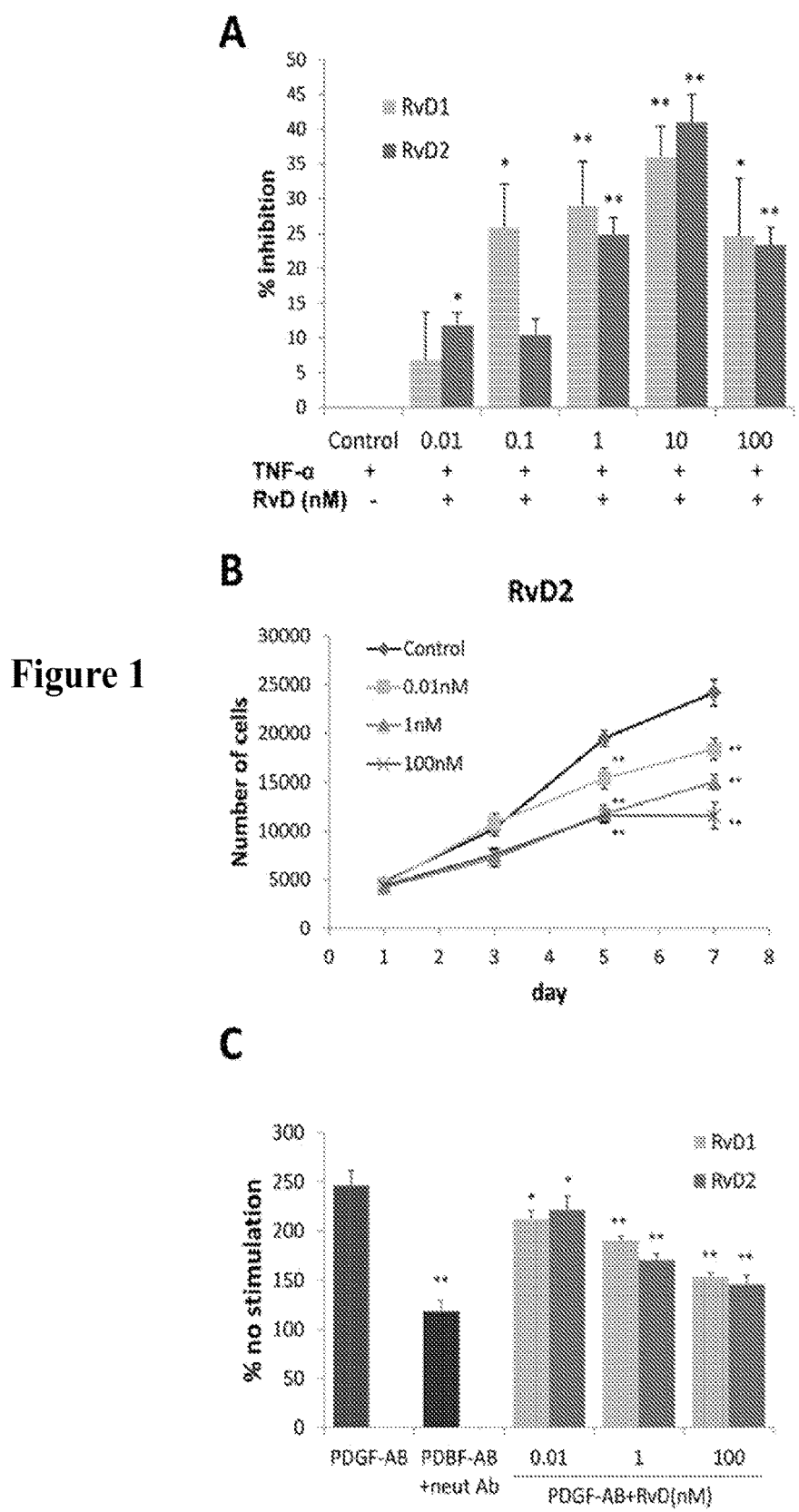
FIG. 1 illustrates RvD1 and RvD2 attenuation of cell adhesion, proliferation, and migration responses of human vascular smooth muscle cells (VSMC) in-vitro: (A) Monocyte adhesion to VSMC; (B) Dose-dependent inhibition of VSMC proliferation is shown for RvD2; and (C) VSMC migration response to PDGF-AB where dose-dependent inhibition of chemotaxis is demonstrated for both RvD1 and RvD2.

Methods of modulating healing response to vascular injury and/or vascular scarring in a subject are provided. As such, aspects of the disclosure relate to the use of pro-resolving lipid mediators to modulate inflammation and/or restenosis of a vascular wall. Another aspect of the disclosure relates to the use of pro-resolving lipid mediators to modulate a biological activity of vascular smooth muscle cells (VSMC) and vascular endothelial cells (VEC). Pro-resolving lipid mediators that find use in the subject methods include derivatives of omega-3 polyunsaturated fatty acids and omega-6 polyunsaturated fatty acids, such as resolvins, protectins, lipoxins and maresins and their therapeutically stable analogs. Also provided are vascular devices and compositions for use in the subject methods. Such methods, devices and compositions find use in a variety of applications, including applications related to treatment of vascular injuries and vascular scarring (e.g., restenosis), and applications related to chronic inflammatory diseases of the vascular wall.

Without wishing to be bound by theory, acute inflammation does not resolve in a passive fashion. Instead, "resolution-deficit" is a possible mechanism in the healing response of subject to vascular injury and/or scarring, including restenosis and chronic and subacute inflammatory diseases, such as atherosclerosis. The subject pro-resolving lipid mediators may act by actively resolving chronic and acute inflammation and terminating inflammation processes. In some cases, the subject pro-resolving lipid mediators exert potent agonist actions on macrophages and vascular endothelial cells that can control the magnitude of the local inflammatory response. Vascular endothelial cells modulate atherosclerosis development and progression via the expression of adhesion molecules that regulate the recruitment of leukocytes to the lesion. The subject pro-resolving lipid mediators may directly act on VSMCs and VECs, and have a broad profile of activity (e.g., reduction in VSMC/VEC pro-inflammatory gene expression and adhesiveness to monocytes, reduction in VSMC/VEC proliferation and migration, etc.) with direct relevance to the vascular injury response and in the development of atherosclerotic lesions in humans. Local delivery of the subject pro-resolving lipid mediators to VSMC/VEC with temporal and spatial control can modulate the extent of pathogenesis of neointimal hyperplasia at a treatment site. As such, the subject pro-resolving lipid mediators find use in accelerating vascular healing and reducing restenosis and inflammation.

Before certain embodiments are described in greater detail, it is to be understood that this disclosure is not limited to the certain embodiments described, as such may, of course, vary. It is also to be understood that the terminology used herein is for the purpose of describing particular embodiments only, and is not intended to be limiting, since the scope of the disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the embodiments described herein, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Pro-Resolving Lipid Mediators

Aspects of the disclosure relate to the use of pro-resolving lipid mediators in modulating vascular disorders. Pro-resolving lipid mediators are hydroxylated fatty acid compounds that modulate biological activities of VSMCs and VECs and modulate inflammation of vascular walls. A variety of pro-resolving lipid mediators and their therapeutically stable analogues find use in the subject methods, as disclosed herein. In certain cases, the pro-resolving lipid mediators are resolvins (or resolution phase interaction products), lipoxins, protectins, neuroprotectins or maresins.

The subject pro-resolving lipid mediators may be derived from an omega-3 polyunsaturated fatty acid and omega-6 polyunsaturated fatty acids, or may be analogues of the omega-3 polyunsaturated fatty acid and omega-6 polyunsaturated fatty acids. As used herein, the terms "derivative" and "derived from" refers to lipid mediator compounds that could be produced from a fatty acid of interest (e.g., an omega-3 polyunsaturated fatty acid and omega-6 polyunsaturated fatty acids), e.g., via any convenient chemical or enzymatic reaction. Alternatively, the lipid mediator could be an analogue of the fatty acid of interest, such as a hydroxylated analog having a related structure with a desired arrangement of hydroxyl and alkenyl groups. As such, the lipid mediator compounds share an underlying scaffold with the fatty acid from which it is derived from or is an analogue of. Both naturally occurring and non-naturally occurring derivatives and analogues, including aspirin triggered epimers are encompassed by the subject pro-resolving lipid mediators. In some cases, the pro-resolving lipid mediators are hydroxylated derivatives of omega-3 polyunsaturated fatty acids and omega-6 polyunsaturated fatty acids such as, but not limited to, eicosapentaenoic acid (EPA) and docosahexaenoic acid (DHA). In certain cases, the pro-resolving lipid mediators are di- or tri-hydroxylated derivatives of EPA or DHA. In some cases, the pro-resolving lipid mediators are derived from DHA. In other cases, the pro-resolving lipid mediators are derived from EPA.

The pro-resolving lipid mediators may be utilized as a free fatty acid, or alternatively, as a prodrug thereof. Any convenient fatty acid ester versions of the subject pro-resolving lipid mediators may be utilized as prodrugs in the methods described herein. In some cases, the lipid mediator includes a lower alkyl ester of the fatty acid derivative. In certain embodiments, the lower alkyl ester is a methyl or ethyl ester of the fatty acid derivative.

D-series Resolvins

In some instances, the lipid mediator is a D-series resolvin, e.g., a resolvin derived from docosahexaenoic acid (DHA). The terms "DHA" and "docosahexaenoic acid" are used interchangeably herein, and refer to 4,7,10,13,16,19-docosahexaenoic acid. The numbering convention of the subject fatty acids and pro-resolving lipid mediators is demonstrated by the DHA structure and name, where position C1 is the carbon of the carboxylic acid. DHA is a C22 fatty acid described by the following structure:

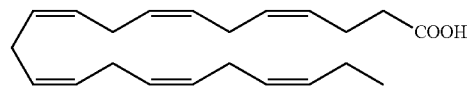

As used herein, the term "D-series resolvin" refers to a compound that is a hydroxylated derivative or analogue of DHA. D-series resolvins may be derived from DHA via any convenient chemistries or chemical reactions, including but not limited to, enzymatic reactions, biosynthetic reactions, metabolic reactions, organic chemical reactions including, hydroxylation reactions, epoxidation reactions, elimination reactions, addition reactions, and epimerizations. Both naturally occurring DHA derivatives and non-naturally occurring analogues of the same are encompassed by the subject D-series resolvins, including aspirin triggered epimers such as the 17R-D series resolvin.

In some cases, the D-series resolvin is a (mono or poly)hydroxy-polyunsaturated fatty acid derivative of DHA or an analogue thereof, such as a compound that includes a C22 carbon chain having a terminal —CH═CH—CH$_2$—CH$_3$ group with a 19-Z configuration. In other cases, the compound has a 19-E configuration. In certain embodiments, the D-series resolvin includes four, five or six double bonds in the C22 carbon chain. In some instances, the C17-C22 terminal of the D-series resolvin is described by the formula —CH(OH)—CH$_2$—CH═CH—CH$_2$—CH$_3$, where the group has a (19-Z) alkene configuration and a 17S configuration. In other instances, the compound has a 17R configuration.

The D-series resolvin may include one or more hydroxyl groups attached to the C22 fatty acid chain, such as two or more, three or more, or four or more hydroxyl groups. In certain instances, the D-series resolvin includes one, two or three hydroxyl groups attached at any convenient positions of the C22 fatty acid chain. In some embodiments, the D-series resolvin is a trihydroxylated derivative of docosahexaenoic acid (DHA). In other embodiments, the D-series resolvin is a dihydroxylated derivative of docosahexaenoic acid (DHA). In another embodiment, the D-series resolvin is a monohydroxylated derivative of DHA, such as 17(S)- or 17(R)-HDHA. In certain embodiments, the D-series resolvin is an epoxide derivative of DHA. In certain embodiments, the D-series resolvin includes a keto group, e.g., a derivate of a (poly)hydroxylated DHA derivative (e.g., as described herein) where any convenient hydroxyl group has been oxidized to a keto group.

The D-series resolvin may be described by formula (I):

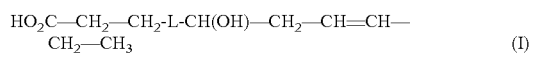

where L is a linear C13 hydrocarbon chain comprising five —CH=CH— groups; and three groups independently selected from: —CH$_2$—, —(C=O)— and —CH(OH)—; where the C17 center may be racemic, or have a 17R or a 17S configuration; where the resolvin has a 19-Z or a 19-E configuration; and where each of the five —CH=CH— groups has independently a E- or a Z-configuration.

In some cases, the D-series resolvin is hydroxylated at the C17 position and has a 17(S) configuration. In other cases, the C17 center has a 17(R) configuration. In some instances, in formula (I), the C17-C22 terminal of the D-series resolvin is described by the formula —CH(OH)—CH$_2$—CH=CH—CH$_2$—CH$_3$, where the group has a (19-Z) alkene configuration. In other instances, the alkene configuration is 19-E.

In some embodiments, in formula (I), when one or more (e.g., 2 or more, 3 or more, or 4 or more) (e.g., 1, 2, 3, 4 or 5) of the five —CH=CH— groups is present at a position selected from the 4, 7, 10, 13 or 19 positions, the —CH=CH— groups at those positions each have a Z-configuration.

In some embodiments, in formula (I), when one or more (e.g., 2 or more, 3 or more, or 4 or more) (e.g., 1, 2, 3, 4 or 5) of the five —CH=CH— groups is present at a position selected from the 5, 6, 8, 9, 11, 12 or 14 positions, the —CH=CH— groups at those positions each have an E-configuration.

In some embodiments, in formula (I), L includes two —CH(OH)— groups and one —CH$_2$— group.

In some embodiments, in formula (I), L includes three —CH=CH— groups in the E-configuration and two —CH=CH— groups in the Z-configuration.

In some embodiments, in formula (I), L includes the following group:

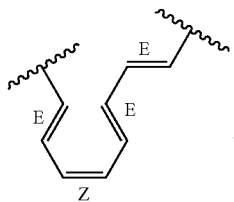

In some instances, L includes a conjugated triene group (e.g., —CH=CH—CH=CH—CH=CH—), where the alkenyl groups are arranged in any convenient combination of E- and Z-configurations, such as EEZ, EEE, EZE, EZZ, and ZZZ, where the triene group may be included in the fatty acid chain in either orientation (i.e., EEZ=ZEE).

In some embodiments, in formula (I), L includes four —CH=CH— groups in the E-configuration and one —CH=CH— group in the Z-configuration.

In some embodiments, in formula (I), L includes one —CH(OH)— group and two —CH$_2$— groups.

In some embodiments, in formula (I), L comprises two —CH=CH— groups in the E-configuration and three —CH=CH— groups in the Z-configuration.

In some embodiments, in formula (I), L include one, two or three hydroxyl groups located at positions selected from positions 4, 5, 7, 8, 10, 11 and 16. In some embodiments, in formula (I), L includes a —CH(OH)— group located at position 4, 5, 7, 8, 10, 11 or 16 that has a R configuration.

In some embodiments, in formula (I), L includes a —CH(OH)— group located at position 4, 5, 7, 8, 10, 11 or 16 that has a S configuration. In certain embodiments, L includes a (4S)—CH(OH)— group. In certain embodiments, L includes a racemic —CH(OH)— group at position 5. In certain embodiments, L includes a (7S)—CH(OH)— group. In certain embodiments, L includes a (8R)—CH(OH)— group. In certain embodiments, L includes a racemic —CH(OH)— group at position 10 or position 11. In certain embodiments, L includes a (16R)—CH(OH)— group.

In some embodiments, in formula (I), L comprises a C13 divalent group that is the same as the that part of the structure encompassed by C4-C16 of a D-series resolvin.

In certain embodiments, in formula (I), L is described by that part of the structure encompassed by C4-C16 of one of RvD1, RvD2, RvD3, RvD4, RvD5 and RvD6, as described in the structures below.

In certain embodiments, the D-series resolvin is selected from RvD1, RvD2, RvD3, RvD4, RvD5, RvD6. In some cases, the D-series resolvin is RvD1. In other cases, the D-series resolvin is RvD2.

In some embodiments, the D series resolvin is a 17R or 17S resolvin of the D-series, for example but not limited to, 17R-diH DHA; 16,17R-diH DHA; 17R-H(p) DHA; 7(8)-epoxy-17R-DHA; 4(5)-epoxy-17R-H DHA; Resolvin D1 (17S,8,17R-triDHA); resolvin D2 (17S,16,17-triDHA); Resolvin D3 (4S,11,17R-triDHA); Resolvin D4 (4S,5,17-triDHA), 7S,17S-dihydroxy-docosa-5Z,8E,10Z,13Z,15E,19Z-hexaenoic acid.

In certain embodiments, the D-series resolvin is described by one of the following structures:

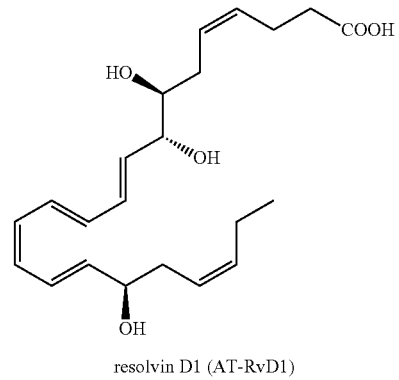

resolvin D1 (AT-RvD1)

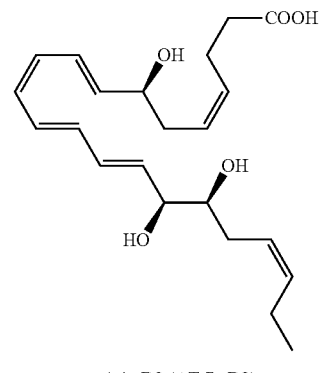

resolvin D2 (AT-RvD2)

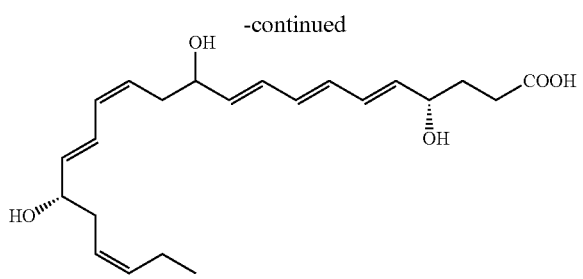

resolvin D3 (RvD3)

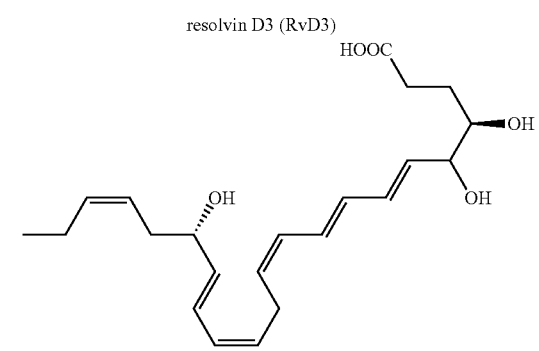

resolvin D4 (RvD4)

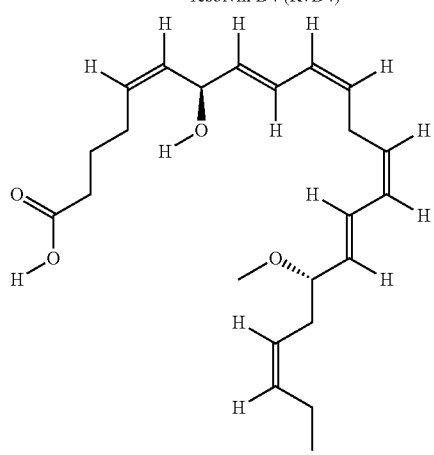

RvD5

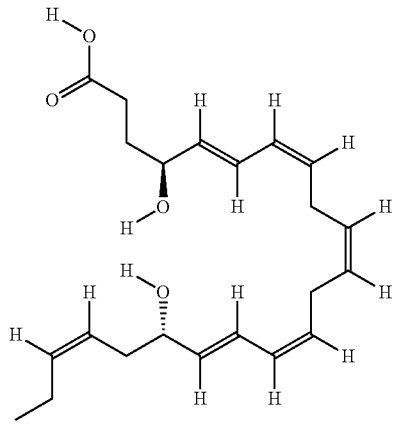

RvD6

E-series Resolvins

In some instances, the lipid mediator is an E-series resolvin, e.g., a resolvin derived from eicosapentaenoic acid (EPA). Any convenient E-series resolvin may be utilized in the subject methods. In some embodiments, the lipid mediator is a hydroxylated derivative of eicosapentaenoic acid (EPA) that is an E-series resolvin or a 18R resolvin of the E series, for example but not limited to resolvin E1 (RvE1; (5S,12R,18R-trihydroxy-6Z,8E,10E,14Z,16E-eicosapentaenoic acid); 19-(p-fluorophenoxy)-RvE1; 18-oxo-RvE1; 5S,6R-epoxy, 18R-hydroxy-EPE, Resolvin E2 (RvE2, 5S,18R-dihydroxy-6E,8Z,11Z,14Z,16E-eicosapentaenoic acid). The terms "EPA" and "eicosapentaenoic acid" are used interchangeably herein.

In some instances, the E-series resolvin is selected from: 18S-Resolvin E1 (5S,12R,18S-trihydroxy-6Z,8E,10E,14Z,16E-eicosapentaenoic acid); 19-hydroxy-Resolvin E1 (5S,12R,18S,19-tetrahydroxy-6Z,8E,10E,14Z,16E-eicosapentaenoic acid); 20-hydroxy-Resolvin E1 (5S,12R,18S,20-tetrahydroxy-6Z,8E,10E,14Z,16E-eicosapentaenoic acid)

Maresins

In certain embodiments, the pro-resolving lipid mediator may be a maresin, macrophage mediator in resolving inflammation. Maresins are derived from DHA. In certain cases, the maresin used in the subject methods and compositions may be derived from 14-hydro(peroxy)-docosahexaenoic acid (14-HpDHA), as described in Dalli J. et al. (FASEB J., July 2013, 27: 2573-2583).

In certain instances, the maresin may be MaR1, maresin 1 (7, 14-dihydroxy DHA).

In certain cases, MaR1 may be 7R,14S-dihydroxydocosa-4Z,8E,10E,12Z,16Z,19Z-hexaenoic acid (7R MaR1). The structure of 7R MaR1 is depicted below.

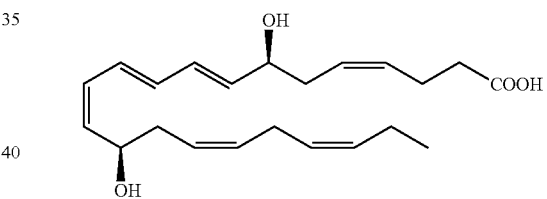

In other cases, MaR1 may be 7S,14R-dihydroxydocosa-4Z,8E,10Z,12Z,16Z,19Z-hexaenoic acid (7S MaR1). The structure of 7S MaR1 is as follows.

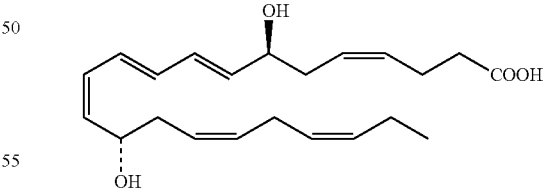

In certain cases, the pro-resolving lipid mediator may be a precursor of MaR1. In certain instances, the precursor of MaR1 useful in the subject methods and compositions may be 13,14-epoxy-maresin (13,14-eMaR or 13S,14S-epoxy-docosa-4Z,7Z,9E,11E,16Z,19Z-hexaenoic acid (13 S,14S-epoxy-DHA)). 13,14-eMaR is described in Dalli J. et al. (FASEB J., July 2013, 27: 2573-2583). The structure of 13,14-eMaR is provided in Dalli J. et al and is reproduced below.

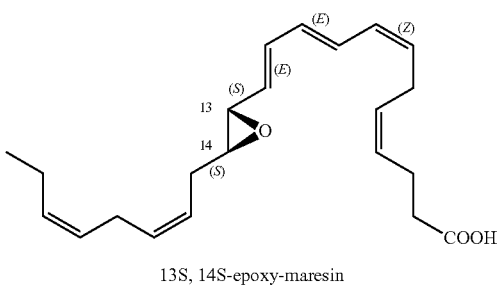

13S, 14S-epoxy-maresin

In certain embodiments, maresin or a derivative or precursor thereof may be derived from DHA via any convenient chemistries or chemical reactions, including but not limited to, enzymatic reactions, biosynthetic reactions, metabolic reactions, organic chemical reactions including, hydroxylation reactions, epoxidation reactions, elimination reactions, addition reactions, and epimerizations. Both naturally occurring maresins and non-naturally occurring maresins, such as, functional analogs of maresin are encompassed by the subject maresins.

Protectins

Protectin, or neuroprotectins (used interchangeably herein) are oxygenated metabolites of DHA that comprise conjugated triene structures, or docosatrienes (DT). Any convenient protectins may be utilized in the subject methods. In some embodiments, a protectin useful in the methods as disclosed herein is a di- or tri-hydroxy derivative of DHA including, but not limited to, neuroprotectin D1 (NPD1); protectin D1 (PD1); 10,17s-docosatriene or analogues and mimetics of NPD1; PD1 or 10,17s-docosatriene. Further protectins of interest include, but are not limited to, those described in International Application No. WO 04/014835, the contents of which are incorporated herein by reference in their entirety. In certain embodiments, the lipid mediator is described by the following structure:

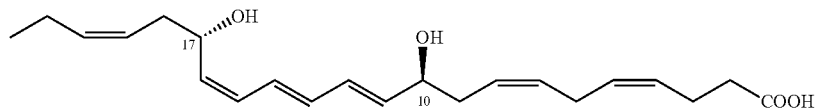 [SMILES: CC/C=C\C[C@H](O)\C=C/C=C/C=C/[C@@H](O)C/C=C\C/C=C\CCC(=O)O]

Lipoxins

In some embodiments, the lipid mediator is a lipoxin. Any convenient lipoxins may be utilized in the subject methods. Lipoxin compounds of interest include, but are not limited to, those compounds described in US2011/0190242. In some embodiments, the lipoxin compounds are described by one of formulae 51, 52, 53 or 54:

(51)

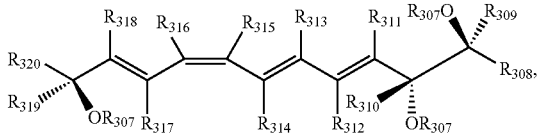

(52)

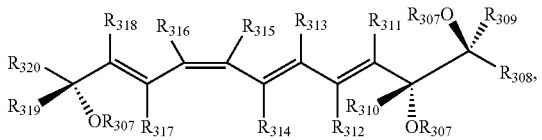

(53)

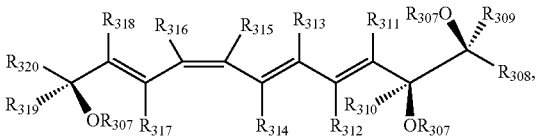

(54)

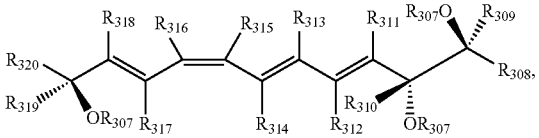

where: each $R_{307}$ is independently selected from hydrogen and straight, branched, cyclic, saturated, or unsaturated alkyl having from 1 to 20 carbon atoms; $R_{308}$, $R_{309}$, $R_{310}$, $R_{319}$, and $R_{320}$ are independently selected from: (a) hydrogen; (b) straight, branched, cyclic, saturated, or unsaturated alkyl having from 1 to 20 carbon atoms; (c) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; (d) substituted aryl or heteroaryl, wherein the aryl or heteroaryl is substituted with one or more substituents selected from alkyl, cycloalkyl, alkoxy, halo, aryl, heteroaryl, carboxyl, and carboxamido; and (e) Z—Y, wherein: Z is selected from a straight, branched, cyclic, saturated, or unsaturated alkyl having from 1 to 20 carbon atoms; substituted lower alkyl, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; and substituted aryl or heteroaryl, wherein the aryl or heteroaryl is substituted with one or more substituents selected from alkyl, cycloalkyl, alkoxy, halo, aryl, heteroaryl, carboxyl, and carboxamido; and Y is selected from hydrogen; alkyl; cycloalkyl; carboxyl; carboxamido; aryl; heteroaryl; substituted aryl or heteroaryl, wherein the aryl or heteroaryl is substituted with one or more substituents selected from alkyl, cycloalkyl, alkoxy, halo, aryl, heteroaryl, carboxyl, and carboxamido; and $R_{311}$ to $R_{318}$ are independently selected from: (a) hydrogen; (b) halo; (c) straight, branched, cyclic, saturated, or unsaturated alkyl having from 1 to 20 carbon atoms; (d) substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; (e) substituted aryl or heteroaryl, wherein the aryl or heteroaryl is substituted with one or more substituents selected from alkyl, cycloalkyl, alkoxy, halo, aryl, heteroaryl, carboxyl, and carboxamido; or $R_{308}$ to $R_{320}$ are independently a bond that forms a carbon-carbon double bond, a carbon-carbon triple bond, or a ring with the lipoxin backbone; or any two of $R_{307}$ to $R_{320}$ are taken together with the atoms to which they are bound and optionally to 1 to 6 oxygen atoms, 1 to 6 nitrogen atoms, or both 1 to 6 oxygen atoms and 1 to 6 nitrogen atoms, to form a ring containing 3 to 20 atoms; as those group are defined in US2011/0190242.

In certain embodiments, the lipoxin is selected from: lipoxin A4 (LXA4, 5,6,15-trihydroxy-7,9,11,13-eicosatetraenoic acid); lipoxin B4 (5,14,15-trihydroxyicosa-6,8,10,12-tetraenoic acid); 5S,6R,15R-trihydroxyl-7E,9E,13E,11z-eicosatetraenoic acid; lipoxin C4 (5,15-dihydroxy-6-S-glutathionyl-7,9,13,11-eicosatetraenoic acid); lipoxin D4 (5S,15S-dihydroxy-6R-(S-cysteinylglycinyl)-7E,9E,11Z, 13E-eicosatetraenoic acid); lipoxin E4 ((5S,6R,7E,9E,11Z, 13E,15S)-6-{[(2R)-2-amino-2-carboxyethyl]sulfanyl}-5, 15-dihydroxyicosa-7,9,11,13-tetraenoic acid); lipoxin B5 (6,8,10,12,17-Eicosapentaenoic acid, 5,14,15-trihydroxy-, (5S-(5R*,6E,8Z,10E,12E,14R*,15R*,17Z))—); lipoxin A5 ((5S-(5R*,6R*,7E,9E,11Z,13Z,15R*,17Z))-5,6,15-Trihydroxy-7,9,11,13,17-eicosapentaenoic acid).

Pro-resolving lipid mediators of interest include, but are not limited to: 7S,14S-dihydroxy-docosa-4Z,8E,10E,12Z, 16Z,19Z-hexaenoic acid (maresin 1), compounds such as those disclosed in WO06/06075457, WO04/014835, WO05/105025, US20110190242, US2010/0105773, US2005/0238589, US2006/0293288, US2005/0238589, US2005/0261255 and US2004/0116408, and Serhan et al. "Resolving inflammation: dual anti-inflammatory and pro-resolution lipid mediators" Nature Reviews Immunology 8, 349-361 (May 2008), the disclosures of which are incorporated herein in their entirety by reference.

The subject pro-resolving lipid mediators, or their pharmaceutically acceptable salts may contain one or more asymmetric centers and may thus give rise to enantiomers, diastereomers, geometric isomers, individual isomers and other stereoisomeric forms that may be defined, in terms of absolute stereochemistry, as (R)- or (S)-. The present invention is meant to include all such possible isomers, as well as, their racemic and optically pure forms. Optically active (+) and (−), and (R)- and (S)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Vascular Devices

As summarized above, also provided by the present disclosure are lipid mediator-containing vascular devices. The vascular devices find use in the local delivery of pro-resolving lipid mediators to the site of a vascular disorder or injury. Local delivery to the treatment site may be achieved with spatial and/or temporal control utilizing the subject lipid mediator-containing vascular devices. Any convenient vascular devices may be utilized in the subject compositions and methods. As used herein "vascular device" refers broadly to any device that is deployed in or adjacent to a suitable body lumen (e.g., blood vessels, arteries, veins or grafts) of a patient. The device may be suitable for intraluminal delivery or implantation. The device may be permanently or temporarily implanted into a subject. A variety of medical implants, devices and drug delivery systems may be adapted for use in the subject methods as vascular devices. Vascular devices of interest include, but are not limited to drug-eluting stents, vascular grafts, perivascular wraps, polymeric matrices and thin film implants. Medical implants, devices and drug delivery systems that may be adapted for use in the subject lipid mediator-containing vascular devices include, but are not limited to, those implants, devices and drug delivery systems described in US2012/0150283, US2012/0116305, US 2012/0108959, US2012/0015019, US2012/0060969, US2010/0331819, US2009/0285873, US2009/0053392, and US2009/0216317, the disclosures of which are herein incorporated by reference in their entirety.

In some cases, the lipid mediator-containing vascular device is placed adjacent to a body lumen (arteries, veins or grafts) and a therapeutically effective amount of the lipid mediator is delivered into the arteries, veins or grafts.

The vascular device may provide for controlled delivery of a lipid mediator to the treatment site. In some cases, the vascular device is provided having a component that is loaded with a lipid mediator that is associated with a component (e.g., a hydration inhibitor) to control the delivery of the compound in the subject. In some instances, the vascular device provides for substantially uniform delivery of the lipid mediator to the treatment site.

The vascular devices may include a reservoir of lipid mediator and optionally one or more biological agents. The reservoir is contained within the device, such that upon implantation, the lipid mediator is subsequently eluted from the device into the surrounding tissue of a subject.

In general, the vascular device will elute the lipid mediator to the surrounding tissue upon placement of the device in a patient for a period ranging from about 2 minutes to about 3 months or more, including 5 minutes to about 14 weeks, such as 10 minutes, 30 minutes, 60 minutes, 100 minutes, 130 minutes, 200 minutes, about 6 hours, about 12 hours, about 24 hours, 72 hours, about 3 days, about 7 days, about 2 weeks, about 3 weeks, about 4 weeks, about 6 weeks, about 8 weeks, about 12 weeks, or more. The lipid mediator agent may be released from the first reservoir and an optional additional bioactive agent may be released from a second reservoir over a similar period of time or over different periods of time.

In some embodiments, the vascular device utilizes a lipid mediator (and/or optional bioactive agent) in a dry lyophilized form, packaged within the device and subsequently re-solubilized in situ for release into the surrounding tissue following implantation. For example, after insertion into a blood vessel, lyophilized bioactive agent is sequestered within the device, restricted from the vascular environment within the reservoir, maintaining bio-activity for months, where rehydration and release are controlled via engineered pores (e.g., in a nanoporous thin film and/or a microporous thin film). In such embodiments, the stability and bioactivity of lipid mediator in the reservoir is maintained for an extended period of time after implantation.

Such vascular devices can comprise one or more components. For purposes of illustration and not limitation, examples of such devices include stents, grafts, stent-grafts, valves, filters, coils, staples, sutures, guidewires, catheters, catheter balloons, and the like. In one embodiment, the component is an interventional component having a first cross-sectional dimension for the purpose of delivery and a second cross-sectional dimension after deployment, and can be deployed by known mechanical techniques including balloon expansion deployment techniques, or by electrical or thermal actuation, or self-expansion deployment techniques, as well known in the art. For example, and as embodied herein, representative embodiments of a stent, stent-graft or similar interventional component are disclosed in U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, which are all incorporated herein by reference. It is recognized, however, that the interventional component can be any type of implantable or deployable component for a vascular device capable of being loaded with lipid mediator.

It should be appreciated that the vascular devices may be utilized in any part of the vasculature including neurological, carotid, coronary, renal, aortic, iliac, femoral, or other peripheral vasculature. As used herein, an "implantable vascular device" refers to any construct that is totally or partly introduced, surgically or medically, into a patient's body or by medical intervention into a natural orifice, and which is intended to remain in place until the device biodegrades.

Drug-eluting Stents

Vascular devices that find use in delivering the subject pro-resolving lipid mediators include drug-eluting stents. As used herein, a "stent" refers generally to any device used to hold tissue in place in a patient's body. The term "stent" is intended to include, but is not limited to, self-expandable stents, balloon-expandable stents, stent-grafts, and grafts. Stents of interest include those used for the maintenance of the patency of a vessel in a patient's body when the vessel is narrowed or closed due to diseases including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. A stent can be used in, without limitation, neuro, carotid, coronary, pulmonary, aorta, renal, biliary, iliac, femoral and popliteal arteries as well as other peripheral vasculatures.

Any convenient drug-eluting stents may be utilized in the subject methods. Drug eluting stents (DES) which release a variety of therapeutic agents at the site of stent placement have been in use for some time. To date these stents comprised delivery interfaces (lengths) that are less than 40 mm in length and, in any event, have delivery interfaces that are not intended, and most often do not, contact the luminal surface of the vessel at the non-afflicted region at the periphery of the afflicted region. In some cases, the vascular devices of interest includes a drug-eluting stent such as a stent that is described in US2012/0060969, US2010/0222875, US2012/0015019, US2009/0285873, or US2009/0053392; or by Acharya and Park, "Mechanisms of controlled drug release from drug-eluting stents", Advanced Drug Delivery Reviews, Volume 58, Issue 3, 3 Jun. 2006, Pages 387-401; the disclosures of which are herein incorporated by reference in their entirety.

The structure of the stent can be of virtually any design. A stent, for example, may include a pattern or network of interconnecting structural elements or struts. In general, a stent is composed of a scaffolding that includes a pattern or network of interconnecting structural elements or struts. The scaffolding can be formed of tubes, or sheets of material rolled into a cylindrical shape. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a body lumen. A medicated stent may be fabricated by coating the surface of either a metallic or polymeric scaffolding with a polymeric carrier that includes a bioactive agent. The polymeric scaffolding may also serve as a carrier of bioactive agent.

The drug-eluting stent includes a structural component and a drug-containing matric component. Various metals or alloys may be used in forming the stent structure of a drug-eluting stent delivery system include stainless steel, platinum, titanium, tantalum, nickel-titanium, cobalt-chromium, and alloys thereof. Examples of various polymers used in forming the drug-eluting component of the drug-eluting stent delivery system (e.g., polymer coat layer) include poly(methyl methacrylate) (PMMA), poly(ethylene-co-vinyl alcohol) (EVAL), poly(butyl methacrylate) (PBMA), biodegradable polymers (e.g., polyglycolic acid (PGA) and poly(L-lactic acid) (PLLA)), copolymers and blends thereof.

The drug eluting stents may use biocompatible and/or biodegradable coatings for lipid mediator release. In such instances, a biodegradable drug release coating may be applied over a biocompatible coating such as protoelastin covalently bound by plasma polymerization. This would allow local elution of a lipid mediator, leaving behind a stent with a biocompatible coating.

The drug-eluting stent may be selected so as to provide for a desired "release profile" of the lipid mediator. A drug release profile, or release profile therefore informs one of such things as the predictability of the release rate, variation, if any, in the release rate over time or on a per unit area basis across a drug-eluting surface. The calculation of dosages, dosage rates and appropriate duration of treatment are previously known in the art. Furthermore, the therapeutic drugs or agents are loaded at desired concentration levels per methods well known in the art to render the device ready for implantation.

In use, the stent is deployed using conventional techniques. The drug-eluting stent can be readily delivered to the desired body lumen, such as a coronary or carotid artery (peripheral vessels, etc.), by mounting the drug-eluting stent on an expandable member of a delivery catheter, for example a balloon, and advancing the catheter and drug-eluting stent assembly through the body lumen to the target site.

Delivery and deployment of a stent are accomplished by positioning the stent at one end of a catheter, inserting the end of the catheter through the skin into a body lumen, advancing the catheter in the body lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand. This requires a sufficient degree of strength and rigidity or stiffness. In addition to having adequate radial strength, the stent should be longitudinally flexible to allow it to be maneuvered through a tortuous vascular path.

Once in position, the lipid mediator gradually diffuses into adjacent tissue at a rate dictated by the parameters associated with the polymer coat layer of the stent. The total dosage that is delivered is of course limited by the total amount of the lipid mediator that had been loaded within the polymeric conformal coating or other component of the drug-eluting stent. The lipid mediator is selected to treat the deployment site and/or locations downstream thereof. For example, deployment in the carotid artery will serve to deliver such lipid mediator to the local arterial tissue.

Other devices which may be adapted for use in the subject vascular devices include balloon expandable stents, self-expanding stents, grafts, stent-grafts, balloons, and catheters.

Thin Film Implants

In some cases, the vascular device is a thin film implant. Any convenient thin film polymer matrices may be utilized in the subject methods to provide an implant that is capable of locally delivering a lipid mediator to a treatment site. As used herein, the terms "thin film polymer matrix" and "thin film implant" are used interchangeably. In some embodiments, the vascular device is a thin film polymer matrix. The thin film polymer matrices may be adapted for implanting with any convenient structure or configuration, e.g., as a perivascular wrap.

Thin film polymer matrices of interest that may be adapted for use in the subject thin film implants include, but are not limited to, those described Desai et al., entitled "Multilayer Thin Film Drug Delivery Device and Methods of Making and Using the Same" International Application No. PCT/US2012/033366, and U.S. Provisional Application Ser. No. 61/475,373, filed Apr. 14, 2011, the disclosures of which are herein incorporated by reference in their entirety. Other devices of interest suitable for adapting for use in the subject vascular devices include, but are not limited to, those described Desai et al., entitled "Bioactive Agent Delivery Devices and Methods of Making and Using the Same", U.S. Provisional Application Ser. No. 61/653,119, filed May 30, 2012, the disclosure of which is herein incorporated by reference in its entirety. Further thin film polymer matrices of interest suitable for adapting for use in the subject vascular implants include, but are not limited to, those described in US2012/0114734, US2010/0318193, the disclosures of which are herein incorporated by reference in their entirety.

In the thin film implants, the reservoir is defined by a continuous layer of a composition that includes the lipid mediator. The reservoir of lipid mediator may be positioned between a first thin film layer, and a second thin film (e.g., a nonporous thin film), where the first layer may be a thin film that includes a biodegradable polymer and a pore forming agent, or a microporous thin film from which the pore forming agent has dissolved. In certain embodiments, a third nanoporous thin film layer is positioned between the first layer and the reservoir of bioactive agent. In some cases, the reservoir is defined by a plurality of structures in a thin film layer, such as but not limited to, wells, pores, chambers or channels located through and/or across a surface of the thin film, where the structural voids are filled with a composition that includes the bioactive agent. In such embodiments, the reservoir defined by the plurality of structures may be covered with a further thin film that provides a porous layer upon implantation through which the lipid mediator can diffuse (e.g., a nanoporous thin film, a microporous thin film or precursor thereof, or a combination thereof). In such cases, this reservoir defined by the plurality of structures may be described as being positioned between a first thin film layer and a second thin film layer.

The pore forming agent may protect the lipid mediator from degradation by sealing and maintaining the lipid mediator in the implant in a lyophilized state. In some embodiments, dissolution of the pore forming agent provides for an elution profile of the bioactive agent to the surrounding tissue upon placement of the implant in a subject (e.g., a delayed elution profile, two elution profiles, a substantially zero order elution profile).

The thin film polymer matrices may form any convenient structure, such as but not limited to, a furled or an unfurled structure, a folded structure, a tubular structure, a planar structure, a toric structure or a discoid structure.

In certain instances, the thin film polymer matrix is furlable. A furled thin film polymer matrix finds use in methods that further include unfurling the thin film polymer matrix. In some embodiments, the thin film implants form either a furled or an unfurled structure. As used herein, the term "furled" refers to a structure of a material where the material is curled or rolled upon itself (e.g., the structure is an annular sheet disposed about a central axis) as compared to a substantially planar, flat or "unfurled" structure of the material. The term "furling" refers to the process of transforming a material from an unfurled structure to a furled structure (e.g., whereby a flat sheet curls around a central axis to form an annular structure). The term "unfurling" refers to the reverse process where the thin film is unrolled, unfolded, or spread out. Application of suitable furling or unfurling conditions to a thin film implant can result in transformation to produce a desired furled or unfurled structure, respectively. A multilayer thin film implant structure of the present disclosure may spontaneously furl or unfurl in response to suitable conditions. For example, drying conditions sufficient to furl the subject implant and produce a furled structure. Alternatively, contact of a furled multilayer thin film structure with a hydrating liquid (e.g., vitreous fluid present in the eye of a subject), produces a substantially planar unfurled structure. In some cases, upon implantation and contact with a hydrating liquid, the thin film implant expands. By "expands" is meant that the thin film becomes larger in size or volume as a result of the surrounding liquid hydrating the film.

In certain embodiments, the furled structure is substantially cylindrical, e.g., a structure where a planar film has curled upon itself to form a cylindrical shape. In certain embodiments, the furled structure is substantially frusto-conical. By frusto-conical is meant a structure having the shape of a frustum of a cone, i.e., the shape of a cone whose tip has been truncated by a plane parallel to its base. In certain embodiments, the implant has an unfurled structure that includes a substantially circular peripheral edge.

In some embodiments, the thin film implants are fabricated to have a diameter of between about 1 mm and about 50 mm, such as between about 1 mm and about 10 mm, between about 2 mm and about 8 mm, between about 3 mm and about 7 mm, between about 4 mm and about 6 mm. In some cases, the diameter is about 1 mm, about 2 mm, about 3 mm, about 4 mm, about 5 mm, about 6 mm, about 7 mm, about 8 mm, about 9 mm or about 10 mm. In some embodiments, the thin film implants are fabricated to have an area between about 1 $mm^2$ and about 100 $mm^2$, including between about 4 $mm^2$ and about 64 $mm^2$, between about 9 $mm^2$ and about 49 $mm^2$, between about 16 $mm^2$ and about 36 $mm^2$, such as about 16 $mm^2$, about 25 $mm^2$, or about 36 $mm^2$.

In some embodiments, the thin film is fabricated to have a thickness between about 1 μm and about 1 mm, such as between about 10 μm and about 500 μm, between about 50 μm and about 300 μm, between about 100 μm and about 200 μm, such as about 100 μm, about 125 μm, about 150 μm, about 175 μm or about 200 μm.

Polymeric Matrices

Drug-containing polymeric matrices of the subject vascular devices (e.g., drug-eluting stents or thin film implants) can be fabricated from a variety of suitable polymeric materials, including biodegradable polymeric materials. A variety of polymeric matrices may be utilized in the subject vascular devices. In some embodiments, the subject implants are biodegradable, e.g., include a biodegradable polymer. Biodegradable polymers of interest include, but are not limited to, biodegradable or bioerodible polymers, such as poly(DL-lactide-co-glycolide) (PLGA), poly(DL-lactide-co-ε-caprolactone) (DLPLCL), poly(ε-caprolactone) (PCL), or combinations thereof, as well as natural biodegradable polymers, such as collagen, and the like. PLGA is a bulk-eroding copolymer of polylactide (PLA) and polyglycolide (PGA). In some embodiments, the biodegradable polymer includes PLA, PGA, PCL, PLGA, or PLCL.

In some embodiments, the biodegradable polymer includes polycaprolactone (PCL). PCL is an exemplary polymer that is biocompatible and biodegradable in vivo and well tolerated throughout the duration of its implantation and degradation.

In some cases, the biodegradable polymer has a MW of about 80 kDa or more and does not degrade until after 1 year or more in the tissue of a subject. In some embodiments, the macroscopic degradation of a biodegradable polymer (e.g., PCL) may occur at about 8 kDa. In some embodiments, the MW of the biodegradable polymer is selected so as to tune the degradation time of the material in vivo. For example, a PCL polymer of about 15 to about 20 kDa may start to structurally break down after 4 months and lose mechanical integrity by 6 months.

Methods

As summarized above, methods of modulating healing response to vascular injury and/or vascular scarring are provided. Methods of modulating restenosis of a vascular wall are provided. Methods of modulating inflammation of a vascular wall are provided. As such, aspects of the disclosure include contacting the vascular wall with a lipid mediator (e.g., as described herein), in an amount sufficient to modulate inflammation and/or restenosis at the vascular wall. Also provided are methods of modulating one or more biological activities of a vascular smooth muscle cell (VSMC) and vascular endothelial cells (VEC). As such, aspects of the disclosure include contacting the VSMC and/or VEC with a lipid mediator (e.g., as described herein), in an amount sufficient to modulate the one or more biological activities of the VSMC and/or VEC.

In some embodiments, the method is a method of modulating a biological activity of a VSMC and/or VEC in a sample, the method comprising contacting the sample with an effective amount of a lipid mediator to modulate the biological activity of the VSMC and/or VEC. In certain embodiments, the modulating the biological activity is inhibiting proliferation of the VSMC and/or VEC. In certain embodiments, the modulating the biological activity is inhibiting migration of the VSMC and/or VEC. In certain embodiments, the modulating the biological activity is inhibiting monocyte adhesion to the VSMC and/or VEC. In certain embodiments, the modulating the biological activity is reducing expression of a pro-inflammatory gene in the VSMC and/or VEC.

Any convenient protocol for contacting the lipid mediator with the vascular wall or VSMC and/or VEC may be employed. The particular protocol that is employed may vary, e.g., depending on whether the sample is in vitro or in vivo. The term "sample" as used herein relates to a material or mixture of materials, typically, although not necessarily, in fluid form, containing one or more components of interest, including but not limited to a vascular wall, and VSMCs and/or VECs. For in vitro protocols, contact of the lipid mediator with the sample may be achieved using any convenient protocol. In some instances, the sample includes cells that are maintained in a suitable culture medium, and the lipid mediator is introduced into the culture medium. For in vivo protocols, any convenient administration protocol may be employed. Depending upon the potency of the lipid mediator, the response desired, the manner of administration, the half-life, the number of cells present, various protocols may be employed.

The subject methods include administering a therapeutically effective amount of a lipid mediator to a subject to treat a vascular disease or injury.

A "therapeutically effective amount" refers to that amount of the lipid mediator that will have a beneficial effect, which may be curative or palliative, on the health and well-being of the patient with regard to the vascular disease or injury with which the subject is known or suspected to be afflicted. As used herein, the terms "host", "subject", and "patient" are used interchangeably. A therapeutically effective amount may be administered as a single bolus, as intermittent bolus charges, as short, medium or long term sustained release formulations or as any combination of these. As used herein, short-term sustained release refers to the administration of a therapeutically effective amount of a lipid mediator over a period from about several hours to about 3 days. Medium-term sustained release refers to administration of a therapeutically effective amount of a lipid mediator over a period from about 3 day to about 14 days and long-term refers to the delivery of a therapeutically effective amount over any period in excess of about 14 days, e.g., one month or longer. Any reference a lipid mediator relating to its presence on an implantable vascular device or its use in a method of this invention is to be understood as referring to a therapeutically effective amount of that lipid mediator.

The actual delivered dose necessary to achieve a therapeutically effective amount will be readily determinable by those of ordinary skill in the art based on the disclosures herein without undue experimentation.

As used herein, "treating" refers to the administration of a therapeutically effective amount of a lipid mediator to a subject known or suspected to be suffering from a vascular disease.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a lipid mediator, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery, or loss of organ function if the artery is peripheral.

"Restenosis" refers to the re-narrowing or blockage of an artery at or near the site where angioplasty or another surgical procedure was previously performed to remove a stenosis. It is generally due to smooth muscle cell proliferation and, at times, is accompanied by thrombosis. Stent placement sites are also susceptible to restenosis due to abnormal tissue growth at the site of implantation. This form of restenosis tends also to occur at 3 to 6 months after stent placement but it is not affected by the use of anti-clotting drugs.

Also provided is a method of localized delivery of a lipid mediator to a cell, vascular wall or tissue. Any convenient methods and vascular devices (e.g., as described herein) for localized delivery may be utilized in the subject methods. Devices of interest include, but are not limited to, vascular devices such as drug-eluting stents, vascular grafts, polymeric matrices, thin film implants, and the like.

The subject methods may further include contacting the vascular wall or VSMA with an additional bioactive agent (e.g., as described herein). In some cases, the additional bioactive agent is selected from an anti-inflammatory agent and an anti-proliferative agent.

In some embodiments, the method includes positioning in a subject a vascular device such as a drug-eluting stent or a thin film implant, e.g., as described above. By "positioning" or "implantation" is meant placing the implant (e.g., placing surgically, injection by syringe or delivery by catheter) in any suitable opening, tissue or body cavity of the subject where local delivery of the lipid mediator is desired. For example, the implant may be injected in a blood vessel of the subject. For example, the implant may be positioned in any convenient space in a tissue mass. In certain instances, the implant may have a furled structure suitable for implantation, e.g., injection by syringe or delivery by catheter.

In certain embodiments, the method includes positioning a vascular device that is a furlable thin film implant. When a furled thin film implant is positioned in the subject it may contact a hydrating liquid in the subject and unfurl to produce an unfurled thin film structure. In some embodiments, the hydrating liquid may dissolve a pore forming agent from the outside layer of the unfurled thin film structure to produce a porous layer that provides for release therethrough of the lipid mediator from the implant.

In some embodiments, the method includes releasing or eluting the lipid mediator in a time-controlled fashion from the vascular device. In this way, the therapeutic advantages imparted by the administration of the lipid mediator may be continued for an extended period of time. In some embodiments, the method includes eluting the lipid mediator to the surrounding tissue, cells or vascular wall upon placement of the device in the patient for a period ranging from about 2 minutes to about 1 day or more, such as 2 days or more, 3 days or more, 7 days or more, 14 days or more, 21 days or more, or 1 month or more. In certain embodiments of the subject method, the releasing locally delivers an effective amount of the lipid mediator over an extended period of time, e.g., 1 or more months, such as 2 or more, 3 or more, 4 or more, 5 or more, 6 or more, 9 or more or 12 or more months.

In certain embodiments of the method, the releasing of the lipid mediator (and optional additional bioactive agent) from the vascular device is a controlled release that occurs without an initial burst of bioactive agent. By "without an initial burst" is meant that the lipid mediator (and/or optional additional bioactive agent) does not release from the implant in an appreciable amount during a predetermined initial period (e.g., 1 week or less, such as 3 days or less, 1 day or less, 12 hours or less, 6 hours or less, 3 hours or less or 1 hour or less). The presence and level of an initial burst of a lipid mediator or bioactive agent may be readily determined employing any convenient pharmacological methods. For example, less than about 50% of the lipid mediator (and/or optional additional bioactive agent) is released in the predetermined initial period, such less than about 40%, less than about 30%, less than about 20%, less than about 10%, less than about 5%, less than about 2%, or less than about 1% of the lipid mediator (and/or optional additional bioactive agent).

In certain embodiments of the methods, the releasing of the lipid mediator (and/or optional additional bioactive agent) from the vascular device is substantially zero order over an extended period of time. By "substantially zero order" is meant a release profile of the bioactive agent from the device that provides for a substantially constant release of drug, e.g., a release profile where the fraction of lipid mediator (and/or optional additional bioactive agent) eluted from the implant is substantially linear with respect to time, over an extended period of time. For example, a release profile where about 20% or less, such as about 10% or less, or 5% or less of lipid mediator is released after 10 days following implantation. For example, a release profile where about 40% or less, such as about 30% or less, or about 20% or less of lipid mediator is released after 20 days following implantation. For example, a release profile where about 50% or less, such as about 40% or less, or about 30% or less of lipid mediator is released after 30 days following implantation. For example, a release profile where about 60% or less, such as about 50% or less, or about 40% or less of lipid mediator is released after 40 days following implantation. For example, a release profile where about 80% or less, such as about 70% or less, about 60% or less, or about 50% or less of lipid mediator is released after 50 days following implantation. For example, a release profile where about 90% or less, such as about 80% or less, about 70% or less, about 60% or less, or about 50% or less of lipid mediator is released after 60 days following implantation.

The bioactivity or stability of the lipid mediator may be maintained in the vascular device after implantation for an extended period of time. For example, the bioactivity of a lipid mediator per unit amount of the agent that is eluted from the implant is substantially constant over an extended period of time, e.g., 1 month or more, 2 months or more, 70 days or more, or 3 months or more.

The subject methods can be used for both human clinical medicine and veterinary applications. Thus, the subject can be a human or, in the case of veterinary applications, can be a laboratory, agricultural, domestic, or wild animal. As used herein, the terms "host", "subject", and "patient" are used interchangeably. The subject implants and methods can be applied to mammals including, but not limited to, humans, laboratory animals such as monkeys and chimpanzees, domestic animals such as dogs and cats, agricultural animals such as cows, horses, pigs, sheep, goats, and wild animals in captivity.

In some embodiments, the release kinetics of the pro-resolving lipid mediators (and optional additional bioactive agents) that are eluted from the vascular devices provide for a substantially constant local delivery of a therapeutically relevant dosage of the pro-resolving lipid mediators (and optional additional bioactive agents). In certain embodiments, the release kinetics of the lipid mediator (and optional additional bioactive agent) is substantially zero order over an extended period of time. In some embodiments, the vascular device may be designed to provide for two elution profiles, e.g., a thin film implant having a first early elution from a first layer, and a second later elution from a second layer.

In some embodiments, the lipid mediator is stable in the subject vascular device over an extended period of time. In certain embodiments, the activity of the lipid mediator in the reservoir is maintained following implantation in vivo. For example, the activity of the lipid mediator in the reservoir is maintained over a period of about 30 or more days, such as about 60 or more days, 70 or more days, 3 or more months, about 4 or more months, about 5 or more months, about 6 or more months, about 8 or more months, about 10 or more months, or about 12 or more months.

Additional Bioactive Agents

The subject pro-resolving lipid mediators may be administered in combination with one or more additional bioactive agents. As such, the subject methods further include co-administration of an additional bioactive agent that may be administered simultaneously or sequentially, using any convenient method, including but not limited to, administration of one or more pharmaceutical compositions, elution from a vascular device, e.g., as described herein. In certain instances, additional bioactive agents may be loaded into the vascular device including the lipid mediator and delivered to the target site in the vasculature. In certain embodiments, the additional bioactive agent is co-eluted with the subject lipid mediator (e.g., a D-series resolvin or lipoxin) from the vascular device.

Suitable additional bioactive agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art. In some embodiments, the additional bioactive agent is selected from an anti-inflammatory agent and an antiproliferative agent.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2-hydroxyethyl)rapamycin (EVEROLIMUS™), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Various therapeutic agents such as antithrombogenic or antiproliferative drugs are used to further control local thrombosis. Examples of additional bioactive agents, such as therapeutic agents or drugs that are suitable for use in accordance with the subject methods, pro-resolving lipid mediators and devices include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B™ (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as CAPTOPRIL (available from Squibb located in New York, N.Y.), CILAZAPRIL (available from Hoffman-LaRoche located in Basel, Switzerland), or LISINOPRIL (available from Merck located in Whitehouse Station, N.J.); calcium channel blockers (such as nifedipine), colchicine, fibroblast growth factor (FGF) antagonists, fish oil (omega 3-fatty acid), histamine antagonists, LOVASTATIN (an inhibitor of HMG-CoA reductase, a cholesterol lowering drug from Merck), methotrexate, monoclonal antibodies (such as platelet-derived growth factor (PDGF) receptors), nitroprusside, phosphodiesterase inhibitors, prostaglandin inhibitor (available from GlaxoSmithKline located in United Kingdom), seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

Utility

The pro-resolving lipid mediators, vascular devices, compositions and methods of the disclosure, e.g., as described herein, find use in a variety of applications. Applications of interest include, but are not limited to: research applications and therapeutic applications. Methods of the disclosure find use in a variety of different applications including any convenient application where modulation of a biological process of a VSMC and/or VEC, or modulation of inflammation of a vascular wall is of interest.

In some cases, the pro-resolving lipid mediators and methods find use in the attenuation of injury-induced cell proliferation, leukocyte infiltration, inflammatory gene expression, and superoxide production in the acute phase, which may translate into a significant reduction of neointimal hyperplasia after vascular injury. Without wishing to be bound by theory, the processes of monocyte recruitment, VSMC and/or VEC proliferation, and VSMC and/or VEC migration can impact clinical restenosis, thus collectively these effects of the subject pro-resolving lipid mediators may modulate the in-vivo response to injury.

The subject pro-resolving lipid mediators, vascular devices, compositions and methods find use in a variety of therapeutic applications. Therapeutic applications of interest include those applications in which modulation of the healing response to vascular injury and/or vascular scarring is of interest. In some cases, applications of interest include applications in which a biological activity of a VSMC and/or VEC, or inflammation and/or restenosis of a vascular wall is the cause or a compounding factor in disease progression or response to vascular injury and/or vascular scarring. As such, the subject pro-resolving lipid mediators find use in the treatment of a variety of different conditions in which the modulation of inflammation and/or restenosis of vascular walls or biological activities of VSMCs and/or VECs in the host is desired. For example, the subject pro-resolving lipid mediators and methods may find use in the treatment of vascular injury and/or scarring, post treatment for arterial occlusive diseases, whether surgical (bypass graft, endarterectomy) or catheter-based (angioplasty, stenting), where often recurrent vessel narrowing (restenosis) develops, a manifestation of the local response to injury. In some embodiments, the pro-resolving lipid mediators and methods find use in treating a vascular disorder such as a vascular injury or vascular scarring. In certain embodiments, the vascular disorder is neointimal hyperplasia, or restenosis. In some embodiments, the pro-resolving lipid mediators and methods find use in the treatment of a chronic inflammatory disease of the vascular wall, e.g., atherosclerosis.

The subject pro-resolving lipid mediators and vascular devices find use in the local delivery of lipid mediator, e.g., to the site of a vascular injury.

The subject pro-resolving lipid mediators and methods find use in a variety of research applications. Research applications of interest include application related to the elucidation of biological processes that modulate inflammation of vascular walls, chronic inflammatory diseases, responses to vascular injuries, restenosis, etc.

Formulations, Dosage and Administration

By virtue of their capacity to modulate biological activities of vascular smooth muscle cells (VSMC), vascular endothelial cells (VEC) and inflammation of vascular walls, the subject pro-resolving lipid mediators may be used in pharmaceutical compositions and methods for treatment of a variety of vascular diseases and injuries, such as, chronic inflammatory diseases, vascular injuries, restenosis, and the like.

In some embodiments, such treatment is achieved by administering to the mammal an effective amount of the lipid mediator sufficient to modulate the vascular disease or injury in the mammal. In certain embodiments, such treatment includes modulating inflammation of a vascular wall of the mammal. In certain cases, administering to the mammal an effective amount of the lipid mediator involves contacting VSMCs and/or VECs in a blood vessel of the mammal with a lipid mediator to modulate a biological activity in the VSMCs and/or VECs, e.g. inhibiting proliferation and/or migration, inhibiting monocyte adhesion to the VSMC and/or VEC, reducing expression of a pro-inflammatory gene, etc.

For in vivo protocols, any convenient administration protocol may be employed. Depending upon the potency of the lipid mediator, the response desired, the manner of administration, the half-life, the number of cells present, various protocols may be employed. The lipid mediator may be administered parenterally or orally. The number of administrations will depend upon the factors described above. The lipid mediator may be taken orally as a pill, powder, or dispersion; bucally; sublingually; injected intravascularly, intraperitoneally, subcutaneously; by inhalation, or the like. The precise dose and particular method of administration will vary and may be readily determined by the attending physician or human or animal healthcare provider, e.g., the dose and method may be determined empirically. The particular dosage of the lipid mediator for any application may be determined in accordance with the procedures used for therapeutic dosage monitoring, where maintenance of a particular level is desired over an extended period of times, for example, greater than about two weeks, or where there is repetitive therapy, with individual or repeated doses of lipid mediator over short periods of time, with extended intervals, for example, two weeks or more. In some embodiments, the local response and level of the lipid mediator may be modulated as necessary by utilizing a vascular device and methods as described above.

The subject pro-resolving lipid mediators can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. The subject formulations can be made into aerosol formulations to be administered via inhalation, or into topical formulations. In some embodiments, formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Unit dosage forms for oral administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may include the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Dose levels can vary as a function of the specific lipid mediator, the nature of the delivery vehicle, and the like. Desired dosages for a given compound are readily determinable by a variety of means. The dose administered to an animal, particularly a human, in the context of the present invention should be sufficient to effect a prophylactic or therapeutic response in the animal over a reasonable time frame, e.g., as described in greater detail below. Dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound.

In pharmaceutical dosage forms, the subject pro-resolving lipid mediators may be administered in the form of a free acid or base, their pharmaceutically acceptable salts, or they may also be used alone or in appropriate association, as well as in combination, with other pharmaceutically active compounds.

Combination Therapies

In some embodiments, the subject pro-resolving lipid mediators may be administered in combination with one or more additional bioactive agents (e.g., as described herein) or therapies. Combination therapy includes administration of a single pharmaceutical dosage formulation which contains the subject compound and one or more additional bioactive agents; as well as administration of the subject pro-resolving lipid mediators and one or more additional bioactive agent(s) in its own separate pharmaceutical dosage formulation. For example, a subject lipid mediator and an anti-inflammatory or anti-proliferative agent can be administered to the patient together in a single dosage composition such as a combined formulation, or each agent can be administered in a separate dosage formulation. Where separate dosage formulations are used, the subject compound and one or more additional agents can be administered concurrently, or at separately staggered times, e.g., sequentially.

Kits

Kits for use in connection with the subject pro-resolving lipid mediators and methods are also provided. The kits may include one or more components employed in the subject methods, e.g., lipid mediator compounds, additional bioactive agents, and vascular devices, as described herein. The above-described vascular devices and implants, comprising one or more pro-resolving lipid mediators (and optional additional bioactive agents) for elution to the surrounding tissue upon placement in a subject, can be provided in kits, with suitable instructions in order to conduct the methods as described above. In certain embodiments, the kit contains a thin film implant that has a furled structure. In some embodiments, the implant has an unfurled structure and the kit includes instructions for furling the implant so that the implant may be implanted in a subject by syringe.

The subject kits may also include a syringe or catheter capable of delivering the implant to a subject, e.g., by injection of a carrier fluid containing the implant having a furled structure. The syringe has a gauge (e.g., 20 gauge) suitable for in vivo injection of the implant. In some embodiments, the syringe is pre-loaded with a carrier fluid that contains the implant, where the implant is maintained in a furled structure in the carrier fluid. In other embodiments, the kit includes a container for storing the implant prior to loading of the syringe and implantation in the subject, where the implant can be stored having a furled or an unfurled structure. In certain embodiments, when the implant is stored in the container in an unfurled state, the kit may include instructions for furling the implant prior to implantation, e.g., by drying under reduced vacuum. The container may optionally include a carrier fluid suitable for storing the subject implant and/or implantation.

In some embodiments, the kit contains in separate containers materials necessary for preparing the vascular device. Instructions (e.g., written, tape, VCR, CD-ROM, etc.) for carrying out the methods may be included in the kit. The kit can also contain, depending on the particular method, other packaged reagents and materials (i.e. buffers and the like). The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject kits. As with the instructions, the means for obtaining the instructions and/or programming is generally recorded on a suitable recording medium.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods

Cell Isolation and Culture

Primary cultures of human greater saphenous vein smooth muscle cells (hVSMC) are isolated from saphenous vein discarded at the time of bypass operation in an Institutional Review Board-approved protocol as described by Conte et al. "Regulation of vein graft hyperplasia by survivin, an inhibitor of apoptosis protein." Arterioscler Thromb Vasc Biol. 2005; 25:2081-2087. VSMCs are maintained in Dulbecco's modified Eagle's medium (DMEM Low Glucose) (HyClone Laboratories Inc, Logan, Utah) containing 10% fetal bovine serum (FBS) (Invitrogen Life Technologies, Grand Island, N.Y.) and used between passages 2-5. Endothelial cells were maintained in Medium 199 supplemented with EBSS (Hyclone Laboratories, Logan, Utah, USA) and Endothelial Cell Growth Supplement. Cells between passages 3-8 were used for the experiments.

Rabbit Femoral Artery Balloon Injury

All animal experiments are performed under a protocol approved by University of California San Francisco Animal Care Committee. New Zealand White Rabbits (NZWR, Western Oregon Rabbit Company, Philomath, Oreg.) weighing 3 to 5 kg and maintained on a normal chow diet are used in all experiments. Animals are anesthetized for surgical procedures with intramuscular injection of ketamine (25 mg/kg) and xylazine (5 mg/kg), and maintained with inhalation of isoflurane. The balloon injury model is made as described by Conte et al. "Efficient repopulation of denuded rabbit arteries with autologous genetically modified endothelial cells," Circulation. 1994; 89:2161-2169. Rabbits undergo bilateral external iliac and femoral artery injury with 2F Fogarty balloon catheter (Applied Medical Resources Corp. Rancho Santa Margarita, Calif.). After balloon injury RvD2 (10 nM, Cayman chemical, Ann Arbor, Mich.) is infused to luminal area of the right femoral artery and control vehicle (normal saline with 0.1% ethanol) is infused to the left femoral artery, and then left undisturbed for 20 minutes. For evaluation of acute effects the rabbits are euthanized at 3 days after injury by intravenous overdose of sodium Nembutal. The femoral arteries are harvested and cryosection is made for immunohistochemistry, and total RNA from treated and control tissue is isolated. For evaluation of subacute responses regarding intimal hyperplasia the rabbits are euthanized at 28 days after injury and the tissue is perfusion-fixed in 10% formalin and processed as described by Conte et al. Arterioscler Thromb Vasc Biol. 2005; 25:2081-2087.

Monocyte Adhesion

RvD. A static monocyte adhesion assay is performed as described by Patricia et al. "Lipoxygenase products increase monocyte adhesion to human aortic endothelial cells", Arterioscler Thromb Vasc Biol. 1999; 19:2615-2622. U937 monocytes are labeled with 1 µM of calcein-AM (Invitrogen) for 30 minutes at 37° C. in PBS. The cells are washed three times and resuspended in PBS without serum at a concentration of $1.0 \times 10^6$ cells/mL. SMCs are grown to 100% confluence in 96-well dishes and treated with cytokines (10 ng/mL TNF-α (Sigma-Aldrich Inc., St. Louis, Mo.) or 1 nM IL-1β (R&D systems, Minneapolis, Minn.)) in the presence or absence of serial concentration of RvD1 or RvD2 (0.01-100 nM, Cayman chemical) for 4 hours at 37° C. Two hundred µL of labeled monocytes ($2.0 \times 10^5$ cells) are added to each well. After a 15-minute incubation at 37° C., unbound cells were washed off with PBS three times. Fluorescence measurements (excitation 494 nm, emission 517 nm) of bound monocytes are made with plate reader (Spectra Max M2, Molecular Devices, LLC, Sunnyvale, Calif.).

MaR-1. VSMCs and ECs were seeded on a 96 well plate (20000 cells/well for VSMCs and 50000 cells/well for ECs) and after 2 days, were treated with Maresin-1 (1-100 nM) for 30 min followed by TNF-α for 4 hr and then calcein AM-labeled U937 cells were added on top of the VSMCs. After 15-minute incubation at 37 C, unbound cells were washed off with cold PBS. Fluorescence measurements (ex 494 nm, em 517 nm) of bound monocytes were taken with a plate reader. For capturing images, the assay was performed in 8-well chamber slides (Nunc Labtek) and images were taken after cold PBS wash (three times) following U937 incubation.

Cell Proliferation

Cell proliferation assay is performed as described by Conte et al. Arterioscler Thromb Vasc Biol. 2005; 25:2081-2087. SMCs are seeded onto 24-well plates at a density of 5,000 cells per well, then treated with RvD1 or RvD2 (0.01, 1, or 100 nM) in media containing 10% FBS. Medium is replenished every 2 days. Alamar Blue (Invitrogen) assays are conducted every 48 hours according to the manufacturer's protocol. Fluorescence measurements (excitation 506 nm, emission 590 nm) are made on media aliquots; a standard curve is generated by correlating emission intensity with viable cell counts using Trypan Blue exclusion.

Transwell Migration

RvD. VSMC migration is assayed using 8 µm-pore transwell insert as described by Conte et al., "C-reactive protein and vein graft disease: evidence for a direct effect on smooth muscle cell phenotype via modulation of PDGF receptor-beta," Am J Physiol Heart Circ Physiol. 2008; 295: H1132-H1140. Cells are exposed to 50 ng/mL PDGF-AB (Sigma) in the presence or absence of RvD1, RvD2 (0.01, 1, or 100 nM), or 25 µg/mL PDGF-AB neutralizing antibody (Sigma). All compounds are present in both top and bottom wells for the full duration of chemotaxis experiments (8 hours).

MaR-1. VSMCs were serum starved for 1-2 days, then trypsinized and seeded in 8-µm-pore transwell inserts (Corning Glass Works, Corning, N.Y.) at a concentration of 30,000 cells per well. Cells were allowed to attach for 2 hr, then pretreated with Maresin-1 (1-100 nM) or vehicle (0.1% ethanol) control for 30 min before the addition of PDGF-BB (50 ng/ml; Sigma-Aldrich, St. Louis, Mo., USA) to the lower wells. 7S-Maresin-1 was added to both upper and lower wells for the full duration of chemotaxis experiment (15 hr). The membranes were fixed with methanol and cut out, mounted with DAPI, and migrated cells were counted under fluorescence microscope. Ten images per well were taken randomly under a 10× magnification and number of cells were counted in all the images to calculate mean for a given well.

Cell Viability Assay

Cells are plated onto 24-well plates and treated with or without RvD1 or RvD2 (1, 10, and 100 nM) for 8 hours. MTT viability assay is performed per manufacturer's instructions (TOX1 assay, Sigma).

Transcription Factor Array

Cells are plated onto 96-well plates and treated with 10 ng/ml TNF-α in the presence or absence of 10 nM RvD2 for 18 hours and then nuclear extracts are prepared. Transcription factor profiling is performed using a multiplex array according to the manufacturer's instructions (Signosis Inc., Sunnyvale, Calif.).

Western Blotting

RvD. Human VSMCs are lysed in buffer (20 mM Tris-Hcl, 137 mM NaCl, 10% Glycerol, 1% NP-40) with protease inhibitors for 1 hour at 4° C. After centrifugation (15,000 g for 20 minutes), the whole cell extract (supernatant) is collected and is heated at 100° C. in Laemlli buffer for 6 minutes. The lysate (50 µg) is then run on NuPAGE 10% Bis-Tris gel (Invitrogen) and transferred to a PVDF membrane which is probed with anti-GPR32 antibody (1:500, Novus Biologicals, Littleton, Colo.) and anti-β actin (1:5000, Sigma) using QDot 625 Western blotting kit (Invitrogen).

Mar-1. VSMCs and ECs were lysed in buffer (20 mM Tris-Hcl, 137 mM NaCl, 10% Glycerol, 1% NP-40) with protease and phosphatase inhibitors (Halt inhibitor capsules, Pierce, Inc) by sonication on ice. The lysates were instantly snap frozen in liquid nitrogen and thawed back later for western blotting. After centrifugation (15,000 g for 20 minutes), the whole cell extract (supernatant) was collected and was heated at 100° C. in Laemlli buffer for 6 minutes. Lysates were run on Mini-Protean TGX gels (Biorad) and transferred on PVDF membranes which were probed with appropriate primary and secondary antibodies and visualized for quantitation using q-dot nanocrystals (Life Technologies, Inc).

Immunofluorescent Staining

All the immunofluorescent staining is completed on 6-µm-thick frozen sections fixed by ice cold acetone for 10 minutes. Goat anti-mouse IgG conjugated with Alexa Fluor 488 or 568 (1:100, respectively, Invitrogen) is selected as secondary antibody. Anti-Ki67 (1:100, NCL-L-Ki67-MM1, Novocastra Laboratories, Newcastle upon Tyne, UK) is utilized for cell proliferation detection. Anti-CD45 (1:200, L12/201, AbD Serotec, Oxford, UK) is utilized for leukocyte infiltration detection. DAPI nuclear counter staining (Vector Laboratories, Inc., Burlingame, Calif.) is utilized on all the immunofluorescent staining. Photography is completed via Olympus BX51 microscope (Olympus America, Inc., Center valley, PA) with EXFO X-cite 120 system (EXFO Photonic Solutions, Inc., Mississauga, Ontario), Olympus DP70 Digital Microscope Camera (Olympus), and DPController software (Olympus). Six vessel zones (under ×200 magnification) are selected randomly on three coordinate axes of every stained rabbit arterial cross-section. The proportion of Ki67 is calculated by absolute positive cell number divided by DAPI positive nuclei. Leukocyte infiltration index is calculated as number of nuclei in CD45 positive area divided by total number of DAPI positive nuclei.

Immunofluorescence for p65 (RelA): 15000 VSMCs or 30000 ECs were seeded on a 8-well chamber slide. Cells received 30 min of Maresin-1 pretreatment, followed by TNF-α for 2 hr. Cells were fixed in 2% paraformaldehyde, followed by permeabilization with ice-cold acetone (10 min) and 1% Triton X-100 (20 min). Cells were incubated overnight in a humidified chamber with anti-p65 antibody (Santa Cruz Biotechnology Inc.) followed by Alexa-fluor 488 tagged secondary antibody (Life Technologies) and were visualized under a fluorescent microscope.

Detection of Superoxide Production

RvD1. Cells are seeded and grown on chamber slides at a density of 10,000 cells per chamber for 2 days, followed by treatment with 10 ng/ml TNF-α with or without RvD1 (10 and 100 nM) in serum-free media for 4 hours. After incubation cells are incubated with DHE (5 µmol/L, Invitrogen) in PBS for 30 minutes at 37° C. in a humidified chamber protected from light. DAPI nuclear counter staining is utilized. For frozen section 30-µm-thick sections are incubated with DHE (10 µmol/L) in PBS for 30 minutes at the same condition described above. Fluorescence was detected with TRITC filter allowing the detection of the DHE emission wavelength of 590-620 nm. The fluorescence lamp gain is standardized for all images and analyses. Fluorescence quantitation is performed using ImageJ analysis software (National Institute of Health, Bethesda, Md.). For VSMC the fluorescence intensity is determined for the DHE-stained control cells (no treatment control) from each experimental group and then individual treated cells from the same group are normalized to the corresponding value. For frozen sections the fluorescence intensity is determined for the DHE-stained control vessels (uninjured abdominal aorta) from each experimental group and then individual treated vessels from the same group are normalized to the corresponding value.

Mar-1. Cells were grown in 8-well chamber slides at a density of 15000 cells/well for 2 days for VSMCs and 50000 cells/well for 2 days for ECs in a 96 well plate. After treatments, cells were incubated with dihydroethidium (DHE, 3 µM, Invitrogen) or CellRox (Invitrogen Inc, 5 µM for ECs) in media for 30 minutes at 37° C. in a humidified chamber with 5% CO2 protected from light. DAPI nuclear counter staining was utilized for DHE staining. For DHE, fluorescence was detected with TRITC filter allowing the detection of the DHE emission wavelength of 590-620 nm. Fluorescence quantitation was performed using ImageJ analysis software. For ECs, fluorescence measurements were taken using a Spectramax M2e plate reader.

Cell-shape Measurement

Cells were cultured in 8-well chamber slides (3,000 cells/well) and pretreated with MaR-1 or vehicle (0.1% ethanol) for 30 min followed by the addition of PDGF-BB (50 ng/ml) for 1 h. Cells were washed twice in phosphate-buffered saline (PBS), permeabilized with 0.1% Triton-X, and then fixed in 4% formaldehyde, labeled with Alexa Fluor 568 phalloidin (Invitrogen) and DAPI, and then mounted on glass slides. Cell area and length/width ratio were determined by outlining the cell dimensions and computing 2-dimensional area using GIMP image analysis software (GIMP, freeware; www.gimp.org). For each condition, dimensions were measured from 30 randomly selected cells, and all treatment conditions were performed in triplicate.

Inflammation Array

Media was collected and incubated for 2 hr with the inflammation array membranes. The cells were harvested for protein estimation for normalization purposes. The membranes were washed following instruction protocol supplied by the manufacturer (Raybiotech Inc., Norcross, Ga.) and probed with biotinylated anti-cytokine antibody cocktail (provided by the manufacturer) for 2 hrs. The membranes were again washed with appropriate buffers provided by the manufacturer and incubated for 2 hrs with HRP-conjugated streptavidin, followed by chemiluminescence based detection of signal by Chemidoc (Biorad Inc.)

Morphometry

Verhoeff-Van Gieson elastin staining is performed on perfusion-fixed vessel arterial cross-sections to evaluate neointimal hyperplasia. Lumen circumference, internal elastic lamina, and external elastic lamina are delineated by hand, and planimetry is completed using ImageJ software.

Analysis of Gene Expression by RT-PCR

Cells are plated onto 6-well plates at 100% confluency in DMEM plus 10% FBS and allowed to attached overnight. Cells are then made quiescent by placing in serum-free media for 48-72 hours prior to start of experiments. Cells are treated with or without RvD1 or RvD2 at the indicated concentrations for one hour followed by co-incubation with cytokine (TNF-$\alpha$ 10 ng/ml) for up to 18 hours. In a separate set of experiments to examine the role of G-protein receptors, VSMCs are exposed to TNF-$\alpha$ and RvD2 (10 nM) as described above, in the presence or absence of pertussis toxin (PTX 100 ng/ml). Total RNA from rabbit sample or cells is isolated with PureLink RNA Mini kit (Ambion Life Technologies, Carlsbad, Calif.) with RNase-free DNase treatment according to manufacturer's protocol. One microgram of total RNA (from either VSMC or rabbit tissue) is used to generate cDNA using High Capacity cDNA Reverse Transcription Kit (Applied Biosystems, Foster City, Calif.) for subsequent RT-PCR reactions. Sybrgreen Amplified DNA is detected by incorporation SYBR Green (Qiagen, Germantown, Md.). Dissociation curve analyses are performed to confirm the specificity of the SYBR Green signal. Data is normalized to at least two reference genes. The primers used in this PCR are listed in Table 1. Most primer pairs span across an intron. PCR parameters include an initial 10 minute denaturation step at 95° C. followed by a cycling program of 95° C. for 10 seconds, 60° C. for 30 seconds for 40 cycles (CFX 96 Real Time System, Bio Rad, Hercules, Calif.).

TABLE 1

Primers used in quantitative RT-PCR

| Primers | Forward sequence | Reverse sequence | Exon |
|---|---|---|---|
| Hu VCAM-1 | TGCAAGTCTACATATCACCCAAGAATA (SEQ ID NO: 1) | GGTAGACCCTCGCTGGAACA (SEQ ID NO: 2) | M |
| Hu ICAM-1 | GCCGGCCAGCTTATACACAA (SEQ ID NO: 3) | TGGCCACGTCCAGTTTCC (SEQ ID NO: 4) | M |
| Hu TNF-$\alpha$ | AGAGGGCCTGTACCTCATCTACTC (SEQ ID NO: 5) | GGTTGACCTTGGTCTGGTAGGA (SEQ ID NO: 6) | M |
| Hu IL-1$\beta$ | CCCTAAACAGATGAAGTGCTCCTT (SEQ ID NO: 7) | GGTGGTCGGAGATTCGTAGCT (SEQ ID NO: 8) | M |
| Hu MCP-1 | CAGCAGCAAGTGTCCCAAAG (SEQ ID NO: 9) | GAATCCTGAACCCACTTCTGCTT (SEQ ID NO: 10) | M |
| Hu IL-6 | CCGGGAACGAAAGAGAAGCT (SEQ ID NO: 11) | AGCAGCCCCAGGGAGAAG (SEQ ID NO: 12) | M |
| Hu IL-1$\alpha$ | GAATCAGAAATCCTTCTATCATGTAAGC (SEQ ID NO: 13) | ACTACCACCATGCTCTCCTTGAA (SEQ ID NO: 14) | M |
| Hu HPRT | CAAGCTTGCTGGTGAAAGGA (SEQ ID NO: 15) | TGAAGTACTTATAGTCAAGGGCATATC (SEQ ID NO: 16) | M |
| Hu UBC | ATTTGGGTCGCGGTTCTTG (SEQ ID NO: 17) | TGCCTTGACATTCTCGATGGT (SEQ ID NO: 18) | M |
| Rb VCAM-1 | GGTCTACATTTCACCCAAGAATACAG (SEQ ID NO: 19) | ACTGGTAGACCCTCGCTGGAA (SEQ ID NO: 20) | M |
| Rb ICAM-1 | AGACGCAGCTGAGCAAGGA (SEQ ID NO: 21) | CACAGTCGGAAAAGCAGATGAG (SEQ ID NO: 22) | G |
| Rb TNF-$\alpha$ | GGAAGAGCAGTCCCCAAACA (SEQ ID NO: 23) | GGGCTAGAGGCTTGTCACTCA (SEQ ID NO: 24) | M |

TABLE 1-continued

Primers used in quantitative RT-PCR

| Primers | Forward sequence | Reverse sequence | Exon |
|---|---|---|---|
| Rb IL-1β | TGTACCTGTCCTGCGTGATGA (SEQ ID NO: 25) | TCGTTTTTCCATCTTCTTCTTTGG (SEQ ID NO: 26) | M |
| Rb MCP-1 | TGGGTCCAGGATGCCAT (SEQ ID NO: 27) | AGTCGTGTGTTCTTGGGTTGTG (SEQ ID NO: 28) | S |
| Rb IL-6 | ACGACCACGATCCACTTCATC (SEQ ID NO: 29) | AAGGACACCCGCACTCCAT (SEQ ID NO: 30) | S |
| Rb IL-1α | GAGTCGGCAAAGAAATCAAGATG (SEQ ID NO: 31) | GCAGAGCTGTATTCCTCATTTTCA (SEQ ID NO: 32) | G |
| Rb HPRT | GTGAAAAGGACCCCTCGAAGT (SEQ ID NO: 33) | TCATTATAGTCAAGGGCATATCCT ACA (SEQ ID NO: 34) | M |
| Rb GAPDH | TCCCCGAGACACGATGGT (SEQ ID NO: 35) | ACAACATCCACTTTGCCAGAGTT (SEQ ID NO: 36) | S |

M: multiple exons; S: single exon; G: unknown exon

Statistical Analysis

Data are shown as mean±SEM. Direct comparisons are made using unpaired or paired Student's t-test, and multiple group comparisons are made using one-way or two-way analysis of variance (ANOVA) followed by Dunnett's or Bonferroni's post hoc tests where appropriate. In all cases, a level of $P<0.05$ is considered significant.

Results

RvD1 and RvD2 Attenuate Cell Adhesion, Proliferation, and Migration Responses of Human VSMC Following acutely denuding mechanical injury such as balloon angioplasty, exposed lumenal VSMC take on a pro-adhesive, proliferative, and migratory phenotype which may be modeled using standard in-vitro assays. In a static cell adhesion assay, RvD1 and RvD2 produced a dose-dependent inhibition of monocyte adhesion (U937) to cytokine (TNF-α (FIG. 1A) or IL-1β (FIG. 6))-stimulated VSMC. Peak inhibition of monocyte adhesion to TNF-α-stimulated VSMC was observed at 10 nM, with a maximum % inhibition of 36% for RvD1, and 41% for RvD2. Proliferation of VSMC in standard growth medium (10% serum) was reduced in dose-dependent fashion by exposure to both RvD1 (FIG. 7) and RvD2 (FIG. 1B), with maximum effect (59% inhibition in RvD1 and 63% inhibition in RvD2) observed at 100 nM ($P<0.01$). Similarly, VSMC chemotaxis to a PDGF-AB gradient was significantly reduced by RvD1 and RvD2 in dose-dependent fashion. Maximum % reduction in the cell migration assay was 63% in 100 nM RvD1 ($P<0.01$) and 69% in 100 nM RvD2 ($P<0.01$) (FIG. 1C). MTT cytotoxicity assays indicated that VSMC exposed to either RvD1 or RvD2 (1-100 nM) for 8 hours did not display significant loss of cell viability (FIG. 8).

FIG. 1: RvD1 and RvD2 attenuate cell adhesion, proliferation, and migration responses of human VSMC in-vitro. (A) Monocyte adhesion to VSMC. HVSMC were stimulated with TNF-α (10 ng/ml) for 4 hours, in the presence or absence of RvD1 or RvD2 at the indicated doses. Labeled U937 monocytes were overlain, and cell adhesion assay performed as described. Results are shown as relative percent inhibition, expressed as a percentage of the maximal adhesion for the agonist (n=6, results are mean±SEM, **$P<0.01$, *$P<0.05$, unpaired t-test). (B) HVSMC proliferation assay performed in normal growth medium (10% serum) as described in Methods. Dose-dependent inhibition of VSMC proliferation is shown for RvD2 (n=3, results are mean±SEM, $P<0.01$ vs control, two-way ANOVA followed by Dunnett's post hoc test). (C) VSMC migration response to PDGF-AB using a transwell assay. Results are expressed as percentage change in migration from unstimulated control (no PDGF). PDGF neutralizing antibody serves as positive control for inhibition. A dose-dependent inhibition of chemotaxis is demonstrated for both RvD1 and RvD2 (n=5, results are mean±SEM,  $P<0.01$, *$P<0.05$ vs PDGF-AB, one-way ANOVA followed by Dunnett's post hoc test).

RvD1 and RvD2 Reduce Pro-inflammatory Gene Expression in VSMC

Figure 9:
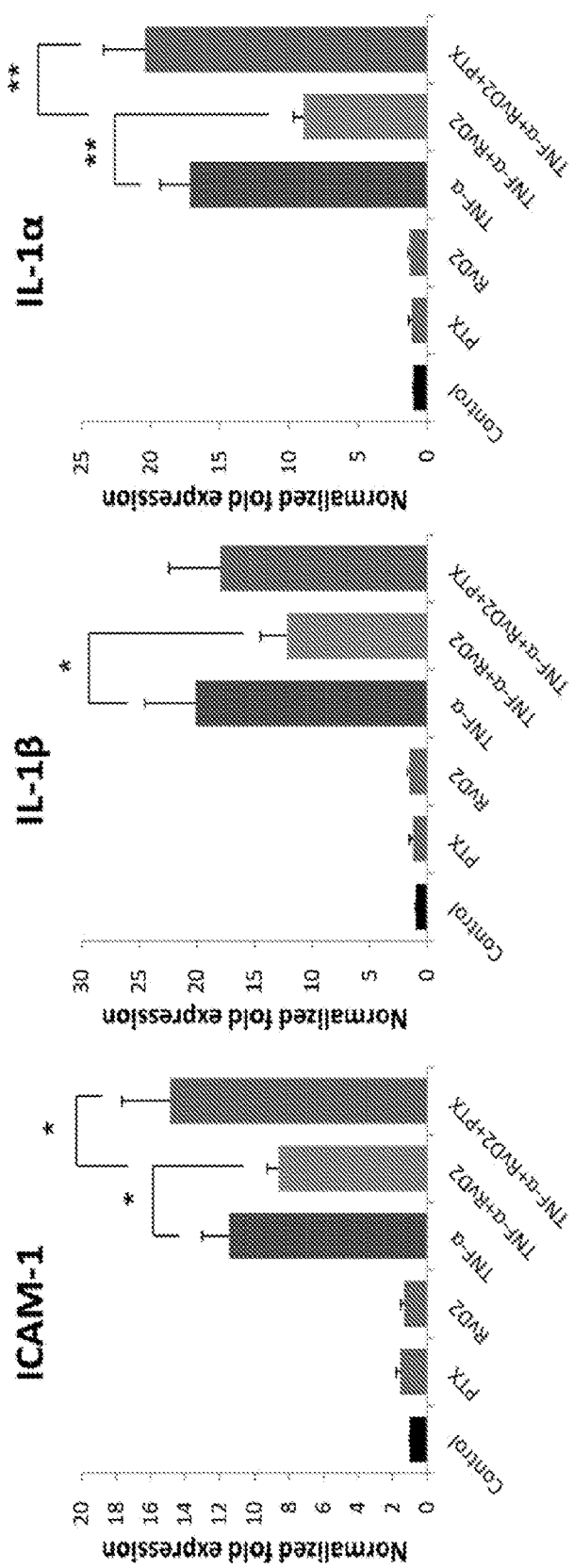
FIG. 9 shows the effects of RvD2 on gene expression in VSMC are sensitive to pertussis toxin (PTX), indicating that the signaling pathway involves one or more G-protein coupled receptors (GPCR). VSMCs were exposed to TNF-α and RvD2 (10 nM) in the presence or absence of PTX (100 ng/ml), and RNA analyzed for the expression of ICAM-1, IL-1β, and IL-1α by qPCR.
Figure 10:
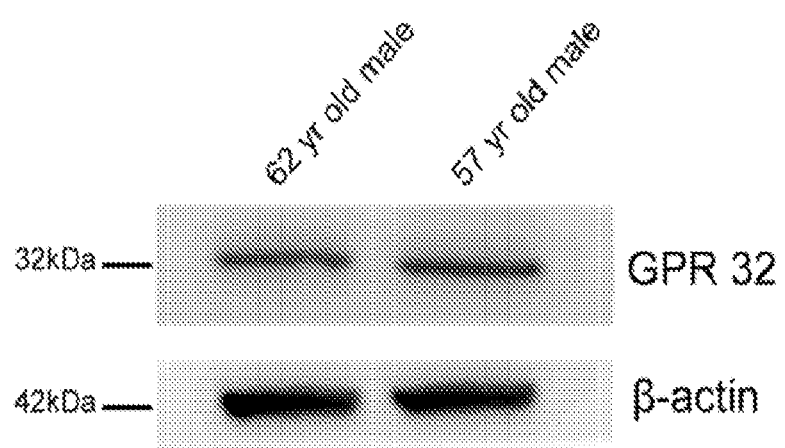
FIG. 10 shows the identification of GPR32 (a known receptor for RvD1) in human VSMC by Western blot analysis using anti-GPR32 antibody and anti-0 actin antibodies.

Cytokine-stimulated gene expression in primary cultured VSMC, including intercellular adhesion molecules and pro-inflammatory cytokines, was assessed using real-time quantitative RT-PCR. Both RvD1 and RvD2 produced a dose-dependent reduction of TNF-α-stimulated VCAM-1 and ICAM-1 expression (FIGS. 2A and 2B). In general, RvD2 was slightly more effective compared to RvD1. For VCAM-1, maximum % reduction was 69% in 100 nM RvD1 ($P<0.01$), and 76% in 100 nM RvD2 ($P<0.01$), and for ICAM-1 maximum % reduction was 63% in 100 nM RvD1 ($P<0.01$), and 70% in 100 nM RvD2 ($P<0.01$). There was a broad, significant reduction in the expression of multiple inflammatory cytokines including TNF-α, IL-1β, MCP-1, IL-6, and IL-1α by both RvD1 and RvD2, with the greatest attenuation seen in IL-1β expression (FIG. 2C). To confirm the role of a G-protein (Gα) receptor(s) in RvD signaling in VSMC, a separate set of experiments was conducted in the presence or absence of pertussis toxin (PTX), demonstrating abrogation of the inhibitory effects of RvD2 on ICAM-1, IL-1β, and IL-1α gene expression (FIG. 9). Of the two known receptors for RvD1, Conte et al. ("Aspirin-triggered lipoxin and resolvin E1 modulate vascular smooth muscle phenotype and correlate with peripheral atherosclerosis" Am J Pathol. 2010; 177:2116-2123) reported the presence of ALX expression in human VSMC. These results demonstrate that the other identified G-protein receptor for RvD1, GPR32, is also expressed in these cells by Western blot analysis from primary cultured human VSMC (FIG. 10).

Given the broad array of phenotypic change and target genes affected, we used a multiplex array to explore changes in transcription factor activity in resolvin-treated VSMC (FIG. 9). Transcription factors (TFs) regulating inflammatory pathways including Stat1, C/EBP, and SMAD were significantly downregulated in RvD2-treated VSMC compared to TNF-α-stimulated controls, as were several other TFs known to regulate cell proliferation and differentiation such as SATB1 and EGR.

Figure 2:
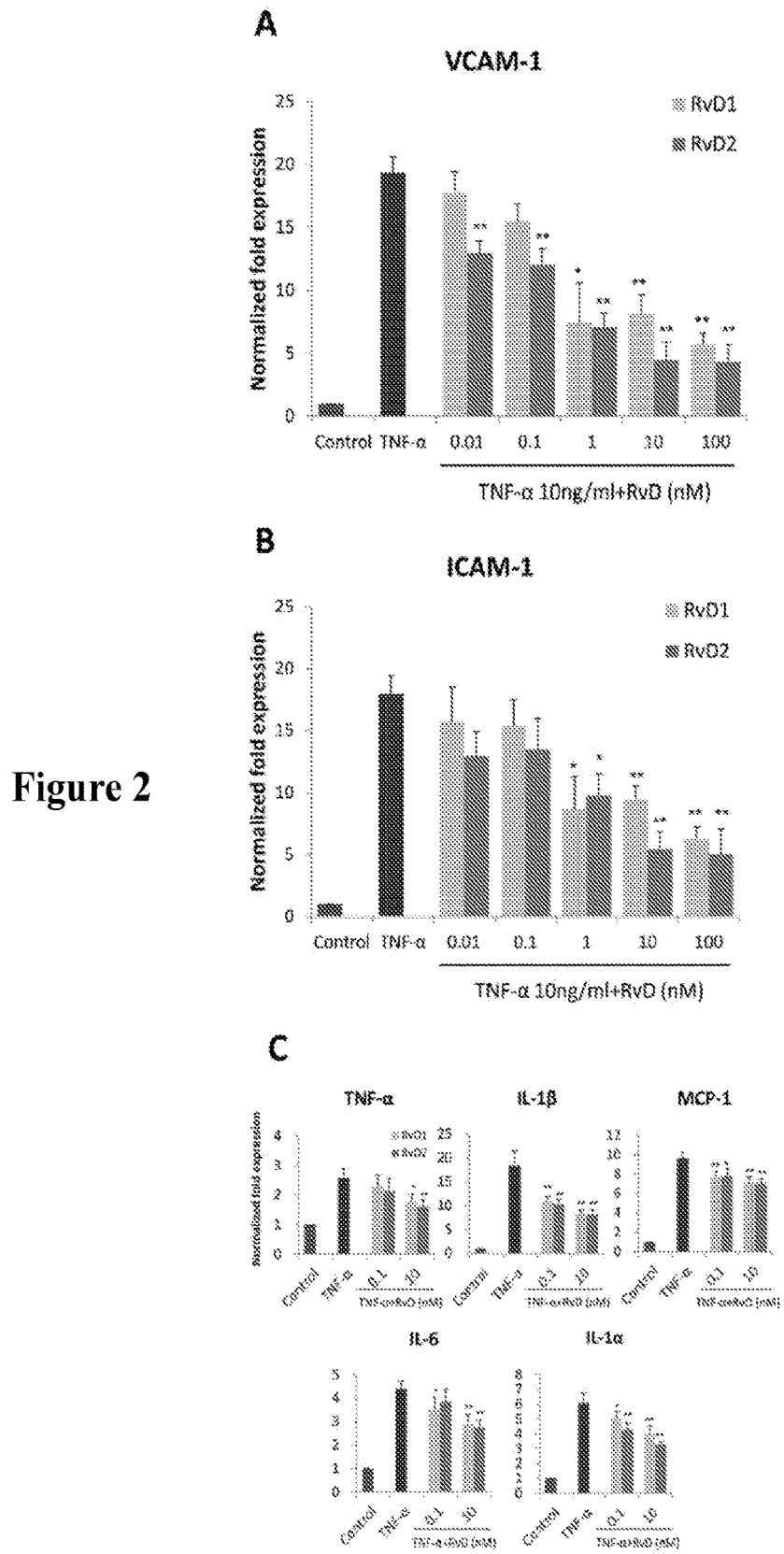
FIG. 2 shows RvD1 and RvD2 reduce pro-inflammatory gene expression in VSMC: (A, B) VSMCs were treated with TNF-α in the presence of RvD1 or RvD2 and the expression of the cell adhesion molecules VCAM-1 (A) and ICAM-1 (B) or multiple pro-inflammatory gene transcripts (C) was measured.

FIG. 2: RvD1 and RvD2 reduce pro-inflammatory gene expression in VSMC. (A, B) VSMCs were treated with TNF-α (10 ng/ml) for 18 hours, in the presence or absence of RvD1 or RvD2 across a concentration range shown. Expression of the cell adhesion molecules VCAM-1 (A) and ICAM-1 (B) was measured by qRT-PCR. (C) VSMCs were stimulated with TNF-α, as above in the presence or absence of RvD1 or RvD2 (0.1 nM or 10 nM), and qPCR was performed for multiple pro-inflammatory gene transcripts. Shown are significant reductions in the expression of TNF-α, IL-1β, MCP-1, IL-6, and IL-1α (n=3, results are mean±SEM, **$P<0.01$, *$P<0.05$, unpaired t-test).

RvD2 Modulates the Acute Vascular Injury Response

Following balloon angioplasty, rabbit femoral arteries were immediately exposed to RvD2 (10 nM) vs vehicle by brief (20 minutes) intraluminal incubation. Short term effects on the local tissue response were evaluated 3 days after injury (n=6). Cell proliferation (Ki-67 staining index) was decreased in RvD2-treated vessels compared to control (% inhibition 51%, $P<0.01$, paired t-test; FIG. 3A-3C). CD45 staining showed that leukocyte infiltration after injury was also inhibited by RvD2 (% inhibition 41%, $P<0.05$, paired t-test; FIG. 3D-3F). Inflammatory gene expression in the treated arteries was evaluated by qPCR, demonstrating significant reductions in TNF-α, MCP-1, and IL-1α expression in the RvD2-treated arteries vs vehicle-treated controls (FIG. 3G).

Figure 3:
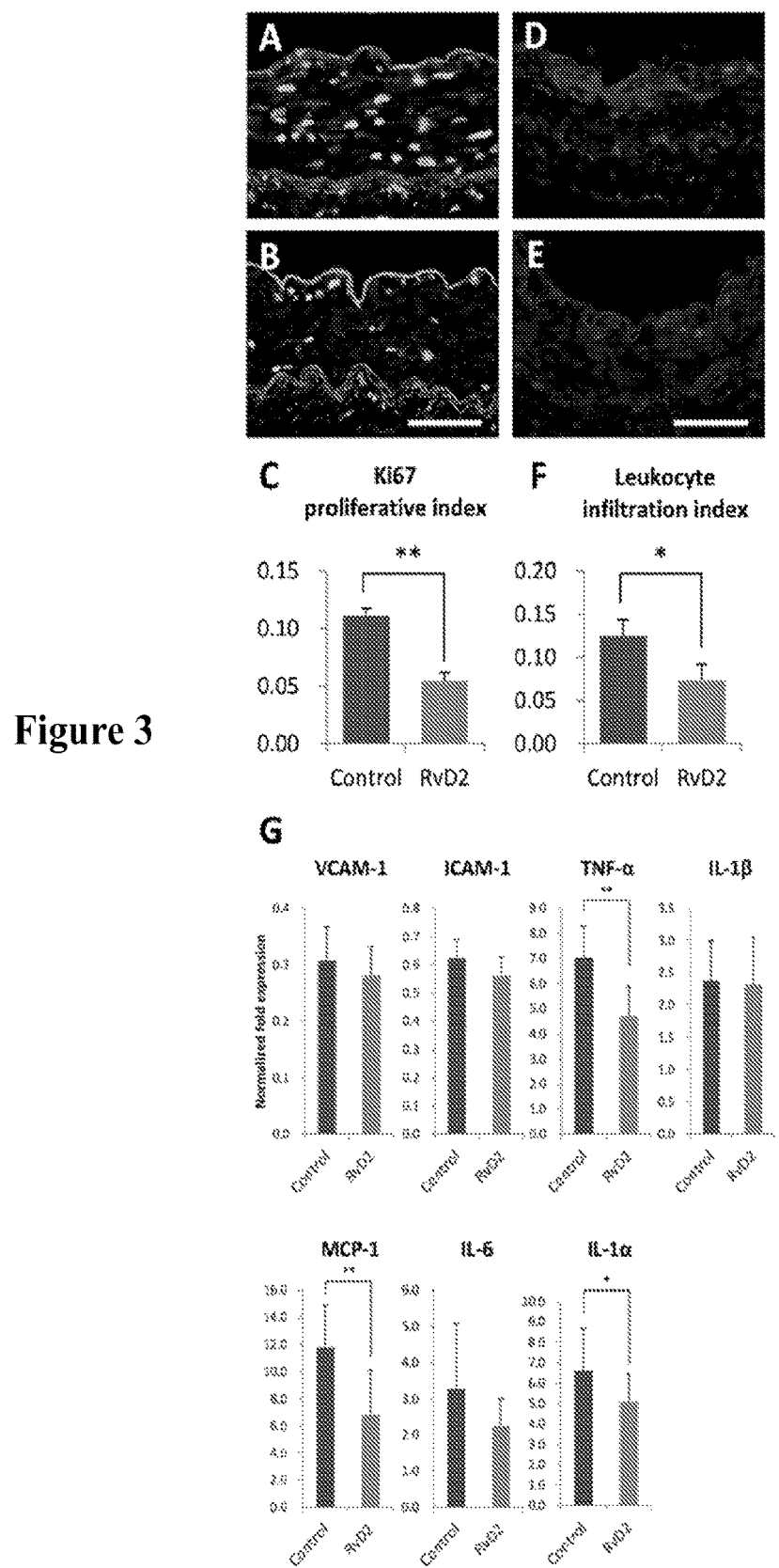
FIG. 3 shows RvD2 treatment attenuates the acute response to vascular injury, in-vivo: (A-C) RvD2 reduces the early proliferative response to angioplasty in rabbits. Representative Ki-67 immunostaining of vehicle-treated (A) and RvD2-treated (B) arteries are shown (bar=100 µm), with summary of quantitative analysis in bar graph (C). (D-F) RvD2 treatment attenuates early leukocyte recruitment to the injured vessel. Representative CD45 stained sections of vehicle-treated (D) and RvD2-treated (E) arteries are shown (bar=100 µm), with summary of quantitation in bar graph (F). (G) RvD2 treatment modulates early inflammatory gene expression in the acutely injured artery in-vivo. Shown are fold expression changes of VCAM-1, ICAM-1, TNF-α, IL-1β, MCP-1, IL-6, and IL-1α normalized to uninjured artery.

FIG. 3: RvD2 treatment attenuates the acute response to vascular injury, in-vivo. Rabbits (n=6) underwent bilateral femoral artery angioplasty, with immediate local delivery of RvD2 (10 nM) or vehicle control by intraluminal incubation as described. Vessels were harvest 3 days after injury for histological assays (results are mean±SEM, **$P<0.01$, *$P<0.05$, paired t-test). (A-C) RvD2 reduces the early proliferative response to angioplasty. Representative Ki-67 immunostaining of vehicle-treated (A) and RvD2-treated (B) arteries are shown (bar=100 μm), with summary of quantitative analysis in bar graph (C). (D-F) RvD2 treatment attenuates early leukocyte recruitment to the injured vessel. Representative CD45 stained sections of vehicle-treated (D) and RvD2-treated (E) arteries are shown (bar=100 μm), with summary of quantitation in bar graph (F). (G) RvD2 treatment modulates early inflammatory gene expression in the acutely injured artery in-vivo. Shown are fold expression changes of VCAM-1, ICAM-1, TNF-α, IL-1β, MCP-1, IL-6, and IL-1α normalized to uninjured artery (results are mean±SEM, **$P<0.01$, *$P<0.05$, paired t-test).

RvD1 and RvD2 Modulate VSMC Superoxide Production

Local generation of reactive oxygen species (ROS) such as superoxide potentiates inflammation and cell activation signaling in the vessel wall. ROS may be generated by recruited leukocytes or by resident vascular cells, including VSMC. In-vitro, RvD1 treatment significantly reduced TNF-α-induced superoxide production in VSMC (FIG. 4A-4D, 4I). In-vivo, DHE staining demonstrated a significant reduction of injury-induced ROS production in RvD2-treated rabbit arteries 3 days after balloon injury (n=6, % inhibition 43%, $P<0.05$, paired t-test) (FIG. 4E-4H, 4J).

FIG. 4: RvD treatment modulates superoxide production by VSMC in-vitro and in-vivo. (A-D, I) RvD1 treatment reduces TNF-α-induced superoxide production in cultured HVSMC. Representative merged images of DHE staining counterstained with DAPI of untreated VSMC (A), positive control (TNF-α 10 ng/ml for 4 hours, B), TNF-α with 10 nM RvD1(C), and TNF-α with 100 nM RvD1(D; bar=200 μm). Quantitative comparison of DHE staining intensity is shown in panel (I; n=3, results are mean±SEM, *$P<0.05$, one-way ANOVA followed by Dunnett's post hoc test). (E-H, J) RvD2 treatment reduces oxidative stress in the acutely injured rabbit artery (3 days post angioplasty). Representative images of DHE staining of an uninjured aorta (E), balloon injured and untreated iliac artery (F), vehicle-treated (G), and RvD2-treated (H) femoral arteries (bar=100 μm). Quantitative comparison of staining intensity is shown in panel (J; n=6, results are mean±SEM, *$P<0.05$, paired t-test).

RvD2 Attenuates Neointimal Hyperplasia in Balloon-injured Rabbit Arteries

The effects of locally delivered RvD2 treatment on neointimal hyperplasia were evaluated in the rabbit femoral artery 28 days after injury. Both neointimal area (0.27±0.03 vs 0.38±0.04 mm$^2$, P=0.002, paired t-test) and neointima/media ratio (0.77±0.06 vs 1.07±0.09 mm$^2$, P=0.007, paired t-test) were significantly reduced by RvD2 treatment (FIG. 5A-5C).

Figure 5:
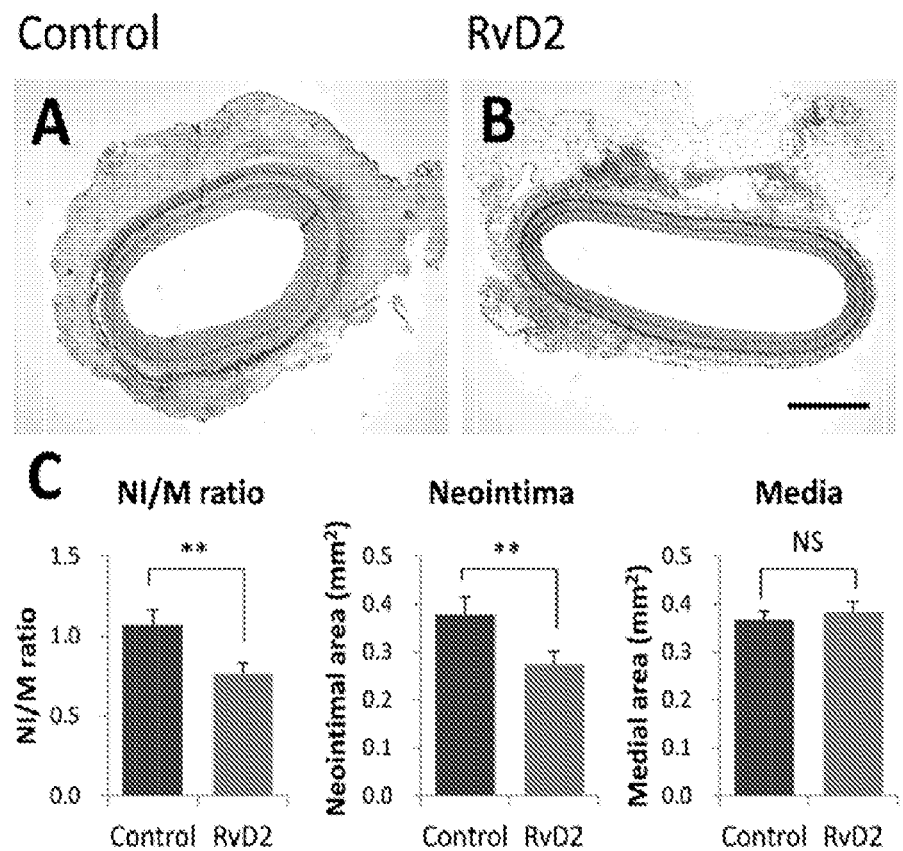
FIG. 5 shows RvD2 treatment inhibits neointimal hyperplasia post-angioplasty: Histomorphometric analysis of elastin-stained sections of vehicle-treated (A) vs RvD2-treated (B) rabbit arteries (bar=500 µm); morphometric results summarized in panel (C) show neointima/media (NI/M) ratio and neointimal area were significantly reduced in RvD2-treated vessels.

FIG. 5: RvD2 treatment inhibits neointimal hyperplasia post-angioplasty. Angioplasty and local treatment of bilateral rabbit (n=8) femoral arteries with RvD2 versus vehicle control was performed as described, and vessels were explanted at 28 days by perfusion-fixation. Histomorphometric analysis was performed on elastin-stained sections of vehicle-treated (A) vs RvD2-treated (10 nM, B) arteries (bar=500 μm), and morphometric results are summarized in panel (C). Neointima/media (NI/M) ratio and neointimal area were significantly reduced in RvD2-treated vessels (results are mean±SEM, **$P<0.01$, NS, not significant, paired t-test).

Figure 6:
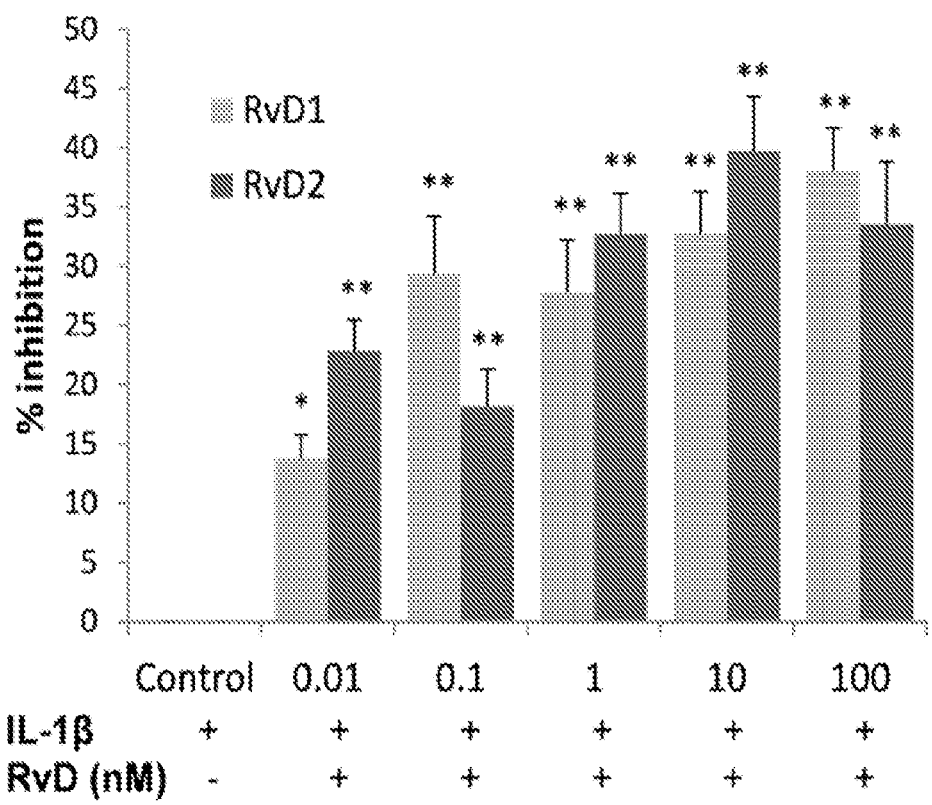
FIG. 6 shows doses of RvD1 and RvD2 modulate cell adhesion response of human VSMC to IL-1β. Shown is relative inhibition of human monocyte (U937) adhesion to VSMC cultures treated as indicated.

FIG. 6: RvD1 and RvD2 modulate cell adhesion response of human VSMC to IL-1β. HVSMCs were stimulated with IL-1β (1 nM) for 4 hours, in the presence or absence of RvD1 or RvD2 at the indicated doses. Labelled U937 monocytes were overlain, and cell adhesion assay performed as described. Results are shown as relative percent inhibition, expressed as a percentage of the maximal adhesion for the agonist (n=6, results are mean±SEM, **$P<0.01$, *$P<0.05$, unpaired t-test).

Figure 7:
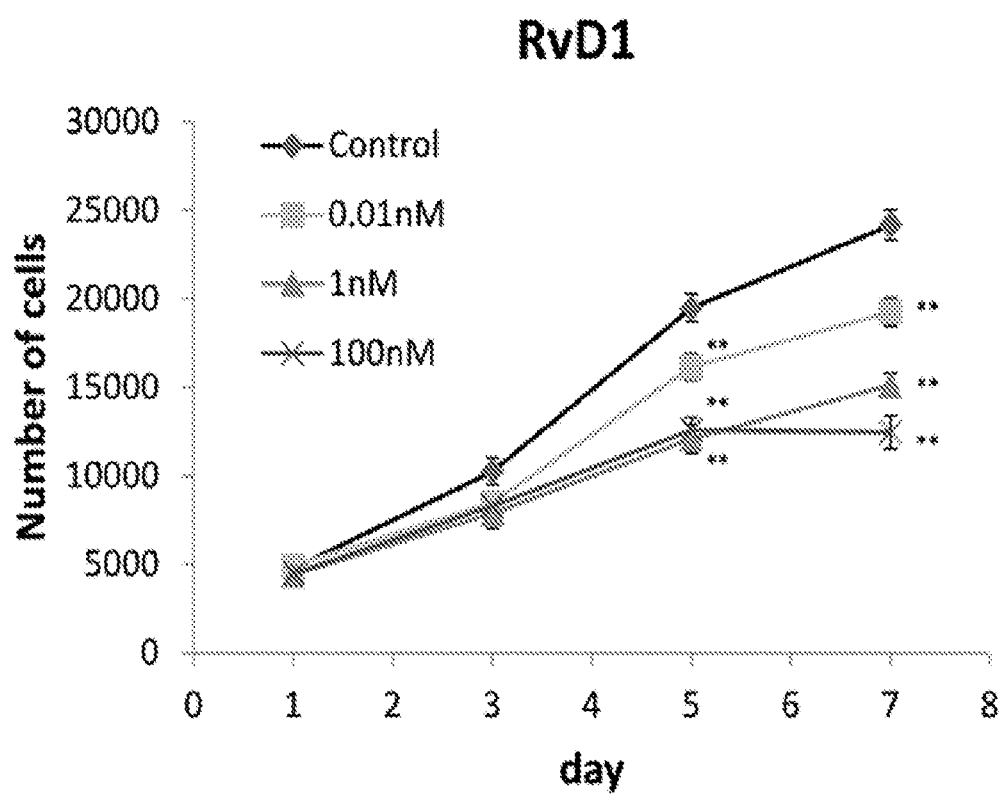
FIG. 7 shows RvD1 reduces proliferation of human VSMC in-vitro, in a dose-dependent fashion.
Figure 8:
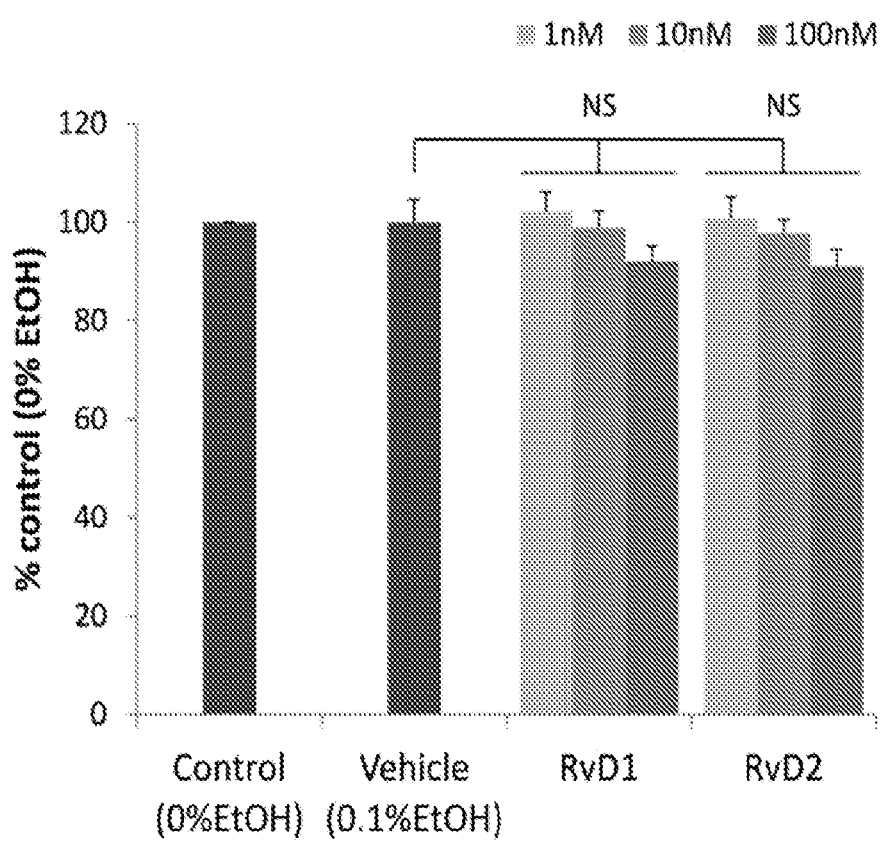
FIG. 8 shows that VSMC cell viability is not affected by RvD1 or RvD2 by MTT cell viability assay.

FIG. 7: RvD1 reduces proliferation of human VSMC in-vitro. HVSMC proliferation assay performed in normal growth medium (10% serum) as described in Methods. Dose-dependent inhibition of VSMC proliferation is shown for RvD1 (n=3, results are mean±SEM, **$P<0.01$ vs control, two-way ANOVA followed by Dunnett's post hoc test).

FIG. 8: Cell viability is not affected by RvD1 or RvD2. Cells were treated with or without RvD1 or RvD2 (1, 10, and 100 nM) for 8 hours. MTT cell viability assay indicated that VSMC exposed to RvD1 or RvD2 had no significant loss of cell viability (n=4, results are mean±SEM, NS, not significant, one-way ANOVA vs vehicle control (0.1% ethanol (EtOH)) followed by Dunnett's post hoc test).

FIG. 9: Effects of RvD2 on gene expression in VSMC are sensitive to pertussis toxin (PTX). VSMCs were exposed to TNF-α and RvD2 (10 nM) as described in FIG. 2, in the presence or absence of PTX (100 ng/ml). RNA was harvested and analyzed for the expression of ICAM-1, IL-1β, and IL-1α by qPCR (n=3, results are mean±SEM, **$P<0.01$, *$P<0.05$, one-way ANOVA followed by Bonferroni's post hoc test).

FIG. 10: Identification of GPR32 in human VSMC. Western blot analysis (50 μg of total cell lysate) of primary cultured VSMC from two different donors using anti-GPR32 antibody and anti-β actin antibodies. A single band is identified of the appropriate size for each protein.

Figure 11:
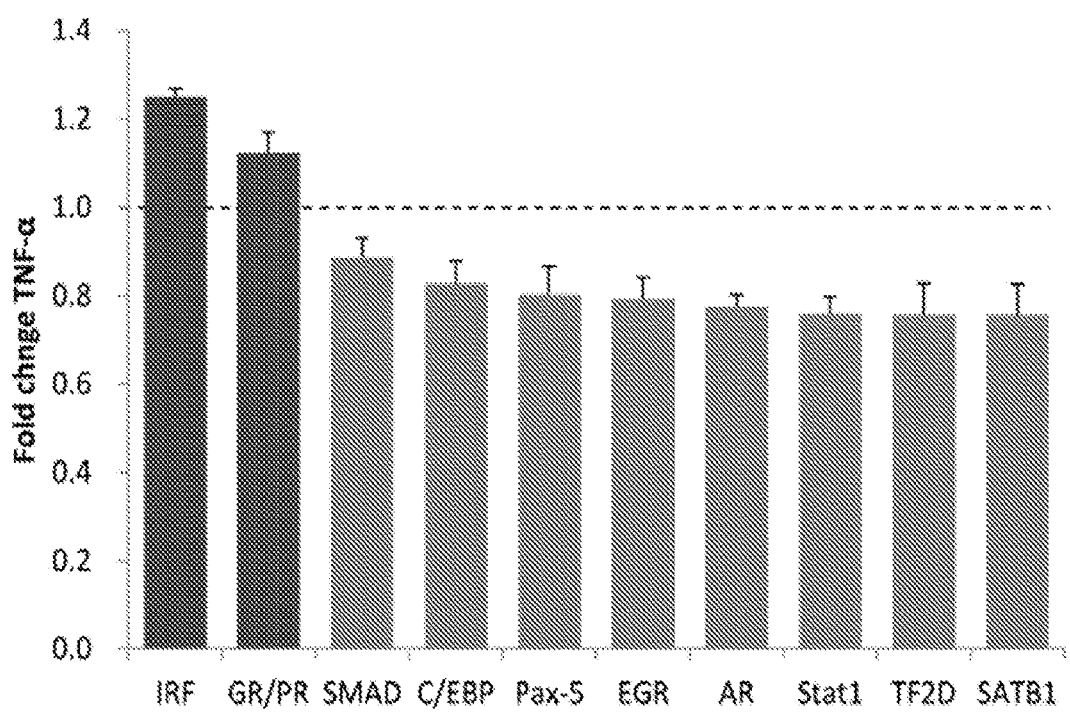
FIG. 11 shows RvD1 and RvD2 modulate activity of multiple transcription factors in TNF-α-stimulated VSMC. Shown are representative data summarizing transcription factors, which were significantly upregulated (left) or downregulated (right) by RvD2 co-treatment compared to TNF-α alone.

FIG. 11: RvD1 and RvD2 modulate activity of multiple transcription factors in TNF-α-stimulated VSMC. VSMCs were treated with TNF-α (10 ng/ml) for 18 hours and nuclear extracts were prepared. Transcription factor profiling was performed using a multiplex array. Shown are representative data summarizing transcription factors which were significantly upregulated (left) or downregulated (right) by RvD2 co-treatment (10 nM) compared to TNF-α alone (n=3, results are mean±SEM, P<0.05 vs TNF-α alone, one-way ANOVA followed by Dunnett's post hoc test).

Pro-resolving Vascular Devices (PRVDs)

Figure 12:
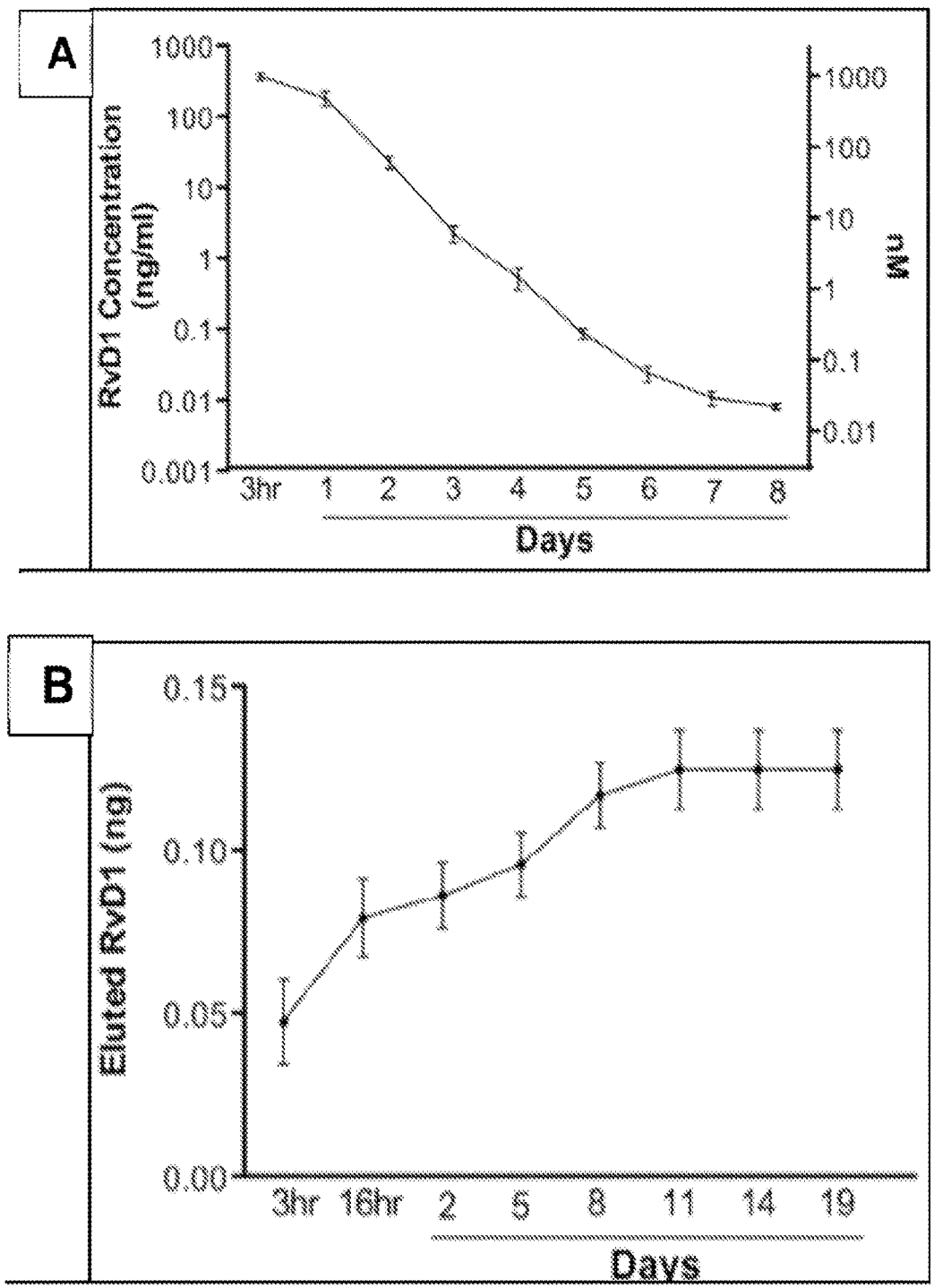
FIG. 12 illustrates the elution of RvD1 from two pro-resolving vascular devices (PRVD): (A) nanotubular coated nitinol stent coupons loaded with RvD1 in transwell; and (B) elution of RvD1 from thin film PCL wrap prototypes, shown as cumulative over time.
Figure 13:
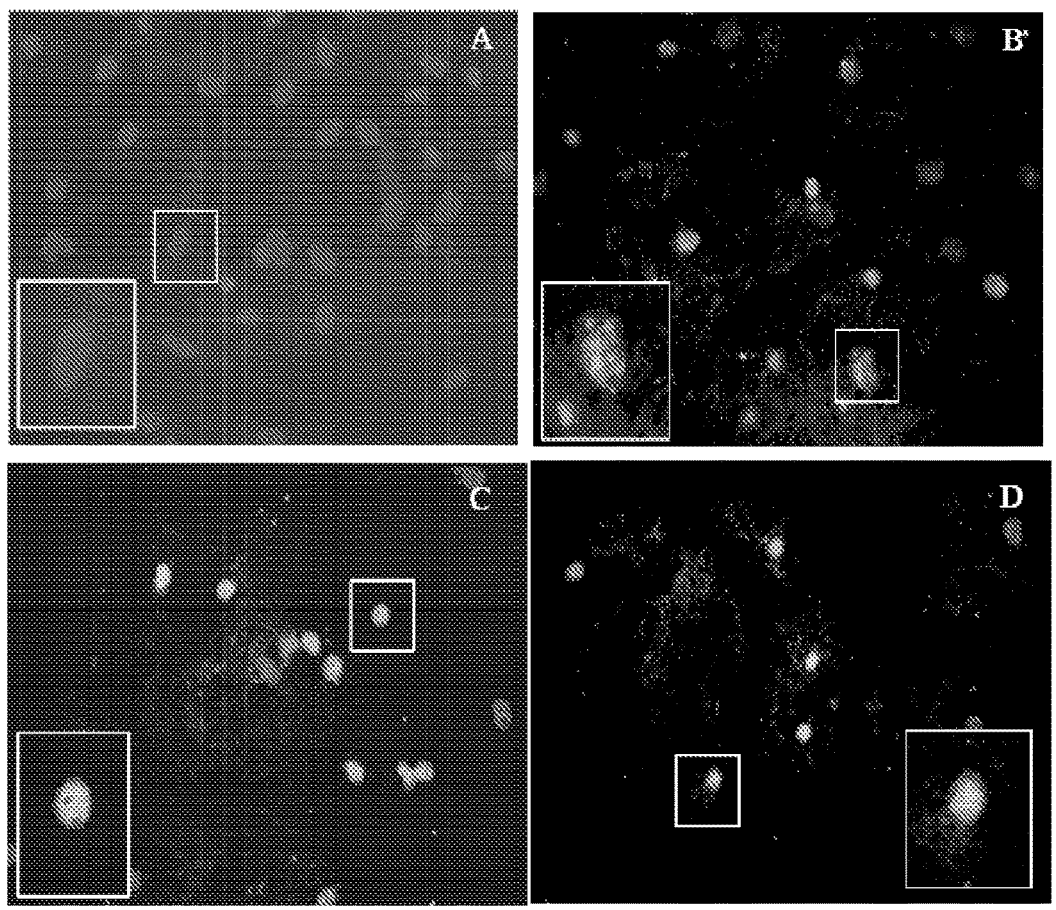
FIG. 13 shows that 7S and 7R-Maresin-1 reduce TNFα induced superoxide production in VSMC and EC. (A-D) merged images of DHE and DAPI staining of untreated cells, TNF-α alone, TNF plus 100 nM 7R Mar-1, TNF plus 100 nM 7R Mar-1 plus PTX. DHE channel fluorescence quantification from multiple experiments summarized in panels E and F.
Figure 13:
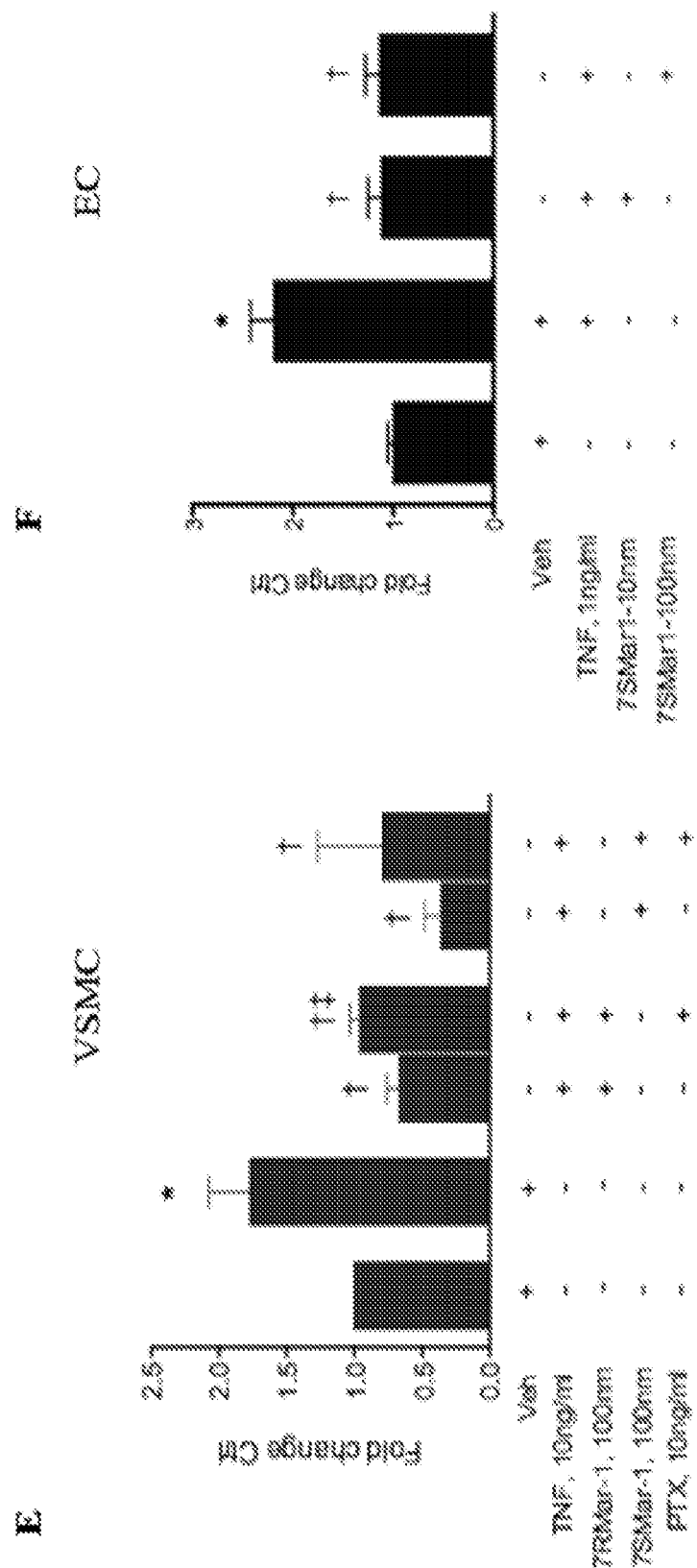

PRVDs (both stents and wraps) have been generated to characterize lipid mediator loading and elution profiles. Prototype PRVDs were placed in transwell insert chambers with media sampling over hours to days (FIG. 12). An ELISA (Cayman) was utilized to quantify RvD1 concentration. Nanotubes were prepared on 4×4 mm nitinol coupons; nanotubes had a diameter of 50 nm and a length of 1.2 μm. To load the 4×4 mm nanotube coated nitinol coupon, 8 ul of solution (RvD1 100 ng/ul) was added to the full surface, then evaporated (10 minutes at RT). Over the first two days (FIG. 12A), RvD1 was readily available at a relative high release rate. During the following 5 days the elution became more constant, but lower, then depleted. To obtain a sustained release over 28 days, the number of loading cycles is increased and/or the tube length is increased, i.e. their capacity, while keeping the tube diameter constant. These longer tubes are loaded with larger amounts of RvD1. Furthermore, release kinetics is modulated by increasing or decreasing the tube diameter by varying the applied voltage. Alternatively, the affinity of RvD1 to the substrate is increased by introducing a hydrophobic coating to its surface, e.g., using a fluoro-silane. Thin film devices (FIG. 12B) were prepared by adding 5 ug of RvD1 drug to a 75 mg/ml solution of 80 kDa polycaprolcatone in trifluoroethanol. The solution was spun cast at 1000 rpm for 30 seconds then ramped over 5 seconds to 2000 rpm for 30 seconds. An approximately 4 mm×4 mm piece was cut for each experiment.

FIG. 12: Elution of RvD1 from prototype PRVDs. (A) Nanotubular coated nitinol stent coupons loaded with 800 ng RvD1 in transwell. Concentration measured via complete media exchange. (B) Elution of RvD1 from thin film PCL wrap prototypes, shown as cumulative over time.

Optimization of Elution Profile of PRVDs

Without wishing to be bound by theory, one desired drug elution profile for a PRVD is based on the vascular injury responses in animal models and humans, the hypothesized MOA and dose-dependent effects of the pro-resolving lipid mediators. Local concentration of 1 nM lipid mediator is achieved within 4 hours and maintained≥1 nM through 14 days; between 1-7 days levels are≥10 nM; and then levels≥0.1 nM are maintained for ≥4 weeks. Specifically, elution of the lipid mediator attenuates the acute inflammatory response, and its early conversion to a resolution phase. Therefore, therapeutic levels of PRM are made available to the vessel wall within hours, and maintained through the first several days of early leukocyte recruitment. Cell migration and proliferation attenuates significantly beyond one month in most animal models; therefore levels of anti-proliferative and anti-migratory PRM activity are maintained for 1-4 weeks.

Fabrication and Modifications of Prototype Drug Eluting Stent Devices

The optimal geometries of nanotubes to achieve a therapeutic elution of PRM therapy are identified. This is achieved via fabrication of highly uniform titania nanotubes with controllable size parameters in order to modulate release kinetics. The length of the nanotube array is varied from 100 nm to 10s of microns, the thickness of the nanotube walls, and the nanotube pore diameter from 10s of nm to 100s of nm. The large surface area of the nanotube-array structure, the ability to precisely tune pore size, wall-thickness, and nanotube length are used to optimize the implant surfaces. Coupons containing titania nanotube arrays of varying pore size are synthesized from Ti metal or Nitinol by anodization, immersed in an electrolyte and an electrical potential applied between the anode and a Pt cathode. Depending upon the anodization bath chemistry, nanotube growth rates range from approximately 1 μm/hr to 30 μm/hr. In fluoride-containing electrolytes the anodization of titanium is accompanied with the chemical dissolution of titanium oxide due to the formation of $TiF_6$. Highly ordered nanotube arrays are formed at relatively low potentials, e.g., 10 V, as a result of the competition between the electro-chemical etching and the chemical dissolution. Nanotubes on stents are synthesized by placing stents into the center of five circular arranged, parallel to the stent oriented Pt-wires, functioning as cathodes. Using this setup, varying voltage, temperature of the electrolyte and synthesis time, controls nanotube length, wall thickness and diameter.

Electropolished Nitinol stents are used as substrate of 3×15 mm (OD, length). Electropolishing removes debris from the surface and releases surface tension, and may support the growth of homogeneous nanotube arrays. Nanotube synthesis is performed over a time of 5 to 90 minutes, using a mixture of ethylene glycol, water and ammonium fluoride as electrolyte (90:10; 3 g/l), and a voltage between 10 to 90 V. Afterwards stents are rinsed with ethanol and debris are removed using ultrasound for 5-30 minutes while immersed in ethanol. Stents are stored in ethanol at RT. Prior to drug-loading, stents are dried under vacuum and loaded with the drug. In brief, the nanotubes are loaded with the drug by either dip-coating, or evaporation of the drug containing solvent. The procedure is repeated until the desired amount of drug is reached, or no more drug can be loaded. In the latter case, the nanotube length, and diameter, is adjusted to increase loading capacity.

The ability of the surfaces to elute various molecules is estimated using fluorescein and the resolvins. The drug is loaded by applying a small volume of concentrated drug solution directly onto the surface and then placing the surfaces under a vacuum for over 2 hours. The surfaces are then be immersed in PBS, agitated 100 rpm, and the amount of drug elution is measured at various time points using a fluorometer or UV-plate reader and ELISA assays. The effect that oxide thickness and pore diameter might have on drug elution kinetics is examined using the same drug elution method. These experiments involve oxide thicknesses ranging from 1 μm to 10 μm (with 150 nm diameter pores), and diameters from 50 nm and 200 nm (with the default height of 10 μm).

7S and 7R-Maresin-1 Reduce TNFα Induced Superoxide Production

As noted above, local generation of reactive oxygen species (ROS) such as superoxide potentiates inflammation and cell activation signaling in the vessel wall. ROS may be generated by recruited leukocytes or by resident vascular cells, including VSMC. 7S-Maresin-1 treatment significantly reduced TNF-α-induced superoxide production in VSMC and EC.

FIGS. 13A-13D. Representative merged images of DHE staining, counterstained with DAPI. (A), Negative control. (B), TNFα at 10 ng/ml for 4 hr. C) TNFα at 10 ng/ml for 4 hr with 100 nM 7R-Maresin-1 and (D), TNFα at 10 ng/ml for 4 hr with 100 nM 7R-Maresin-1 and 10 ng/ml pertussis toxin. (E) Quantitative comparison of DHE staining intensity in the nucleus of human saphenous vein vascular smooth muscle (sv-VSMC) cells, treated with TNFα and 7S and 7R-Maresin-1 with and without pertussis toxin. (F) Quantitative comparison of cellular ROS production by CellRox (Life technologies, Carlsbad, Calif.) in human saphenous vein endothelial (EC) cells treated with TNFα (1 ng/nil) and 7S-Maresin-1 (N>=3). P≤0.05, One-way ANOVA with Dunnett's post hoc test. *: P≤0.05 compared to control, unpaired t-test. †: P≤0.05 compared to TNFα, unpaired t-test. ‡: P≤0.05 compared to TNFα+7R-Maresin-1, unpaired t-test. Error bars: SEM.

7S-Maresin-1 Attenuates TNFα Induced NADPH-Oxidase 4 Expression

NADPH oxidases (NOX) are the dominant source of superoxide generation in blood vessels and have been strongly implicated in vascular injury. NOX4 is a dominant isoform bound in VSMC and blood vessels. Regulation of NOX4 expression and activity therefore is of interest. Human sv-VSMCs were pretreated with 7S-Maresin-1 or vehicle for 30 min, followed by TNFα at 10 ng/ml for 4 hr. Whole cell lysates were blotted for NOX4 (Abcam Inc.) and beta-actin (Sigma).

Figure 14:
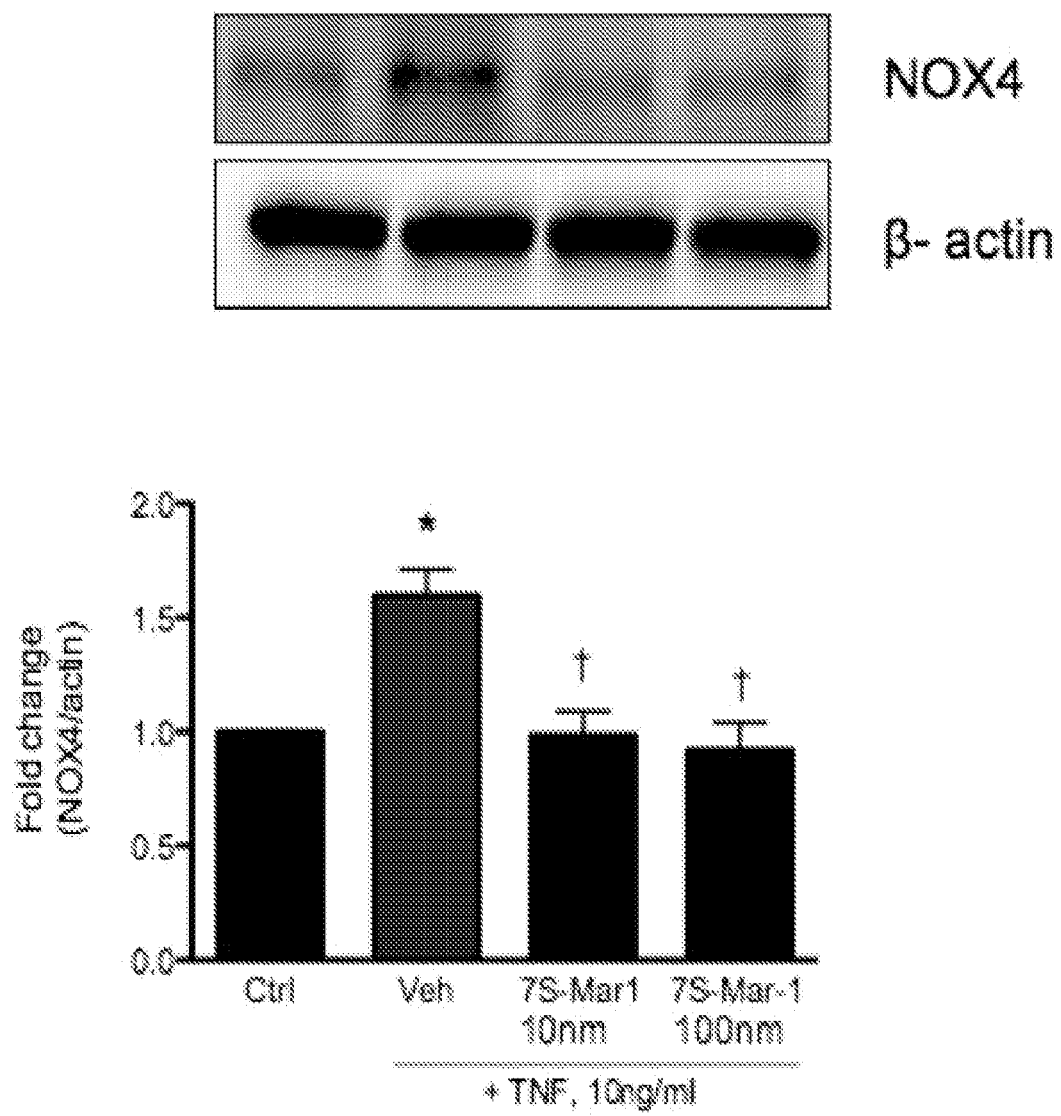
FIG. 14 illustrates that 7S-Maresin-1 attenuates TNFα induced NADPH-oxidase 4 expression in human saphenous vein smooth muscle cells (sv-VSMCs).
Figure 15:
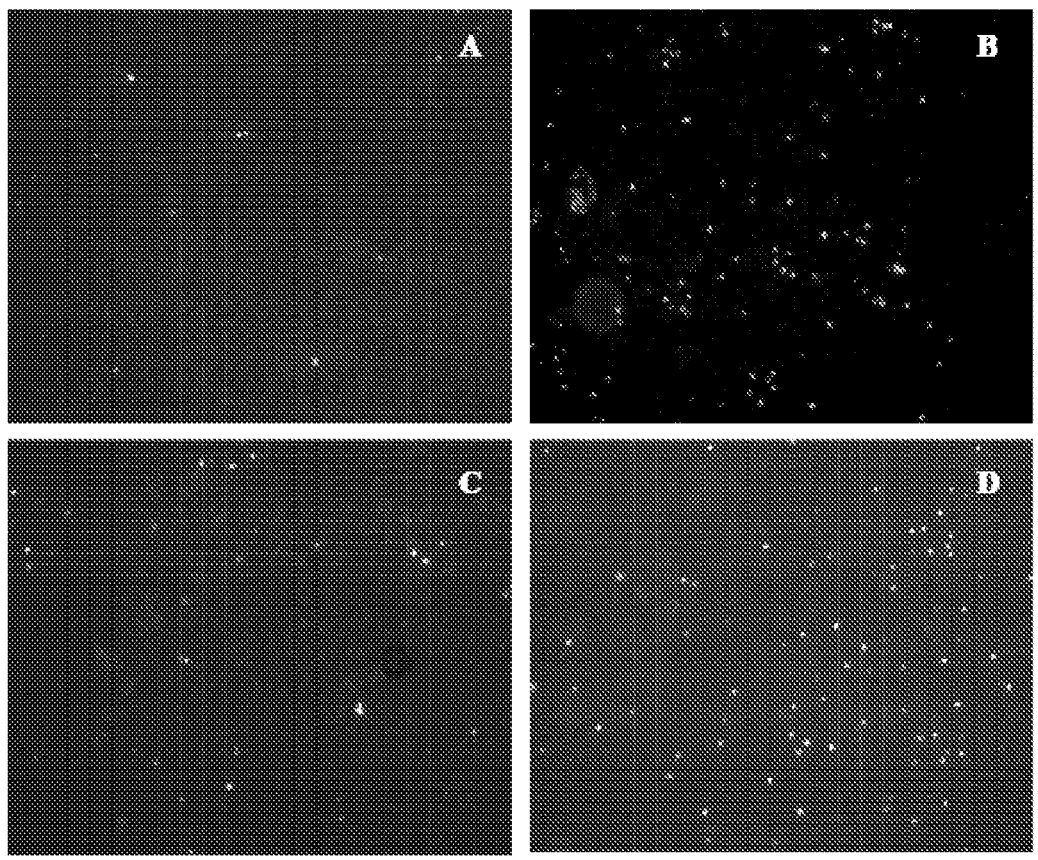
FIG. 15 shows that 7S-Maresin-1 attenuates monocyte (U937) adhesion to TNFα activated VSMC and EC, in a dose dependent fashion (A-F). Panel G shows inhibition of VCAM-1 expression by Western blot. Panel H shows inhibition of MCP-1 gene expression in similar fashion.
Figure 15:
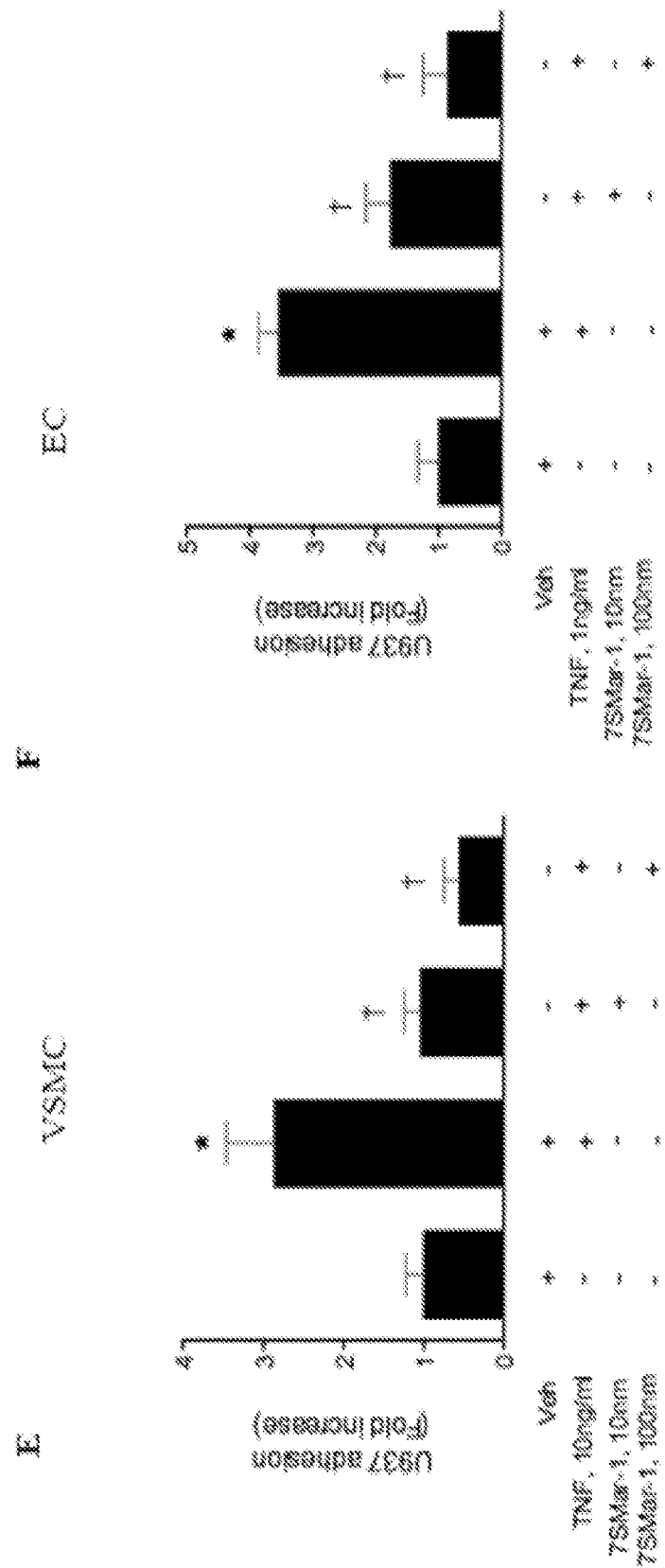
Figure 15:
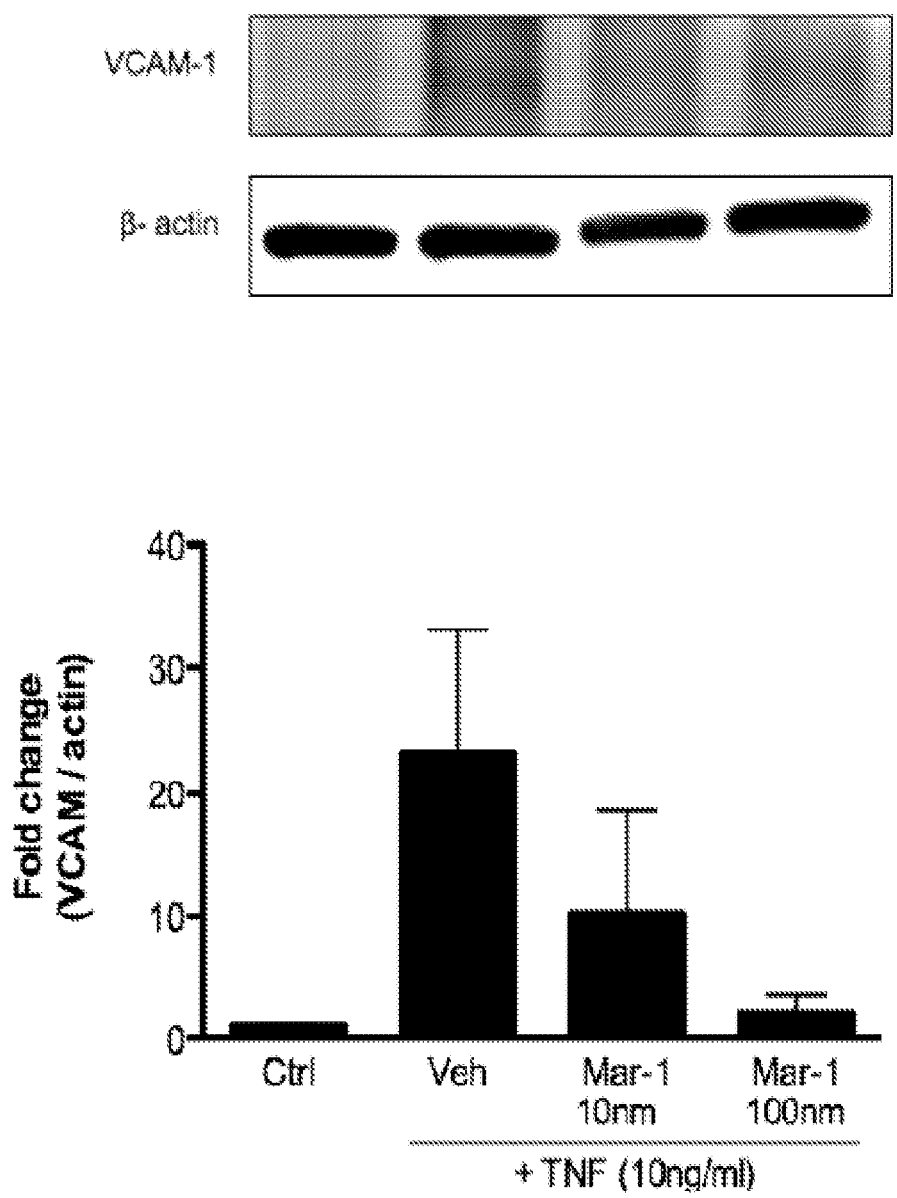
Figure 15:
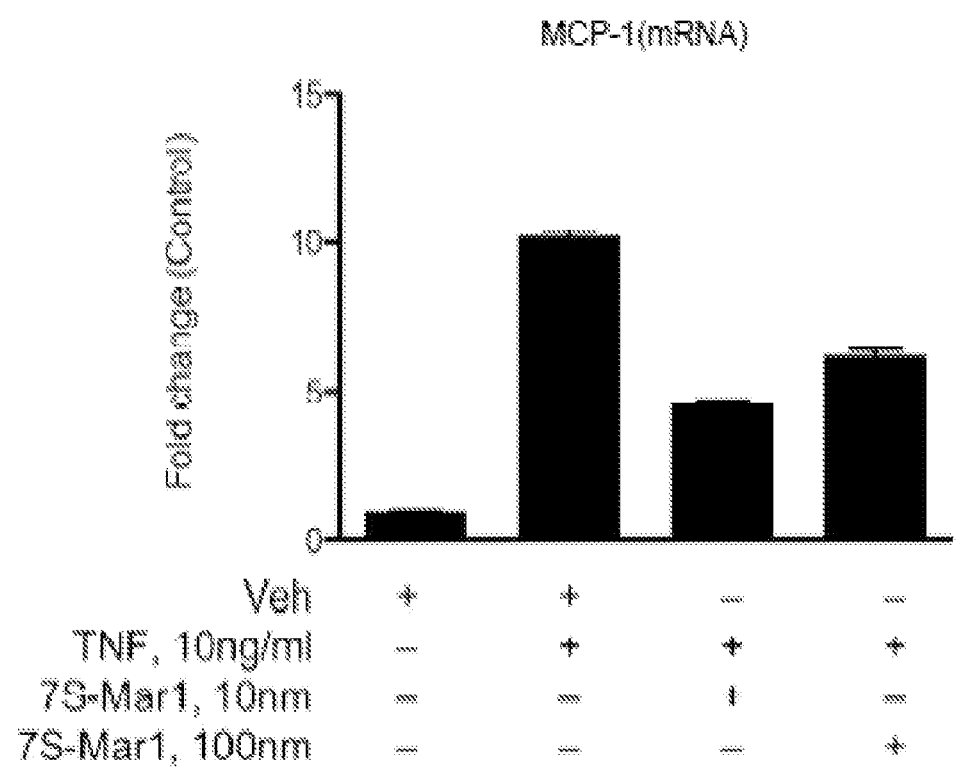
Figure 16:
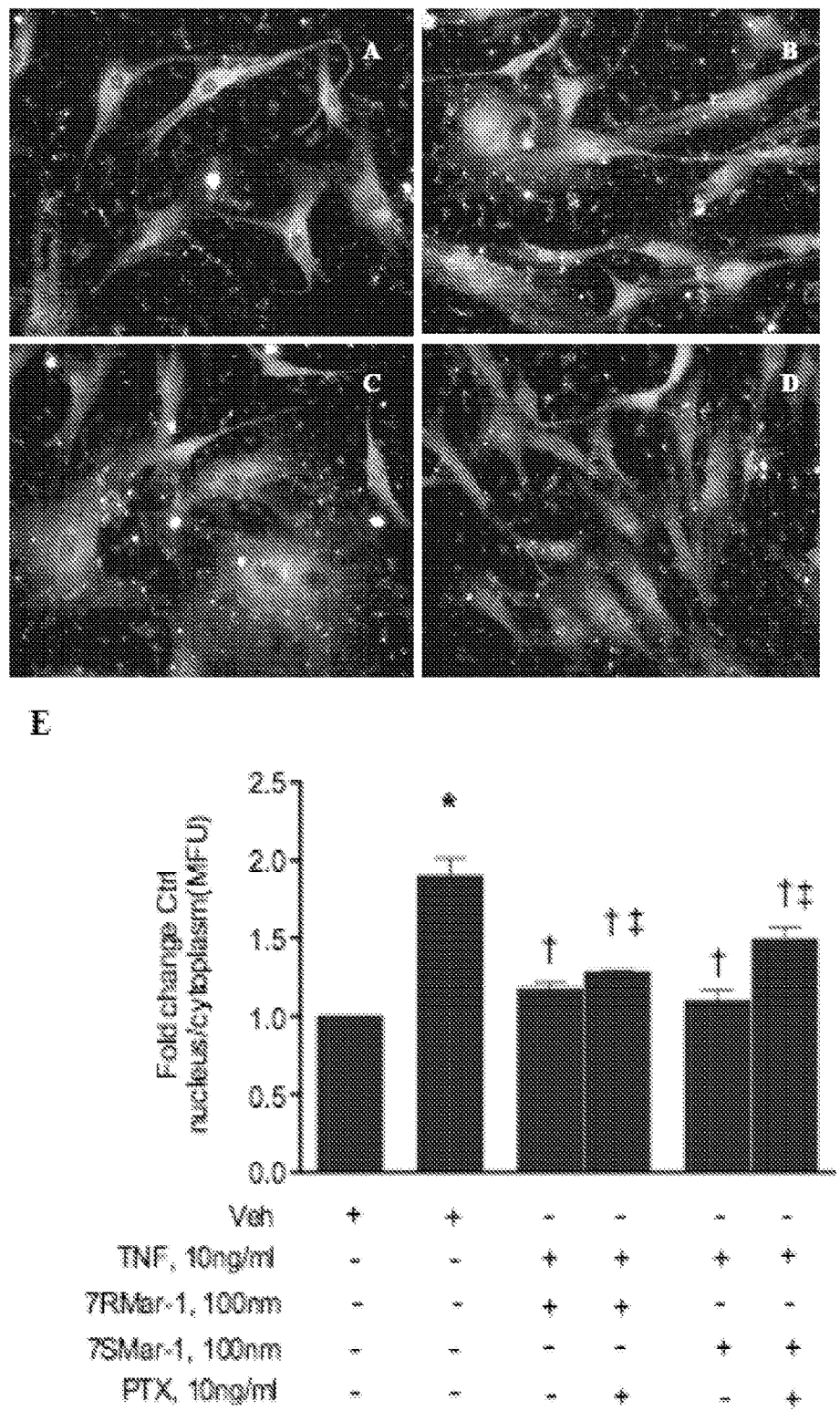
FIG. 16 illustrates that 7S and 7R-Maresin-1 inhibits TNFα-stimulated nuclear translocation of p65 subunit in human sv-VSMCs (A-E).
Figure 17:
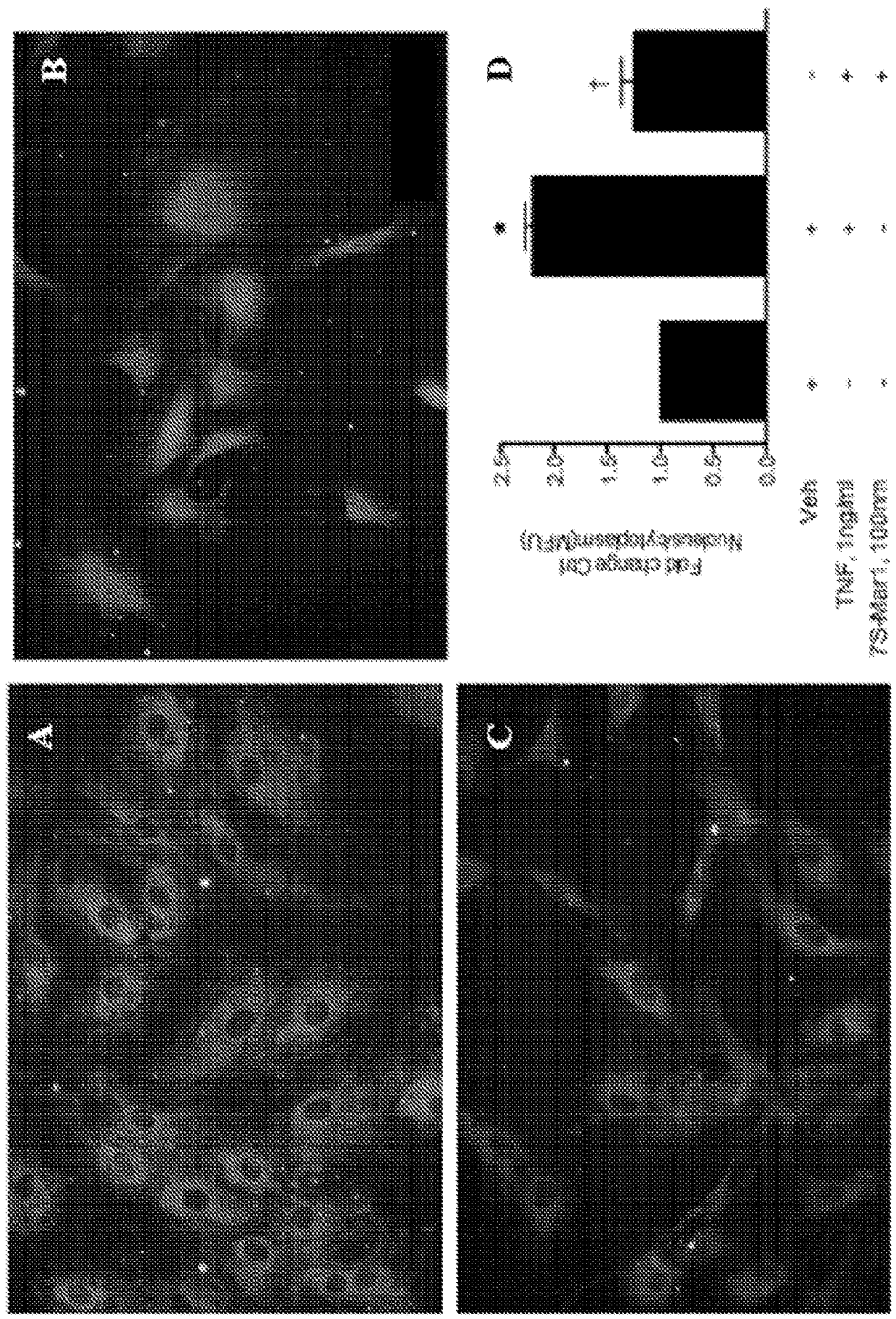
FIG. 17 shows that 7S-Maresin-1 inhibits TNFα-stimulated nuclear translocation of p65 subunit in human VECs (A-D).

FIG. 14. NOX4 and beta-actin western blotting image is representative of three independent experiments. Bar graph represents net quantitative densitometry analysis. N=3. P≤0.05, One-way ANOVA with Dunnett's post hoc test. *: P≤0.05 compared to control, unpaired t-test. †: P≤0.05 compared to TNFα, unpaired t-test. Error bars: SEM.

7S-Maresin-1 Attenuates Cell Adhesion in TNFα Activated VSMCs and ECs

As noted above, following acutely denuding mechanical injury such as balloon angioplasty, exposed lumenal VSMC take on a pro-adhesive, proliferative, and migratory phenotype which may be modeled using standard in-vitro assays. In a static cell adhesion assay, 7S-Maresin-1 produced a dose-dependent inhibition of monocyte adhesion (U937) to TNF-α-stimulated VSMC and EC. Similar results were obtained using 7R Mar-1.

FIGS. 15A-15D. Representative images of Calcein-AM labeled U937 monocytes adhered to human sv-VSMCs pretreated with vehicle (A, B) or 7S-Maresin-1 (C) or 7S-Maresin-1 and pertussis toxin (D) for 30 min, followed by TNFα at 10 ng/ml for 4 hr (B, C, D). (E) Quantitative analysis of U937 adhesion assay in human sv-VSMCs and (F) human sv-ECs (1 ng/ml TNFα used for EC cells). P≤0.05, One-way ANOVA with Dunnett's post hoc test. *: P≤0.05 compared to control, unpaired t-test. †: P≤0.05 compared to TNFα, unpaired t-test. ‡: P≤0.05 compared to TNFα+7S-Maresin-1, unpaired t-test. (G) VSMCs were pretreated with 7S-Maresin-1 or vehicle for 30 min, followed by TNFα at 10 ng/ml for 4 hr. Whole cell lysates were blotted for VCAM-1 (Pierce Inc.) and beta-actin (Sigma). VCAM-1 and beta-actin western blotting image is representative of three independent experiments. Bar graph represents net quantitative densitometry analysis. N=3. P=0.06, One-way ANOVA with Kruskal Wallis nonparametric test. P=0.07 of TNFα, compared to control, Mann Whitney test. P=0.20 of 7S-Maresin-1 at 10 nm and 100 nm compared to TNFα, Mann Whitney test. Error bars: SEM. (H) Mar-1 treatment reduced MCP-1 expression by TNF-α stimulated VSMCs. MCP-1 is a potent chemokine which enhances monocyte and leukocyte recruitment and activation at sites of vascular injury. VSMCs were treated with TNF-α (10 ng/ml) for 18 hours, in the presence or absence of Mar-1 (10, 100 nM). Expression of MCP-1 was measured by qRT-PCR, and normalized to unstimulated cells (n=3, results are mean±SEM, P<0.05 for Mar-1 (10 and 100 nM) vs TNF alone, unpaired t-test).

7S and 7R-Maresin-1 Inhibit Nuclear Translocation of p65 Subunit in Human sv-VSMCs The transcription factor NF-κB family is a central regulator of the inflammatory response, coordinating the expression of multiple pro-inflammatory cytokines and adhesion molecules in vascular cells. NF-κB is a heterodimer consisting of a member of the Rel family (commonly RelA, or p65) and either p50 or p52. In unstimulated cells, the NF-κB dimers are sequestered in the cytoplasm by a family of inhibitory proteins known a IκB. When an inflammatory signal is transduced, specific kinases (IKKs) are activated (by phosphorylation) and, in turn, phosphorylate IκB at specific serine residues, leading to its ubiquitination and degradation. When IκB is degraded, the NF-κB complex is released and translocates to the nucleus, where it binds to regulatory elements in multiple genes to enhance transcription. Thus the translocation of NF-κB to the nucleus is a critical step in the transduction of pro-inflammatory signaling pathways. Nuclear translocation of p65 can be monitored using an in-vitro fluorescence assay.

FIGS. 16A-16D. VSMCs were grown in chamber slides and treated with vehicle or 100 nm of 7S or 7R-Maresin-1 with/without 10 ng/ml pertussis toxin for 30 min, followed by TNFα (10 ng/ml) for 2 hrs. Cells were fixed and subsequently stained with anti-p65 (Santa Cruz Biotechnology) and secondary antibodies (Alexa-488). (A-D) Representative images of Ctrl (A), TNFα (B), 7R-Maresin-1+TNFα (C) and 7R-Maresin-1+pertussis toxin (10 ng/ml)+TNFα. (E) Mean fluorescence of nucleus and cytoplasm were quantified from all groups and the net result of the ratio of nucleus over cytoplasmic mean fluorescence is depicted in the bar graph, as a measure of relative p65 nuclear translocation. (N>=3). P≤0.05, One-way ANOVA with Dunnett's post hoc test. *: P≤0.05 compared to control, unpaired t-test. †: P≤0.05 compared to TNFα, unpaired t-test. ‡: P≤0.05 compared to TNFα+7R or 7S-Maresin-1, unpaired t-test. Error bars: SEM.

7S-Maresin-1 Inhibits Nuclear Translocation of p65 Subunit in Human sv-ECs

ECs were grown in chamber slides and treated with vehicle or 100 nm of 7S-Maresin-1 for 30 min, followed by TNFα (1 ng/ml) for 2 hrs. Cells were fixed and subsequently stained with anti-p65 (Santa Cruz Biotechnology) and secondary antibodies (Alexa-488).

FIGS. 17A-17D. Representative images of Ctrl (A), TNFα (B), 7S-Maresin-1+TNFα. (C). (D) Mean fluorescence of nucleus and cytoplasm were quantified from all groups and the net result of the ratio of nucleus over cytoplasmic mean fluorescence is depicted in the bar graph, as a measure of relative p65 nuclear translocation. (N>=3). P≤0.05, One-way ANOVA with Dunnett's post hoc test. *: P≤0.05 compared to control, unpaired t-test. †: P≤0.05 compared to TNFα, unpaired t-test. Error bars: SEM.

7S-Maresin-1 and 7R-Maresin-1 Reduce TNFα Induced Phosphorylation of IKKα/β Subunit in Human sv-VSMCs and sv-ECs As noted above, phosphorylation of IKK proteins is a key initial step to the activation of NF-κB in cytokine stimulated cells. Inhibition of phosphorylation of IKK would lead to attenuation of inflammatory signaling pathways.

Cells were pretreated with 100 nm of 7S/7R-Maresin-1 for 30 min, followed by TNFα (10 ng/ml for VSMC and 1 ng/ml for EC) for 15 min. Whole cell lysates were collected and probed for pan and phospho IKK (Cell Signaling Inc.).

Figure 18:
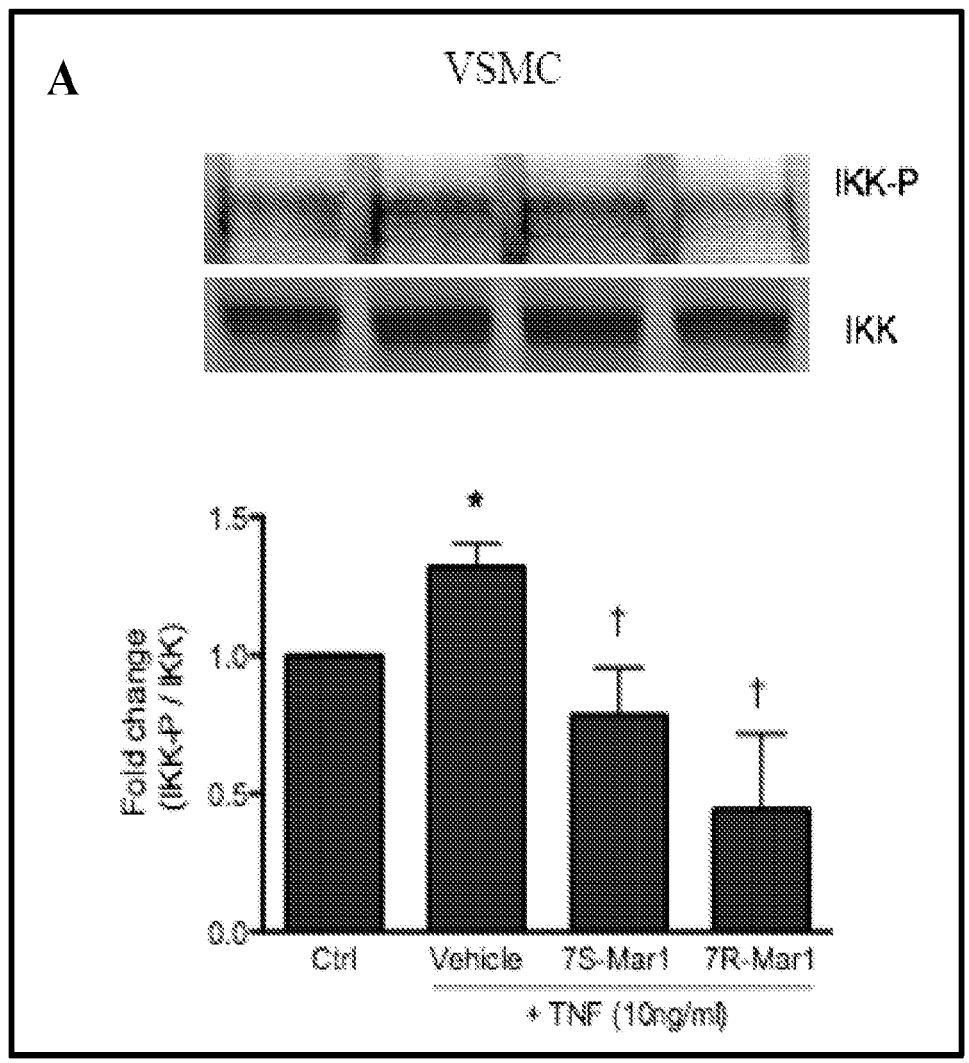
FIG. 18 shows that 7S-Maresin-1 and 7R-Maresin-1 reduce TNFα induced phosphorylation of IKKα/β subunit in human sv-VSMCs (A) and sv-ECs (B).
Figure 18:
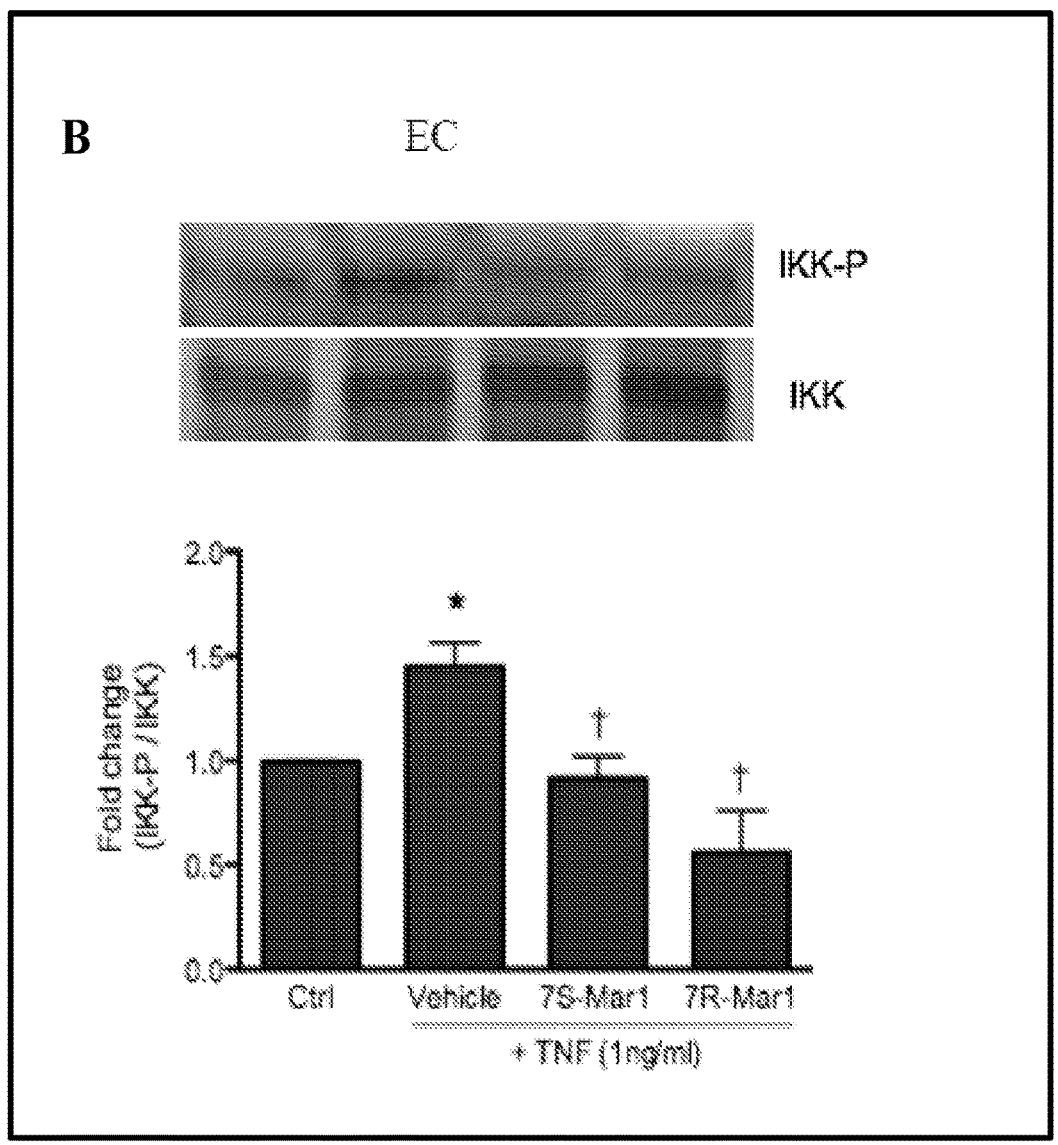

FIG. 18. IKK-phospho and total IKK western blotting image is representative of three independent experiments. Bar graph represents net quantitative densitometry analysis. N=3. P≤0.05, One-way ANOVA with Dunnett's post hoc test. *: P≤0.05 compared to control, unpaired t-test. †: P≤0.05 compared to TNFα, unpaired t-test. Error bars: SEM.

Figure 19:
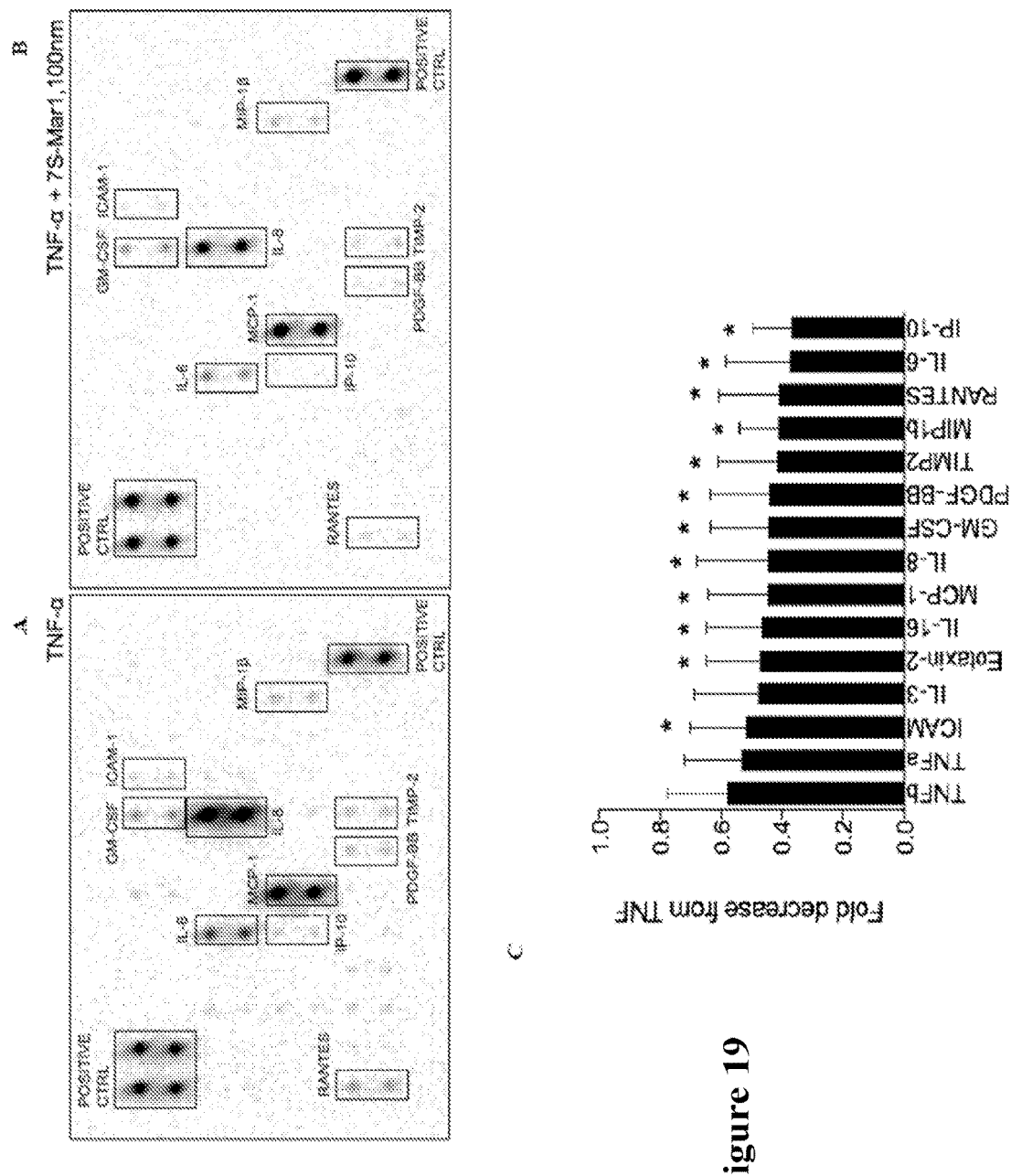
FIG. 19 illustrates that 7S-Maresin-1 diminishes TNFα induced extracellular release of multiple pro-inflammatory mediators from human sv-ECs (A-C).
Figure 20:
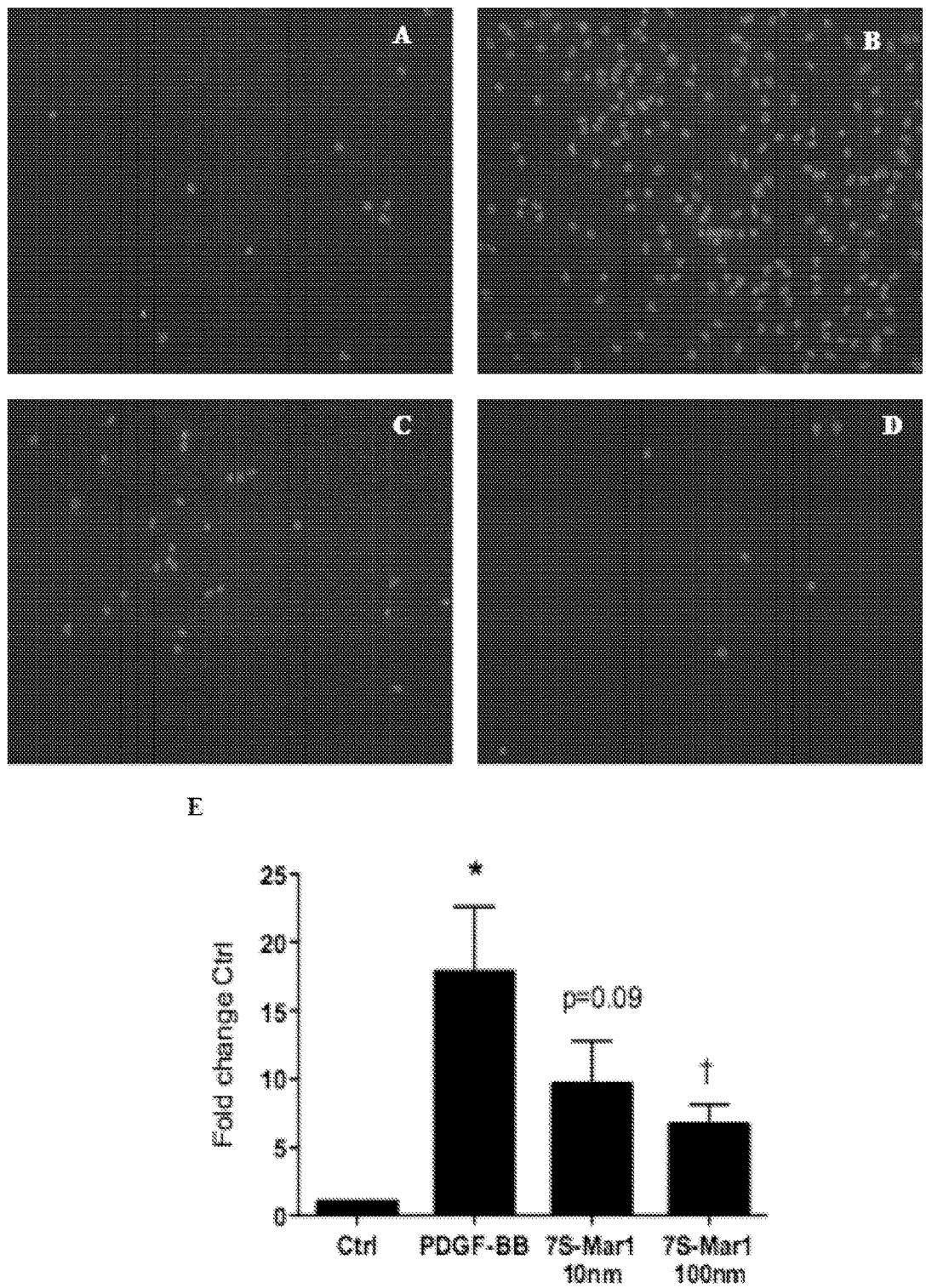
FIG. 20 shows that 7S-Maresin-1 dose-dependently attenuates PDGF-BB induced migration of human sv-VSMCs, using Transwell assay (A-E).
Figure 21:
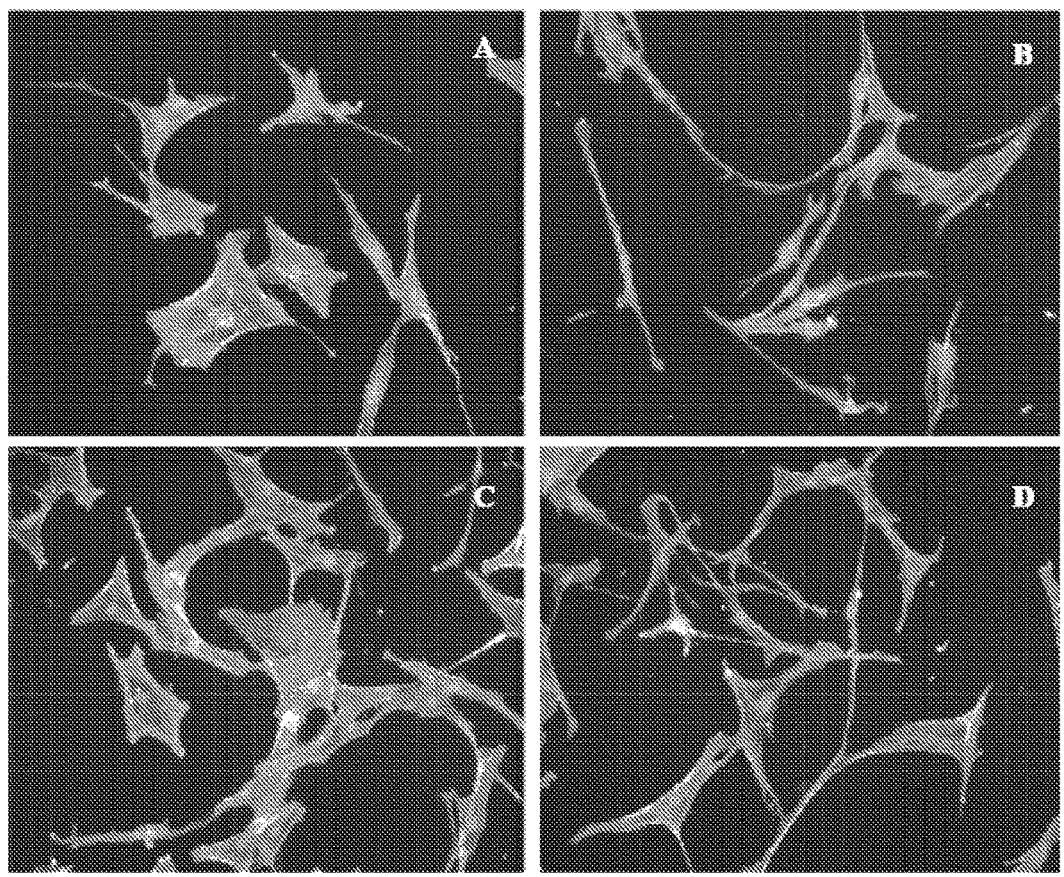
FIG. 21 shows that 7S-Maresin-1 alters PDGF-BB induced cytoskeletal changes in VSMC consistent with reduced migration response (A-E).
Figure 21:
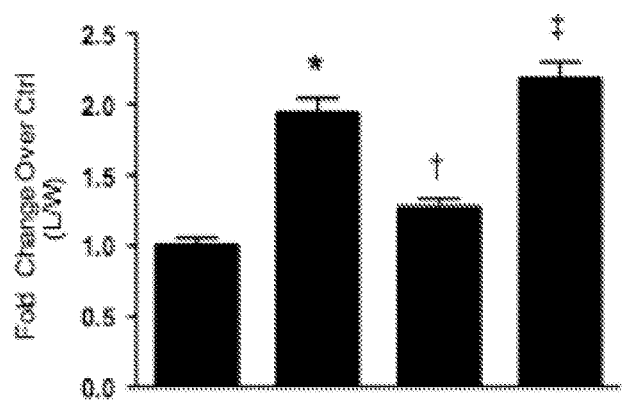

7S-Maresin-1 Diminishes TNFα Induced Extracellular Release of Inflammatory Mediators in Human sv-ECs Inflammatory signals are amplified by autocrine and paracrine pathways that include the elaboration of pro-inflammatory mediators into the local extracellular milieu. Cells grown in 6 cm dish were serum starved for 24 hrs. The cells were then pre-treated with 100 nm 7S-Maresin-1 for 30 min followed by 18 hrs of TNF α (1 ng/ml). Cell culture media was collected and incubated with human inflammation cytokine array membranes (AAH-INF-3-4, Raybiotech Inc.), coated with antibodies (in duplicate) recognizing 40 different inflammatory mediators. As shown in FIG. 19, levels of multiple inflammatory mediators were reduced in conditioned medium from EC treated with Mar-1 post-TNF stimulation (both versus vehicle).

FIGS. 19A-19C. (A, B) Representative membrane images from a set of three pairs. (C) Densitometric quantitation of each of the attenuated inflammatory mediators in three independent experiments was performed and is represented in the bar graph. No inflammatory mediators were found to be up-regulated. Values were normalized to protein content of each dish.*: P≤0.05 compared to TNFα, unpaired t-test. Error bars: SEM.

7S-Maresin-1 Dose-Dependently Attenuates PDGF-BB Induced Migration in Human sv-VSMCs VSMCs were pre-treated with vehicle or 7S-Maresin-1 for 30 min in a transwell insert before adding PDGF-AB (50 ng/ml) to the outer chamber. Migrated VSMCs were fixed with methanol, stained with DAPI and counted under a fluorescent microscope.

FIGS. 20A-20D. Representative image of nine independent experiments. (A) Vehicle Control. (B) PDGF-BB, 50 ng/ml. (C) 7S-Maresin-1, 1 nm+PDGF-BB, 50 ng/ml. (D) 7S-Maresin-1, 100 nm+PDGF-BB, 50 ng/ml. (E) Graphical summary of nine independent experiments. P≤0.01, One-way ANOVA with Dunnett's post hoc test. *P<0.05 compared to PDGF-AB (50 ng/ml). Error bars: SEM. †: P≤0.05 compared to TNFα, unpaired t-test. P=0.09 for 7S-Maresin-1, 1 nm+PDGF-BB, compared to PDGF-BB alone, Mann Whitney t-test.

7S-Maresin-1 Alters PDGF-BB Induced Vascular Smooth Muscle Cell Shape Change

The chemotaxis response of VSMC to growth factors such as PDGF involves receptor-mediated signal transduction followed by a cytoskeletal reorganization to polarize the cell for migration. The cytoskeletal change include polymerization and polarization of actin filaments, and is a rapid event upon exposure to agonists of migration. Modulation of these immediate cytoskeletal responses can therefore strongly influence cell migration.

Human sv-VSMCs cultured in chamber slides were treated with 7S-Maresin-1 at 100 nM or vehicle for 30 min, followed by PDGF-BB, 50 ng/ml for 1 hr. Cells were then fixed, permeabilized and stained with phalloidin (Life technologies).

FIGS. 21A-21E. (A) Vehicle Control. (B) PDGF-BB, 50 ng/ml. (C) 7S-Maresin-1, 100 nm+PDGF-BB, 50 ng/ml. (D) 7S-Maresin-1, 100 nm+pertussis toxin, 10 ng/ml+PDGF-BB, 50 ng/ml. (E) Graphical summary of N=4 per group. P≤0.01, One-way ANOVA with Dunnett's post hoc test. *P<0.05 compared to PDGF-BB (50 ng/ml). †: P≤0.05 compared to PDGF-BB alone, unpaired t-test. ‡: P≤0.05 compared to PDGF-BB+7S-Maresin-1, unpaired t-test. Error bars: SEM.

Systemic Administration of RvD2 or 7R Mar-1 Reduces Neointima Formation Following Carotid Artery Ligation in Mice To examine the potential therapeutic effects of systemic administration of pro-resolving mediators in acute vascular injury, a standardized mouse model of carotid ligation was employed. FVB Mice (N=23) were treated with intraperitoneal administration of RvD2 (100 ng/dose), 7R Mar-1 (100 ng/dose) or vehicle on days 0 (4 hrs prior to carotid injury), 1, 3, 5 and 7. Total dose received was 500 ng/mouse. Unilateral carotid ligation was performed as a standardized model of vascular injury, induced by low shear. Animals were then sacrificed at 14 days and perfusion-fixed vessels explanted for analysis. Following elastin staining, neointima (NI) and medial (M) compartments were measured by a blinded observer, and ratios (area and average wall thickness) calculated. Analysis was performed at mid CCA level (2.5 mm from ligature).

Figure 22:
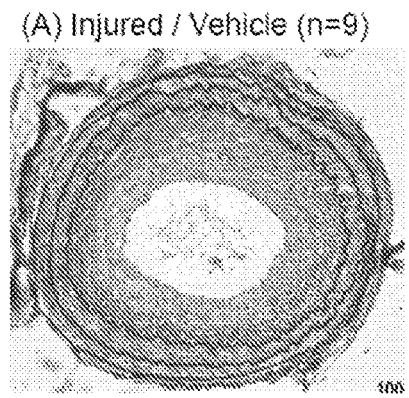
FIG. 22 shows that systemic administration of RvD2 or 7R Mar-1 reduces neointima formation and alters artery remodeling following carotid artery ligation in male FVB mice (A-E).
Figure 22:
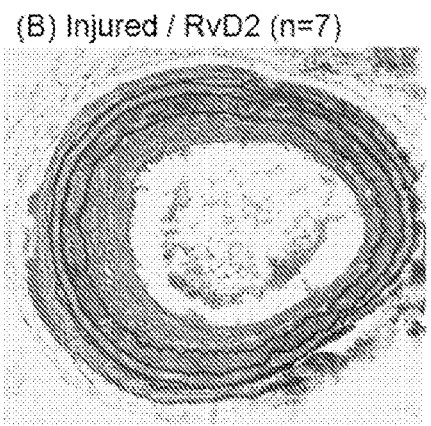
Figure 22:
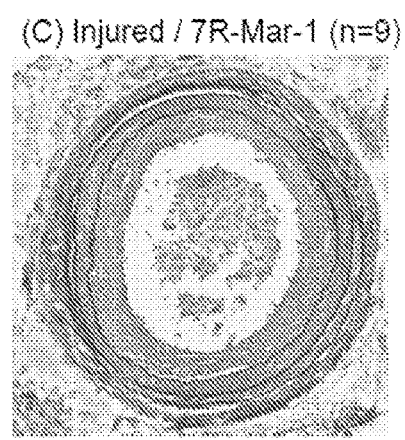
Figure 22:
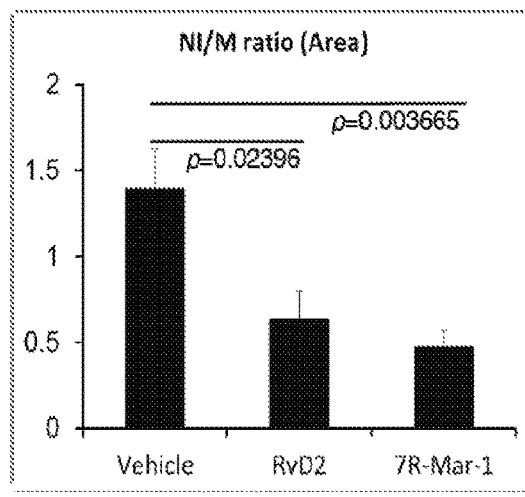
Figure 22:
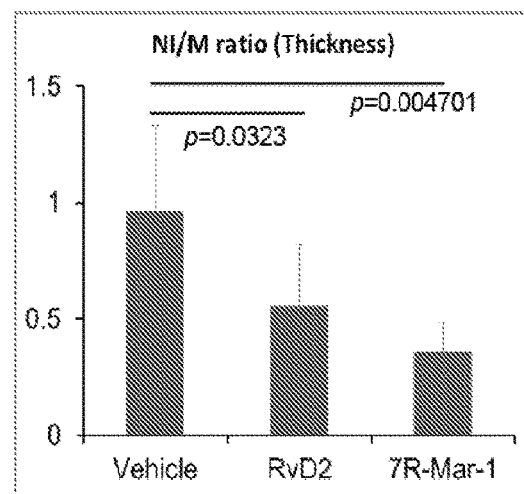

FIG. 22. (A)-(C), depict a cross-section of a carotid artery at mid CCA level (2.5 mm from ligature) from carotid ligation mouse model administered vehicle (A), RvD2 (B), or 7R-Mar-1 (C). (D)-(E) depict NUM ratio of the cross-section of the carotid artery at mid CCA level from carotid ligation mouse model administered vehicle, RvD2, or 7R-Mar-1. NUM ratio of area of the cross-section of the carotid artery at mid CCA level is shown in D, while NUM ratio of average thickness of the cross-section of the carotid artery at mid CCA level is shown in E. Comparisons made by ANOVA followed by unpaired t-tests.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of reducing inflammatory response of vascular smooth muscle cells of a vascular wall to vascular injury or restenosis of a vascular wall following injury, the method comprising:
   positioning a vascular device at or adjacent the vascular wall,
   wherein the vascular device releases a pro-resolving lipid mediator in an amount sufficient to reduce the inflammatory response to the vascular injury or restenosis of the vascular wall,
   wherein the vascular device is a stent or a perivascular wrap,
   wherein the pro-resolving lipid mediator comprises Maresin-1, RvD1, or RvD2.

2. The method of claim 1, wherein the pro-resolving lipid mediator is Maresin-1.

3. The method of claim 1, wherein the method resolves vascular wall inflammation.

4. The method of claim 1, wherein method reduces restenosis of the vascular wall.

5. The method of claim 1, wherein the pro-resolving lipid mediator is RvD1.

6. The method of claim 1, wherein the pro-resolving lipid mediator is RvD2.

7. The method of claim 1, wherein the stent comprises a surface comprising a coating comprising a nanotube comprising nitinol.

8. The method of claim 1, wherein the perivascular wrap comprises a biodegradable polymer comprising polycaprolactone.

* * * * *